US006174901B1

(12) United States Patent
Mantlo et al.

(10) Patent No.: US 6,174,901 B1
(45) Date of Patent: Jan. 16, 2001

(54) SUBSTITUTED PYRIDINE AND PYRIDAZINE COMPOUNDS AND METHODS OF USE

(75) Inventors: Nathan B. Mantlo, Lafayette; Chan-Kou Hwang; Ulrike D. Spohr, both of Boulder, all of CO (US)

(73) Assignee: Amgen Inc., Thousand Oaks, CA (US)

( * ) Notice: Under 35 U.S.C. 154(b), the term of this patent shall be extended for 0 days.

(21) Appl. No.: 09/215,426

(22) Filed: Dec. 18, 1998

Related U.S. Application Data

(60) Provisional application No. 60/068,199, filed on Dec. 19, 1997.

(51) Int. Cl.$^7$ ...................... C07D 403/04; C07D 401/04; A61K 31/496; A61K 31/497; A61K 31/4418; A61K 31/4427

(52) U.S. Cl. .......................... 514/333; 544/326; 544/327; 544/328; 544/330; 544/331; 544/333; 544/364; 544/238; 544/295; 544/296; 544/298; 544/299; 544/300; 544/310; 544/316; 544/319; 544/320; 544/321; 544/323; 544/324; 546/139; 546/140; 546/141; 546/142; 546/143; 546/144; 546/148; 546/152; 546/153; 546/155; 546/156; 546/157; 546/159; 546/167; 546/255; 546/256; 546/257; 546/268.1; 514/252.05; 514/253.01; 514/256; 514/269; 514/272; 514/274; 514/275; 514/277; 514/307; 514/308; 514/309; 514/310; 514/311; 514/312; 514/313; 514/314; 514/332; 514/334; 514/336; 514/337; 514/339; 514/340; 514/343

(58) Field of Search ..................................... 514/256, 269, 514/272, 274, 275, 277, 307, 308, 309, 310, 311, 312, 313, 314, 332, 333, 334, 336, 337, 339, 340, 343, 252.03, 253.01; 544/238, 295, 296, 298, 299, 300, 310, 316, 319, 320, 321, 323, 324, 326, 327, 328, 330, 331, 333, 364; 546/281.1, 268.1, 139, 140, 141, 142, 143, 144, 152, 153, 155, 156, 157, 159, 167, 164, 165, 255, 256, 257, 148

(56) References Cited

U.S. PATENT DOCUMENTS

| 3,946,024 | 3/1976 | Fleckenstein et al. ............ 360/294.9 |
| 4,011,328 | * 3/1977 | Pinhas et al. ......................... 424/263 |
| 4,533,666 | 8/1985 | Matsumoto et al. ................. 514/277 |
| 5,250,530 | 10/1993 | Giencke et al. ...................... 514/256 |
| 5,366,982 | 11/1994 | Dereu et al. .......................... 514/340 |
| 5,461,053 | 10/1995 | Boigegrain et al. ................. 514/247 |
| 5,861,419 | * 1/1999 | Dube et al. ............................ 514/334 |

FOREIGN PATENT DOCUMENTS

| 0 039 051 | 11/1981 | (EP) . |
| 0 308 020 | 3/1989 | (EP) . |
| 0 388 619 | 9/1990 | (EP) . |
| 1 238 959 | 2/1973 | (GB) . |
| 2 306 108 | 4/1997 | (GB) . |
| 6-135934 | 5/1994 | (JP) . |
| WO 92/02513 | 2/1992 | (WO) . |
| WO 96/24584 | * 8/1996 | (WO) . |
| WO 97/05877 | 2/1997 | (WO) . |
| WO 97/05878 | 2/1997 | (WO) . |
| WO 97/04778 | * 2/1997 | (WO) . |
| WO 97/11943 | * 4/1997 | (WO) . |
| WO 96/03387 | 4/1997 | (WO) . |
| WO 97/16442 | 5/1997 | (WO) . |
| WO 98/03484 | * 1/1998 | (WO) . |

OTHER PUBLICATIONS

Ciufolini et al. A Unified Strategy for the Synthesis of Phenanthroizidine Alkoloids: Preparation for Sterically Congested Pyridines, J. Am. Chem. Soc. 118, pp. 12082–12089, Dec. 13, 1996.*
Freisen et al. 2–Pyridinyl–3–(4–Methylsulfonyl)phenylpyridines: Selective and Orally Acive Cyclooxygenase–2 Inhibitors, Bioorg. Med. Chem. Lett., 19(8), pp. 2777–2782, Oct. 6, 1998.*
Unemara et al. Synthesis of the Central Heterocyclic Skeleton of an Antibiotic, A10255, Chem. Lett., pp. 1203–1204, Jan. 16, 1998.*
Zoltewicz et al. Inter–ring Directed Ortho Lithiation by the 2–Pyridyl Group in Bipyridines, Tetrahedron, 52(46), pp. 14469–14474, Nov. 27, 1996.*
Florin et al., Ann. Pharmaceutiques Francaises, 43:6, 595–599 (1985) (English translation attached).
Svensson et al., Drug Metabolism Reviews, 19(2), 165–194 (1988).
Bundgaard, J. Med. Chem., 32(12), 2503 (1989).
Dornow et al., Chem. Ber 87, pp. 985 (1954) (English translation attached).
Davies et al., J. Chem. Soc., Chem. Commun., pp. 1153 (1993).
Ninomiya et al., Tetrahedron, 30:2151 (1974).
Firestein et al., American Journal of Pathology, vol. 140, p. 1309 (1992).
Lang et al., Endocrinilogy, vol. 130, p. 43 (1992).
Szalkowski et al., Endrocrinology, vol. 136, p. 1474 (1995).
Wheeler et al., Journal of Labelled Compounds and Radiopharmaceuticals, vol. XXXI, No. 4, pp. 305 (1992).

(List continued on next page.)

* cited by examiner

Primary Examiner—Mukund J. Shah
Assistant Examiner—T. Ben Schroeder
(74) Attorney, Agent, or Firm—Frank Ungemach; Steven M. Odre

(57) ABSTRACT

Selected novel substituted pyridine and pyridazine compounds are effective for prophylaxis and treatment of diseases, such as TNF-α, IL-1β, IL-6 and/or IL-8 mediated diseases, and other maladies, such as cancer, pain and diabetes. The invention encompasses novel compounds, analogs, prodrugs and pharmaceutically acceptable salts thereof, pharmaceutical compositions and methods for prophylaxis and treatment of diseases and other maladies or conditions involving inflammation, cancer, pain, diabetes and the like. The subject invention also relates to processes for making such compounds as well as to intermediates useful in such processes.

31 Claims, No Drawings

OTHER PUBLICATIONS

Trentham et al., Journal of Experimental Medicine, vol. 146, pp. 857 (1977).
Shohami et al., J. Cereb. Blood Flow Metab., 14:615–619 (1994).
Lahdevirta et al., The American J. Med., 85:289 (1988).
Clouse et al., J. Immunol., 142:431–438 (1989).
Maini et al., Immunological Reviews, No. 144, pp. 195–223 (1995).
Davies et al., J. Chem. Soc., Perkin Trans I, pp. 1129 (1994).
Liu et al., Neuroscience Letters, 164:125–128 (1993).
Liu et al., Stroke, 25:1481–1488 (1994).
Gilligan et al., J. Med. Chem., 35:4344–4361 (1992).
Wermuth et al., J. Med. Chem., 30:239–249 (1987).
Cooper et al., Clin. Exp. Immunol., vol. 89, pp. 244 (1992).
Grussenmeyer et al., PNAS USA, vol. 82, pp. 7952–7954 (1985).
Thompson et al., J. Org. Chem., 49:5237–5243 (1984).
Berge et al., Journal of Pharmaceutical Sciences, vol. 66, No. 1, pp. 1 (1977).
Williams et al., PNAS USA, vol. 89, pp. 2922–2926 (1992).
Beutler et al., Journal of Immunology, vol. 135, p. 3969 (1985).
Folks et al., Journal of Immunology, vol. 136, pp. 4049 (1986).
Dinarello, Eur. Cytokine Netw., vol. 5, pp. 517–531 (1994).
Brahn et al., Lymphokine and Cytokine Research, vol. 11, pp. 253 (1992).
Baracos, et al., The New England Journal of Medicine, vol. 308, p. 553 (1983).
Chandrasekhar et al., Clinical Immunology and Immunopathology, vol. 55, pp. 382–400 (1990).
Ravina et al., Eur. J. Med. Chem., 20:5, pp. 475–479 (1985).
Brunner et al., Eur. J. Med. Chem., vol. 25, pp. 35 (1990).
Cohen et al., J. Am. Chem. Soc., 86:725–728 (1964).
Winter et al., Proc. Soc. Exp. Biol. Med., vol. 111, pp. 544 (1962).
Courtenay et al., Nature, vol. 283, pp. 666 (1980).
Swingle, Antiinflammatory Agents, Edited by Robert Scherrer and Michael Whitehouse, vol. II, Ch. 2, pp. 33–122 (1974).
Moran et al., J. Heterocyclic Chem., 23:1071 (1986).
Almstrom, Just. Lieb. Ann. Chem., 400;131 (1913) (English translation attached).
Knoevenagel, Chem. Ber., 21:1344 (1888) (English translation attached).
Kojima et al., Bull. Chem. Soc. Jpn., vol. 55, pp. 1454 (1982).
Khalifa, Arch. Pharm. (Weinheim), 323:883–885 (1990).
Ten Hoeve et al., Synthetic Communications, 24(15), 2215–2221 (1994).
Mitchell et al., Synthetic Communications, 25(8), 1231–1238 (1995).
Turck et al., Bull. Soc. Chim. Fr., 130:488–492 (1993) (English translation attached).
Ravina et al., Arch. Pharm. (Weinheim), 324:455–459 (1991).
Libermann et al., Soc. Chim. 117:5, pp. 1793–1798 (1959) (English translation attached).
Gabriel et al., Chem. Ber., 32:395 (1899) (English translation attached).
Freifelder et al., J. Am. Chem. Soc., vol. 82, pp. 696 (1959).
Curtius, J. Prakt. Chem., 50:508–530 (1894) (English translation attached).
Beyaert et al., EMBO Journal 1996, vol. 15, p 1914–23.
El–Rayyes and Al–Hajjar, J. Heterocycl. Chem. 21, 1473 (1984).
Joosten et al, Arthritis & Rheumatism 39:797–809 (1996).
Katritzky and Rachwal, J. Heterocyclic Chem. 32, 1007 (1995).
Lee et al, Circulatory Shock 44:97–103 (1995).
Simchen, G., Chem. Ber. 103, 389–397 (1970).

SUBSTITUTED PYRIDINE AND PYRIDAZINE COMPOUNDS AND METHODS OF USE

This application claims the benefit of U.S. Provisional Application No. 60/068,199 filed Dec. 19, 1997, which is hereby incorporated by reference.

BACKGROUND OF THE INVENTION

The present invention comprises a new class of substituted pyridine and pyridazine compounds useful in treating diseases, such as TNF-α, IL-1β, IL-6 and/or IL-8 mediated diseases and other maladies, such as pain, cancer, and diabetes. In particular, the compounds of the invention are useful for the prophylaxis and treatment of diseases or conditions involving inflammation. This invention also relates to intermediates and processes useful in the preparation of such compounds.

Interleukin-1 (IL-1) and Tumor Necrosis Factor α (TNF-α) are pro-inflammatory cytokines secreted by a variety of cells, including monocytes and macrophages, in response to many inflammatory stimuli (e.g., lipopolysaccharide—LPS) or external cellular stress (e.g., osmotic shock and peroxide).

Elevated levels of TNF-α and/or IL-1 over basal levels have been implicated in mediating or exacerbating a number of disease states including rheumatoid arthritis; Pagets disease; osteophorosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; Reiter's syndrome; type I and type II diabetes; bone resorption diseases; graft vs. host reaction; ischemia reperfusion injury; atherosclerosis; brain trauma; multiple sclerosis; cerebral malaria; sepsis; septic shock; toxic shock syndrome; fever, and myalgias due to infection. HIV-1, HIV-2, HIV-3, cytomegalovirus (CMV), influenza, adenovirus, the herpes viruses (including HSV-1, HSV-2), and herpes zoster are also exacerbated by TNF-α.

It has been reported that TNF-α plays a role in head trauma, stroke, and ischemia. For instance, in animal models of head trauma (rat), TNF-α levels increased in the contused hemisphere (Shohami et al., *J. Cereb. Blood Flow Metab.* 14, 615 (1994)). In a rat model of ischemia wherein the middle cerebral artery was occluded, the levels of TNF-α mRNA of TNF-α increased (Feurstein et al., *Neurosci. Lett.* 164, 125 (1993)). Administration of TNF-α into the rat cortex has been reported to result in significant neutrophil accumulation in capillaries and adherence in small blood vessels. TNF-α promotes the infiltration of other cytokines (IL-β, IL-6) and also chemokines, which promote neutrophil infiltration into the infarct area (Feurstein, *Stroke* 25, 1481 (1994)). TNF-α has also been implicated to play a role in type II diabetes (Endocrinol. 130, 43–52, 1994; and Endocrinol. 136, 1474–1481, 1995).

TNF-α appears to play a role in promoting certain viral life cycles and disease states associated with them. For instance, TNF-α secreted by monocytes induced elevated levels of HIV expression in a chronically infected T cell clone (Clouse et al., *J. Immunol.* 142, 431 (1989)). Lahdevirta et al., (*Am. J. Med.* 85, 289 (1988)) discussed the role of TNF-α in the HIV associated states of cachexia and muscle degradation.

TNF-α is upstream in the cytokine cascade of inflammation. As a result, elevated levels of TNF-α may lead to elevated levels of other inflammatory and proinflammatory cytokines, such as IL-1, IL-6, and IL-8.

Elevated levels of IL-1 over basal levels have been implicated in mediating or exacerbating a number of disease states including rheumatoid arthritis; osteoarthritis; rheumatoid spondylitis; gouty arthritis; Inflammatory bowel disease; adult respiratory distress syndrome (ARDS); psoriasis; Crohn's disease; ulcerative colitis; anaphylaxis; muscle degeneration; cachexia; Reiter's syndrome; type I and type II diabetes; bone resorption diseases; ischemia reperfusion injury; atherosclerosis; brain trauma; multiple sclerosis; sepsis; septic shock; and toxic shock syndrome. Viruses sensitive to TNF-α inhibition, e.g., HIV-1, HIV-2, HIV-3, are also affected by IL-1.

TNF-α and IL-1 appear to play a role in pancreatic β cell destruction and diabetes. Pancreatic β cells produce insulin which helps mediate blood glucose homeostasis. Deterioration of pancreatic β cells often accompanies type I diabetes. Pancreatic β cell functional abnormalities may occur in patients with type II diabetes. Type II diabetes is characterized by a functional resistance to insulin. Further, type II diabetes is also often accompanied by elevated levels of plasma glucagon and increased rates of hepatic glucose production. Glucagon is a regulatory hormone that attenuates liver gluconeogenesis inhibition by insulin. Glucagon receptors have been found in the liver, kidney and adipose tissue. Thus glucagon antagonists are useful for attenuating plasma glucose levels (WO 97/16442, incorporated herein by reference in its entirety). By antagonizing the glucagon receptors, it is thought that insulin responsiveness in the liver will improve, thereby decreasing gluconeogenesis and lowering the rate of hepatic glucose production.

In rheumatoid arthritis models in animals, multiple intra-articular injections of IL-1 have led to an acute and destructive form of arthritis (Chandrasekhar et al., *Clinical Immunol Immunopathol.* 55, 382 (1990)). In studies using cultured rheumatoid synovial cells, IL-1 is a more potent inducer of stromelysin than is TNF-α (Firestein, *Am. J. Pathol.* 140, 1309 (1992)). At sites of local injection, neutrophil, lymphocyte, and monocyte emigration has been observed. The emigration is attributed to the induction of chemokines (e.g., IL-8), and the up-regulation of adhesion molecules (Dinarello, *Eur. Cytokine Netw.* 5, 517–531 (1994)).

IL-1 also appears to play a role in promoting certain viral life cycles. For example, cytokine-induced increase of HIV expression in a chronically infected macrophage line has been associated with a concomitant and selective increase in IL-1 production (Folks et al., *J. Immunol.* 136, 40 (1986)). Beutler et al. (*J. Immunol.* 135, 3969 (1985)) discussed the role of IL-1 in cachexia. Baracos et al. (*New Eng. J. Med.* 308, 553 (1983)) discussed the role of IL-1 in muscle degeneration.

In rheumatoid arthritis, both IL-1 and TNF-α induce synoviocytes and chondrocytes to produce collagenase and neutral proteases, which leads to tissue destruction within the arthritic joints. In a model of arthritis (collagen-induced arthritis (CIA) in rats and mice), intra-articular administration of TNF-α either prior to or after the induction of CIA led to an accelerated onset of arthritis and a more severe course of the disease (Brahn et al., *Lymphokine Cytokine Res.* 11, 253 (1992); and Cooper, *Clin. Exp. Immunol.* 898, 244 (1992)).

IL-8 has been implicated in exacerbating and/or causing many disease states in which massive neutrophil infiltration into sites of inflammation or injury (e.g., ischemia) is mediated by the chemotactic nature of IL-8, including, but not limited to, the following: asthma, inflammatory bowel disease, psoriasis, adult respiratory distress syndrome, cardiac and renal reperfusion injury, thrombosis and glomerulonephritis. In addition to the chemotaxis effect on neutrophils, IL-8 also has the ability to activate neutrophils. Thus, reduction in IL-8 levels may lead to diminished neutrophil infiltration.

Several approaches have been taken to block the effect of TNF-α. One approach involves using soluble receptors for TNF-α (e.g., TNFR-55 or TNFR-75), which have demonstrated efficacy in animal models of TNF-α-mediated disease states. A second approach to neutralizing TNF-α using a monoclonal antibody specific to TNF-α, cA2, has demonstrated improvement in swollen joint count in a Phase II human trial of rheumatoid arthritis (Feldmann et al., *Immunological Reviews*, pp. 195–223 (1995)). These approaches block the effects of TNF-α and IL-1 by either protein sequestration or receptor antagonism.

GB 2,306,108, which is incorporated herein by reference in its entirety, describes imidazole derivatives which are Raf kinase antagonists useful in the treatment of cancer which is mediated by Raf and Raf-inducable proteins. Raf proteins are kinases activated in response to extracellular mitogenic stimuli such as PDGF, EGF, acidic FGF, thrombin, insulin or endothelin, and also in response to oncoproteins such as v-src, v-sis, and v-fms. Raf functions downstream of ras in signal transduction from the cellular membrane to the nucleus. Compounds may be oncolytics through the antagonism of Raf kinase. It has been reported that antisense constructs which reduce cellular levels of c-Raf and hence Raf activity inhibit the growth of rodent fibroblasts in soft agar, while exhibiting little or no general cytotoxicity. This inhibition of growth in soft agar is highly predictive of tumor responsiveness in whole animals. Moreover, Raf antisense constructs have shown efficacy in reducing tumor burden in animals. Examples of cancers where Raf kinase is implicated by overexpression include cancers of the brain, larynx, lung, lymphatic system, urinary tract and stomach, including hystocitic lymphoma, lung adenocarcinoma and small cell lung cancers. Other examples include cancers involving overexpression of upstream activators of Raf or Raf-activating oncogenes, including pancreatic and breast carcinoma.

GB 1,238,959 describes 3- or 4-(hetero)aryl substituted pyridine and pyridone compounds useful in the treatment of inflammation.

WO 98/03484 describes 2-(substituted phenyl or pyridinyl)-3-(4-(methylsulfonyl, aminosulfonyl, trifluorocarbonylaminosulfonyl or methylaminosulfonyl)phenyl-pyridine compounds useful in the treatment of COX-2 mediated diseases.

WO 96/24584 describes 2,3-di(hetero)aryl substituted pyridine compounds, wherein one of such (hetero)aryl substitutents is a phenyl radical substituted with an alkylsulfonyl, aminosulfonyl or haloalkylsulfonyl radical, useful as anti-inflammatory, analgesic and antipyretic agents.

BRIEF DESCRIPTION OF THE INVENTION

The present invention comprises a new class of compounds useful in the prophylaxis and treatment of diseases, such as TNF-α, IL-1β, IL-6 and/or IL-8 mediated diseases and other maladies, such as pain, cancer and diabetes. In particular, the compounds of the invention are useful for the prophylaxis and treatment of diseases or conditions involving inflammation. Accordingly, the invention also comprises pharmaceutical compositions comprising the compounds, methods for the prophylaxis and treatment of TNF-α, IL-1β, IL-6 and/or IL-8 mediated diseases, such as inflammatory, pain and diabetes diseases, using the compounds and compositions of the invention, and intermediates and processes useful for the preparation of the compounds of the invention.

The compounds of the invention are represented by the following general structure:

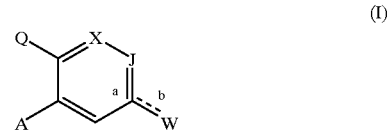

(I)

wherein A, Q, X, J, W, a, and b are defined below.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In accordance with the present invention, there is provided compounds of formula I:

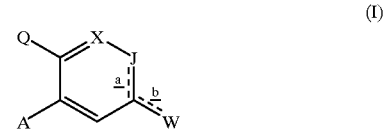

(I)

or a pharmaceutically acceptable salt thereof, wherein
W is $R_1$, $R_2$, O or N—$R_3$;
A and Q are each independently $R_{11}$ or $R_{12}$;
X is N or C—H;
J is N—$R_3$, N, C—$R_1$ or C—$R_2$, provided at least one of X or J is N or N—$R_3$; and
when W is $R_1$, then a is a double bond, b is a single bond and J is other than N—$R_3$ or C—$R_1$; when W is $R_2$, then a is a double bond, b is a single bond and J is other than N—$R_3$ or C—$R_2$; and when W is O or N—$R_3$, then a is a single bond, b is a double bond and J is N—$R_3$;
Preferably,
W is Rhd 1, $R_2$, O or N—$R_3$;
A is $R_{11}$ and Q is $R_{12}$, or A is $R_{12}$ and Q is $R_{11}$;
X is N or C—H;
J is N—$R_3$, N, C—$R_1$ or C—$R_2$, provided at least one of X or J is N or N—$R_3$; and
when W is $R_1$, then a is a double bond, b is a single bond and J is other than N—$R_3$ or C—$R_1$; when W is $R_2$, then a is a double bond, b is a single bond and J is other than N—$R_3$ or C—$R_2$; and when W is O or N—$R_3$, then a is a single bond, b is a double bond and J is N—$R_3$;
More preferably,
W is $R_1$, $R_2$ or O;
A is $R_{11}$ and Q is $R_{12}$, or A is $R_{12}$ and Q is $R_{11}$;
X is N or C—H;
J is N—$R_3$, N, C—$R_1$ or C—$R_2$, provided at least one of X or J is N or N—$R_3$; and
when W is $R_1$; then a is a double bond, b is a single bond and J is other than N—$R_3$ or C—$R_1$; when W is $R_2$, then a is a double bond, b is a single bond and J is other than N—$R_3$ or C—$R_2$; and when W is O or N—$R_3$, then a is a single bond, b is a double bond and J is N—$R_3$;
More preferably,
W is $R_1$ or $R_2$;
A is $R_{11}$ and Q is $R_{12}$, or A is $R_{12}$ and Q is $R_{11}$;
X is N or C—H;
J is N, C—$R_1$ or C—$R_2$, provided at least one of X or J is N;
a is a double bond and b is a single bond; and
when W is $R_1$, then J is other than C—$R_1$; when W is $R_2$, then C—$R_2$;
Most preferably,
W is $R_1$;
A is $R_{12}$ and Q is $R_{11}$;
X is N and J is C—$R_2$, or X is C—H and J is N, or X and J are both N; and
a is a double bond and b is a single bond; or
alternatively,
W is $R_2$;
A is $R_{11}$ and Q is $R_{12}$;
X is N and J is C—$R_1$; and
a is a double bond and b is a single bond;
Alternatively more preferably,
W is O;
A is $R_{11}$ and Q is $R_{12}$, or A is $R_{12}$ and Q is $R_{11}$;
X is N or C—H;
J is N—$R_3$; and
a is a single bond and b is a double bond;
More preferably,
W is O;
A is $R_{11}$ and Q is $R_{12}$;
X is N or C—H;
J is N—$R_3$; and
a is a single bond and b is a double bond;
Most preferably,
W is O;
A is $R_{11}$ and Q is $R_{12}$;
X is C—H;
J is N—$R_3$; and
a is a single bond and b is a double bond;
$R_1$ is —Z—Y or —Y; and each $R_3$ is independently a hydrogen radical or —Z—Y; provided that the total number of aryl, heteroaryl, cycloalkyl and heterocyclyl radicals in $R_1$, $R_2$ and $R_3$ is 0–3; and preferably, 0–2;
$R_2$ is (1) a hydrogen, halo, trifluoromethyl, cyano, —C(O)—$OR_{21}$ or —C(O)—$NR_5R_{21}$ radical;
(2) alkyl radical optionally substituted by (a) 1–2 radicals of amino, alkylamino, dialkylamino, alkanoylamino, alkoxycarbonylamino, alkylsulfonylamino, hydroxy, alkoxy or alkylthio, and (b) a radical of heterocyclyl, aryl or heteroaryl optionally substituted by 1–3 radicals of amino, alkylamino, dialkylamino, alkanoylamino, alkoxycarbonylamino, alkylsulfonylamino, hydroxy, alkoxy, alkylthio, halo, alkyl, carboxy, carboxamide, trifluoromethoxy or trifluoromethyl radicals; or
(3) aryl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl, carboxy, carboxamide, trifluoromethoxy or trifluoromethyl radicals;
preferably, $R_2$ is (1) a hydrogen, halo, trifluoromethyl, cyano, —C(O)—$OR_{21}$ or —C(O)—$NR_5R_{21}$ radical;
(2) $C_1$–$C_8$ alkyl radical optionally substituted by (a) 1–2 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy or $C_1$–$C_4$ alkylthio, and (b) a radical of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, halo, $C_1$–$C_4$ alkyl, carboxy, carboxamide, trifluoromethoxy or trifluoromethyl radicals; or
(3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, carboxy, carboxamide, trifluoromethoxy or trifluoromethyl radicals;
more preferably, $R_2$ is (1) a hydrogen, halo, trifluoromethyl, cyano, carboxy or carboxamide radical;
(2) $C_1$–$C_8$ alkyl radical optionally substituted by (a) 1–2 radicals of amino, $C_1$–$C_4$ alkylamino, di-($C_1$–$C_4$ alkyl) amino, hydroxy, $C_1$–$C_4$ alkoxy or $C_1$–$C_4$ alkylthio; or
(3) aryl or heteroaryl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, carboxy, carboxamide, trifluoromethoxy or trifluoromethyl radicals;
more preferably, $R_2$ is (1) a hydrogen, halo, trifluoromethyl or cyano radical; or
(2) $C_1$–$C_4$ alkyl radical optionally substituted by (a) 1–2 radicals of amino, $C_1$–$C_4$ alkylamino or di-($C_1$–$C_4$ alkyl) amino; or
most preferably, $R_2$ is a hydrogen, halo, trifluoromethyl, cyano or $C_1$–$C_4$ alkyl radical;
Z is independently a
(1) alkyl, alkenyl or alkynyl radical optionally substituted by (a) 1–3 radicals of amino, alkylamino, dialkylamino, alkanoylamino, alkoxycarbonylamino, alkylsulfonylamino, hydroxy, alkoxy, alkylthio or halo, and (b) 1–2 radicals of heterocyclyl, aryl or heteroaryl; or
(2) heterocyclyl, aryl or heteroaryl radical; wherein the heterocyclyl radicals are optionally substituted by 1–3 radicals of amino, alkylamino, dialkylamino, alkanoylamino, alkoxycarbonylamino, alkylsulfonylamino, hydroxy, alkoxy, alkylthio, alkyl, arylalkyl, heteroarylalkyl or haloalkyl; and the aryl and heteroaryl radicals are optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl or haloalkyl;
preferably, each Z is independently a
(1) $C_1$–$C_8$ alkyl, $C_2$–$C_8$ alkenyl or $C_2$–$C_8$ alkynyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio or halo, and (b) 1–2 radicals of heterocyclyl, aryl or heteroaryl; or
(2) heterocyclyl, aryl or heteroaryl radical; wherein the heterocyclyl radicals are optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, $C_1$–$C_4$ alkyl, aryl-$C_1$–$C_4$ alkyl, heteroaryl-$C_1$–$C_4$ alkyl or $C_1$–$C_4$ haloalkyl of 1–3 halo radicals; and the aryl and heteroaryl radicals are optionally substituted by 1–3 radicals of amino, $C_1$–$C_4$ alkylamino, di-($C_1$-$C_4$ alkyl)amino, $C_1$-$C_5$ alkanoylamino, ($C_1$-$C_4$ alkoxy)carbonylamino, $C_1$-$C_4$ alkylsulfonylamino, hydroxy, $C_1$-$C_4$ alkoxy, $C_1$-$C_4$ alkylthio, cyano, halo, $C_1$-$C_4$ alkyl or $C_1$-$C_4$ haloalkyl of 1–3 halo radicals;

more preferably, each Z is independently a
(1) $C_1$-$C_8$ alkyl or $C_2$-$C_8$ alkenyl radical optionally substituted by (a) 1–3 radicals of amino, $C_1$-$C_4$ alkylamino, di-($C_1$-$C_4$ alkyl)amino, $C_1$-$C_5$ alkanoylamino, ($C_1$-$C_4$ alkoxy)carbonylamino, hydroxy, $C_1$-$C_4$ alkoxy, $C_1$-$C_4$ alkylthio or halo, and (b) 1–2 radicals of heterocyclyl, aryl or heteroaryl; or
(2) heterocyclyl, aryl or heteroaryl radical; wherein the heterocyclyl radicals are optionally substituted by 1–3 radicals of amino, $C_1$-$C_4$ alkylamino, di-($C_1$-$C_4$ alkyl) amino, $C_1$-$C_5$ alkanoylamino, ($C_1$-$C_4$ alkoxy) carbonylamino, hydroxy, $C_1$-$C_4$ alkoxy, $C_1$-$C_4$ alkylthio, $C_1$-$C_4$ alkyl, aryl-$C_1$-$C_4$ alkyl, heteroaryl-$C_1$-$C_4$ alkyl or $C_1$-$C_2$ haloalkyl of 1–3 halo radicals; and the aryl and heteroaryl radicals are optionally substituted by 1–3 radicals of amino, $C_1$-$C_4$ alkylamino, di-($C_1$-$C_4$ alkyl)amino, $C_1$-$C_5$ alkanoylamino, ($C_1$-$C_4$ alkoxy)carbonylamino, hydroxy, $C_1$-$C_4$ alkoxy, $C_1$-$C_4$ alkylthio, cyano, halo, $C_1$-$C_4$ alkyl or $C_1$-$C_2$ haloalkyl of 1–3 halo radicals;

more preferably, each Z is independently a
(1) $C_1$-$C_4$ alkyl or $C_2$-$C_5$ alkenyl radical optionally substituted by (a) 1–3 radicals of amino, di-($C_1$-$C_2$ alkyl) amino, $C_1$-$C_5$ alkanoylamino, ($C_1$-$C_4$ alkoxy) carbonylamino, hydroxy, $C_1$-$C_2$ alkoxy, $C_1$-$C_2$ alkylthio or halo, and (b) 1–2 radicals of heterocyclyl, aryl or heteroaryl; or
(2) heterocyclyl, aryl or heteroaryl radical; wherein the heterocyclyl radicals are optionally substituted by 1–3 radicals of amino, di-($C_1$-$C_2$ alkyl)amino, $C_1$-$C_5$ alkanoylamino, ($C_1$-$C_4$ alkoxy)carbonylamino, hydroxy, $C_1$-$C_4$ alkoxy, $C_1$-$C_4$ alkylthio, $C_1$-$C_4$ alkyl, aryl-$C_1$-$C_4$ alkyl, heteroaryl-$C_1$-$C_4$ alkyl or trifluoromethyl radicals; and the aryl and heteroaryl radicals are optionally substituted by 1–3 radicals of amino, di-($C_1$-$C_2$ alkyl)amino, $C_1$-$C_5$ alkanoylamino, ($C_1$-$C_4$ alkoxy)carbonylamino, hydroxy, $C_1$-$C_4$ alkoxy, $C_1$-$C_4$ alkylthio, cyano, halo, $C_1$-$C_4$ alkyl or trifluoromethyl radicals;

more preferably, each Z is independently a
(1) $C_1$-$C_4$ alkyl or $C_2$-$C_5$ alkenyl radical optionally substituted by (a) 1–3 radicals of amino, di-($C_1$-$C_2$ alkyl) amino, ($C_1$-$C_4$ alkoxy)carbonylamino, hydroxy, $C_1$-$C_2$ alkoxy, $C_1$-$C_2$ alkylthio or halo, and (b) 1–2 radicals of aryl or heteroaryl; or
(2) heterocyclyl, aryl or heteroaryl radical; wherein the heterocyclyl radicals are optionally substituted by 1–2 radicals of $C_1$-$C_4$ alkyl or aryl-$C_1$-$C_2$ alkyl radicals; and the aryl and heteroaryl radicals are optionally substituted by 1–3 radicals of amino, di-($C_1$-$C_2$ alkyl)amino, acetamido, ($C_1$-$C_4$ alkoxy)carbonylamino, hydroxy, $C_1$-$C_2$ alkoxy, $C_1$-$C_2$ alkylthio, cyano, halo, $C_1$-$C_4$ alkyl or trifluoromethyl radicals;

more preferably, each Z is independently a
(1) $C_1$-$C_4$ alkyl radical optionally substituted by (a) 1–2 radicals of amino, di-($C_1$-$C_2$ alkyl)amino, hydroxy, $C_1$-$C_2$ alkoxy or $C_1$-$C_2$ alkylthio, and (b) an aryl radical; or
(2) a heterocyclyl radical optionally substituted by 1–2 radicals of $C_1$-$C_2$ alkyl or aryl-$C_1$-$C_2$ alkyl radicals; wherein the aryl radicals are optionally substituted by 1–2 radicals of amino, di-($C_1$-$C_2$ alkyl)amino, hydroxy, $C_1$-$C_2$ alkoxy, $C_1$-$C_2$ alkylthio, cyano, halo, $C_1$-$C_2$ alkyl or trifluoromethyl radicals; and most preferably, each Z is independently a
(1) $C_1$-$C_4$ alkyl radical optionally substituted by 1–2 radicals of amino, dimethylamino or phenyl radical; or
(2) a heterocyclyl radical optionally substituted by 1–2 radicals of methyl or phenylmethyl; wherein the phenyl radicals are optionally substituted by 1–2 radicals of amino, di-($C_1$-$C_2$ alkyl)amino, hydroxy, $C_1$-$C_2$ alkoxy, $C_1$-$C_2$ alkylthio, cyano, halo, $C_1$-$C_2$ alkyl or trifluoromethyl radicals;

each Y is independently a
(1) hydrogen radical;
(2) halo or nitro radical;
(3) —C(O)—$R_{20}$, —C(O)—$OR_{21}$, —C(O)—$NR_5R_{21}$ or —C($NR_5$)—$NR_5R_{21}$ radical;
(4) —$OR_{21}$, —O—C(O)—$R_{21}$, —O—C(O)—$NR_5R_{21}$ or —O—C(O)—$NR_{22}$—S(O)$_2$—$R_{20}$ radical;
(5) —$SR_{21}$, —S(O)—$R_{20}$, —S(O)$_2$—$R_{20}$, —S(O)$_2$—$NR_5R_{21}$, —S(O)$_2$13 $NR_{22}$—C(O)—$R_{21}$, —S(O)$_2$—$NR_{22}$—C(O)—$OR_{20}$ or —S(O)$_2$—$NR_{22}$—C(O)—$NR_5R_{21}$ radical; or
(6) —$NR_5R_{21}$, —$NR_{22}$—C(O)—$R_{21}$, —$NR_{22}$—C(O)—$OR_{20}$, —$NR_{22}$—C(O)—$NR_5R_{21}$, —$NR_{22}$—C($NR_5$)—$NR_5R_{21}$, —$NR_{22}$—S(O)$_2$—$R_{20}$ or —$NR_{22}$—S(O)$_2$—$NR_5R_{21}$ radical;

preferably, each Y is independently a
(1) hydrogen or halo radical;
(2) —C(O)—$R_{20}$, —C(O)—$OR_{21}$, —C(O)—$NR_5R_{21}$ or —C($NR_5$)—$NR_5R_{21}$ radical;
(3) —$OR_{21}$, —O—C(O)—$R_{21}$ or —O—C(O)—$NR_5R_{21}$ radical;
(4) —$SR_{21}$, —S(O)—$R_{20}$, —S(O)$_2$—$R_{20}$ or —S(O)$_2$—$NR_5R_{21}$ radical; or
(5) —$NR_5R_{21}$, —$NR_{22}$—C(O)—$R_{21}$, —$NR_{22}$—C(O)—$OR_{20}$ or —$NR_{22}$—C(O)—$NR_5R_{21}$ radical;

more preferably, each Y is independently a
(1) hydrogen radical;
(2) —C(O)—$R_{20}$ or —C(O)—$NR_5R_{21}$ radical;
(3) —$OR_{21}$, —$SR_{21}$, —S(O)—$R_{20}$, —S(O)$_2$—$R_{20}$ or —S(O)$_2$—$NR_5R_{21}$ radical; or
(4) —$NR_5R_{21}$ or —$NR_{22}$—C(O)—$R_{21}$ radical;

more preferably, each Y is independently a hydrogen, —$OR_{21}$, —$SR_{21}$, —S(O)—$R_{20}$, —S(O)$_2$—$R_{20}$ or —$NR_5R_{21}$ radical;

most preferably, each Y is independently a —$OR_{21}$, —$SR_{21}$ or —$NR_5R_{21}$ radical;

wherein each $R_5$ is independently
(1) hydrogen radicals;
(2) alkyl, alkenyl or alkynyl radicals optionally substituted by 1–3 radicals of amino, alkylamino, dialkylamino, hydroxy, alkoxy, alkylthio, —$SO_3H$ or halo; or
(3) aryl, heteroaryl, aralkyl, heteroaralkyl, heterocyclyl, heterocyclylalkyl, cycloalkyl or cycloalkylalkyl radicals optionally substituted by 1–3 radicals of amino, alkylamino, dialkylamino, hydroxy, alkoxy, alkylthio, alkyl or haloalkyl;

preferably, each $R_5$ is independently
(1) hydrogen radicals;
(2) $C_1$-$C_8$ alkyl, $C_2$-$C_8$ alkenyl or $C_2$-$C_8$ alkynyl radicals optionally substituted by 1–3 radicals of amino, $C_1$-$C_4$ alkylamino, di-($C_1$-$C_4$-alkyl)amino, hydroxy, $C_1$-$C_4$ alkoxy, $C_1$-$C_4$ alkylthio, —$SO_3H$ or halo; or
(3) aryl, heteroaryl, aryl-$C_1$-$C_4$-alkyl, heteroaryl-$C_1$-$C_4$-alkyl, heterocyclyl, heterocyclyl-$C_1$-$C_4$-alkyl, $C_3$-$C_8$ cycloalkyl or $C_3$-$C_8$-cycloalkyl-$C_1$-$C_4$-alkyl radicals optionally substituted by 1–3 radicals of amino, $C_1$-$C_4$ alkylamino, di-($C_1$-$C_4$-alkyl)amino, hydroxy, $C_1$-$C_4$ alkoxy, $C_1$-$C_4$ alkylthio, $C_1$-$C_4$ alkyl or $C_1$-$C_4$ haloalkyl of 1–3 halo radicals;

more preferably, each $R_5$ is independently
(1) hydrogen radicals;
(2) $C_1-C_4$ alkyl, $C_2-C_5$ alkenyl or $C_2-C_5$ alkynyl radicals optionally substituted by 1–3 radicals of amino, $C_1-C_4$ alkylamino, di-($C_1-C_4$-alkyl)amino, hydroxy, $C_1-C_4$ alkoxy, $C_1-C_4$ alkylthio, —$SO_3H$ or halo; or
(3) aryl, heteroaryl, aryl-$C_1-C_4$-alkyl, heteroaryl-$C_1-C_4$-alkyl, heterocyclyl, heterocyclyl-$C_1-C_4$-alkyl, $C_3-C_8$ cycloalkyl or $C_3-C_8$-cycloalkyl-$C_1-C_4$-alkyl radicals optionally substituted by 1–3 radicals of amino, $C_1-C_4$ alkylamino, di-($C_1-C_4$-alkyl)amino, hydroxy, $C_1-C_4$ alkoxy, $C_1-C_4$ alkylthio, $C_1-C_4$ alkyl or $C_1-C_4$ haloalkyl of 1–3 halo radicals;
more preferably, each $R_5$ is independently
(1) hydrogen radicals;
(2) $C_1-C_4$ alkyl or $C_2-C_5$ alkenyl radicals optionally substituted by 1–3 radicals of amino, di-($C_1-C_4$-alkyl)amino, hydroxy, $C_1-C_4$ alkoxy, $C_1-C_4$ alkylthio, —$SO_3H$ or halo; or
(3) phenyl-$C_1-C_2$-alkyl, heteroaryl-$C_1-C_2$-alkyl, heterocyclyl-$C_1-C_2$-alkyl or $C_3-C_6$-cycloalkyl-$C_1-C_2$-alkyl radicals optionally substituted by 1–3 radicals of amino, di-($C_1-C_4$-alkyl)amino, hydroxy, $C_1-C_4$ alkoxy, $C_1-C_4$ alkylthio, $C_1-C_4$ alkyl or $C_1-C_2$ haloalkyl of 1–3 halo radicals;
more preferably, each $R_5$ is independently
(1) hydrogen radical;
(2) $C_1-C_4$ alkyl radical optionally substituted by 1–3 radicals of amino, di-($C_1-C_2$-alkyl)amino, hydroxy, $C_1-C_2$ alkoxy, $C_1-C_2$ alkylthio or halo; or
(3) phenyl-$C_1-C_2$-alkyl, heteroaryl-$C_1-C_2$-alkyl, heterocyclyl-$C_1-C_2$-alkyl or $C_3-C_6$-cycloalkyl-$C_1-C_2$-alkyl radicals optionally substituted by 1–3 radicals of amino, di-($C_1-C_2$-alkyl)amino, hydroxy, $C_1-C_2$ alkoxy, $C_1-C_2$ alkylthio, methoxy, methylthio, $C_1-C_4$ alkyl or trifluoromethyl radicals;
more preferably, each $R_5$ is independently
(1) hydrogen radical;
(2) $C_1-C_4$ alkyl radical optionally substituted by 1–3 halo radicals; or
(3) phenyl-$C_1-C_2$-alkyl or heteroaryl-$C_1-C_2$-alkyl, radicals optionally substituted by 1–3 radicals of amino, dimethylamino, hydroxy, methoxy, methylthio, methyl or trifluoromethyl radicals;
more preferably, each $R_5$ is independently hydrogen or $C_1-C_4$ alkyl radical; and most preferably, each $R_5$ is a hydrogen or methyl radical;
wherein each $R_{20}$ is independently
(1) alkyl, alkenyl or alkynyl radicals optionally substituted by 1–3 radicals of amino, alkylamino, dialkylamino, alkanoylamino, alkoxycarbonylamino, N-(alkoxycarbonyl)-N-(alkyl)amino, aminocarbonylamino, alkylsulfonylamino, hydroxy, alkoxy, alkylthio, alkylsulfinyl, alkylsulfonyl, halo or aralkoxy, aralkylthio, aralkylsulfonyl, cycloalkyl, heterocyclyl, aryl or heteroaryl radicals optionally substituted by 1–3 radicals of amino, alkylamino, dialkylamino, alkanoylamino, alkoxycarbonylamino, alkylsulfonylamino, alkanoyl, hydroxy, alkoxy, alkylthio, alkylsulfinyl, alkylsulfonyl, halo, alkyl or haloalkyl;
(2) heterocyclyl radical optionally substituted by 1–3 radicals of amino, alkylamino, dialkylamino, alkanoylamino, alkoxycarbonylamino, alkylsulfonylamino, hydroxy, alkoxy, alkylthio, alkyl or haloalkyl; or
(3) aryl or heteroaryl radicals optionally substituted by 1–3 radicals of amino, alkylamino, dialkylamino, alkanoylamino, alkoxycarbonylamino, alkylsulfonylamino, alkoxycarbonyl, hydroxy, alkoxy, alkylthio, cyano, halo, azido, alkyl or haloalkyl;
preferably, each $R_{20}$ is independently
(1) $C_1-C_8$ alkyl, $C_2-C_8$ alkenyl or $C_2-C_8$ alkynyl radicals optionally substituted by 1–3 radicals of amino, $C_1-C_4$ alkylamino, di-($C_1-C_4$ alkyl)amino, $C_1-C_5$ alkanoylamino, ($C_1-C_4$ alkoxy)carbonylamino, N-(($C_1-C_4$ alkoxy)carbonyl)-N-($C_1-C_4$ alkyl)amino, aminocarbonylamino, $C_1-C_4$ alkylsulfonylamino, hydroxy, $C_1-C_4$ alkoxy, $C_1-C_4$ alkylthio, $C_1-C_4$ alkylsulfinyl, $C_1-C_4$ alkylsulfonyl, halo or aryl-$C_1-C_4$-alkoxy, aryl-$C_1-C_4$-alkylthio, aryl-$C_1-C_4$-alkylsulfonyl, $C_3-C_8$ cycloalkyl, heterocyclyl, aryl or heteroaryl radicals optionally substituted by 1–3 radicals of amino, $C_1-C_4$ alkylamino, di-($C_1-C_4$ alkyl)amino, $C_1-C_5$ alkanoylamino, ($C_1-C_4$ alkoxy)carbonylamino, $C_1-C_4$ alkylsulfonylamino, $C_1-C_5$ alkanoyl, hydroxy, $C_1-C_4$ alkoxy, $C_1-C_4$ alkylthio, $C_1-C_4$ alkylsulfinyl, $C_1-C_4$ alkylsulfonyl, halo, $C_1-C_4$ alkyl or $C_1-C_4$ haloalkyl of 1–3 halo radicals;
(2) heterocyclyl radical optionally substituted by 1–3 radicals of amino, $C_1-C_4$ alkylamino, di-($C_1-C_4$ alkyl)amino, $C_1-C_5$ alkanoylamino, ($C_1-C_4$ alkoxy)carbonylamino, $C_1-C_4$ alkylsulfonylamino, hydroxy, $C_1-C_4$ alkoxy, $C_1-C_4$ alkylthio, $C_1-C_4$ alkyl or $C_1-C_4$ haloalkyl of 1–3 halo radicals; or
(3) aryl or heteroaryl radicals optionally substituted by 1–3 radicals of amino, $C_1-C_4$ alkylamino, di-($C_1-C_4$ alkyl) amino, $C_1-C_5$ alkanoylamino, ($C_1-C_4$ alkoxy) carbonylamino, $C_1-C_4$ alkylsulfonylamino, ($C_1-C_4$ alkoxy)carbonyl, hydroxy, $C_1-C_4$ alkoxy, $C_1-C_4$ alkylthio, cyano, halo, azido, $C_1-C_4$ alkyl or $C_1-C_4$ haloalkyl of 1–3 halo radicals;
more preferably, each $R_{20}$ is independently
(1) $C_1-C_8$ alkyl, $C_2-C_5$ alkenyl or $C_2-C_5$ alkynyl radicals optionally substituted by 1–3 radicals of amino, $C_1-C_4$ alkylamino, di-($C_1-C_4$ alkyl)amino, $C_1-C_5$ alkanoylamino, ($C_1-C_4$ alkoxy)carbonylamino, N-(($C_1-C_4$ alkoxy)carbonyl)-N-($C_1-C_4$ alkyl)amino, aminocarbonylamino, $C_1-C_4$ alkylsulfonylamino, hydroxy, $C_1-C_4$ alkoxy, $C_1-C_4$ alkylthio, $C_1-C_4$ alkylsulfinyl, $C_1-C_4$ alkylsulfonyl, halo or aryl-$C_1-C_4$-alkoxy, aryl-$C_1-C_4$-alkylthio, aryl-$C_1-C_4$-alkylsulfonyl, $C_3-C_8$ cycloalkyl, heterocyclyl, aryl or heteroaryl radicals optionally substituted by 1–3 radicals of amino, $C_1-C_4$ alkylamino, di-($C_1-C_4$ alkyl)amino, $C_1-C_5$ alkanoylamino, ($C_1-C_4$ alkoxy)carbonylamino, $C_1-C_4$ alkylsulfonylamino, $C_1-C_5$ alkanoyl, hydroxy, $C_1-C_4$ alkoxy, $C_1-C_4$ alkylthio, $C_1-C_4$ alkylsulfinyl, $C_1-C_4$ alkylsulfonyl, halo, $C_1-C_4$ alkyl or $C_1-C_4$ haloalkyl of 1–3 halo radicals;
(2) heterocyclyl radical optionally substituted by 1–3 radicals of amino, $C_1-C_4$ alkylamino, di-($C_1-C_4$ alkyl)amino, $C_1-C_5$ alkanoylamino, ($C_1-C_4$ alkoxy)carbonylamino, $C_1-C_4$ alkylsulfonylamino, hydroxy, $C_1-C_4$ alkoxy, $C_1-C_4$ alkylthio, $C_1-C_4$ alkyl or $C_1-C_4$ haloalkyl of 1–3 halo radicals; or
(3) aryl or heteroaryl radicals optionally substituted by 1–3 radicals of amino, $C_1-C_4$ alkylamino, di-($C_1-C_4$ alkyl) amino, $C_1-C_5$ alkanoylamino, ($C_1-C_4$ alkoxy) carbonylamino, $C_1-C_4$ alkylsulfonylamino, ($C_1-C_4$ alkoxy)carbonyl, hydroxy, $C_1-C_4$ alkoxy, $C_1-C_4$ alkylthio, cyano, halo, azido, $C_1-C_4$ alkyl or $C_1-C_4$ haloalkyl of 1–3 halo radicals;
more preferably, each $R_{20}$ is independently
(1) $C_1-C_8$ alkyl or $C_2-C_5$ alkenyl radicals optionally substituted by 1–3 radicals of amino, $C_1-C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo or aryl-$C_1$–$C_4$-alkoxy, aryl-$C_1$–$C_4$-alkylthio, aryl-$C_1$–$C_4$-alkylsulfonyl, $C_3$–$C_6$ cycloalkyl, heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, hydroxy, $C_1$–$C_4$ alkoxy, $C_1$–$C_4$ alkylthio, halo, $C_1$–$C_4$ alkyl or $C_1$–$C_2$ haloalkyl of 1–3 halo radicals;
(2) heterocyclyl radical optionally substituted by 1–2 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio or $C_1$–$C_4$ alkyl; or
(3) aryl or heteroaryl radicals optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or $C_1$–$C_2$ haloalkyl of 1–3 halo radicals;
more preferably, each $R_{20}$ is independently
(1) $C_1$–$C_8$ alkyl or $C_2$–$C_5$ alkenyl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo or aryl-$C_1$–$C_4$-alkoxy, aryl-$C_1$–$C_4$-alkylthio, aryl-$C_1$–$C_4$-alkylsulfonyl, $C_3$–$C_6$ cycloalkyl, heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, hydroxy, $C_1$–$C_4$ alkoxy, $C_1$–$C_4$ alkylthio, halo, $C_1$–$C_4$ alkyl or $C_1$–$C_2$ haloalkyl of 1–3 halo radicals;
(2) heterocyclyl radical optionally substituted by 1–2 radicals of amino, di-($C_1$–$C_4$ alkyl)amino, ($C_1$–$C_4$ alkoxy) carbonylamino, hydroxy, $C_1$–$C_4$ alkoxy, $C_1$–$C_4$ alkylthio or $C_1$–$C_4$ alkyl; or
(3) aryl or heteroaryl radicals optionally substituted by 1–2 radicals of amino, $C_1$–$C_4$ alkylamino, di-($C_1$–$C_4$ alkyl) amino, acetamido, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or trifluoromethyl radicals;
more preferably, each $R_{20}$ is independently
(1) $C_1$–$C_8$ alkyl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo or $C_3$–$C_6$ cycloalkyl, heterocyclyl, aryl or heteroaryl radicals optionally substituted by 1–2 radicals of amino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, halo, $C_1$–$C_4$ alkyl or trifluoromethyl radicals;
(2) heterocyclyl radical optionally substituted by 1–2 radicals of hydroxy, $C_1$–$C_4$ alkoxy, $C_1$–$C_4$ alkylthio or $C_1$–$C_4$ alkyl; or
(3) aryl or heteroaryl radicals optionally substituted by 1–2 radicals of ($C_1$–$C_4$ alkoxy)carbonyl, amino, $C_1$–$C_4$ alkylamino, di-($C_1$–$C_4$ alkyl)amino, hydroxy, $C_1$–$C_4$ alkoxy, $C_1$–$C_4$ alkylthio, cyano, halo, azido, $C_1$–$C_4$ alkyl or trifluoromethyl radicals;
more preferably, each $R_{20}$ is independently
(1) $C_1$–$C_6$ alkyl radicals optionally substituted by 1–3 radicals of amino, methylamino, dimethylamino, t-butoxycarbonylamino, N-((t-butoxy)carbonyl)-N-(methyl)amino, aminocarbonylamino, hydroxy, butoxy, methoxy, butylthio, methylthio, methylsulfinyl, methylsulfonyl, halo or $C_5$–$C_6$ cycloalkyl, heterocyclyl, phenyl or heteroaryl radicals optionally substituted by 1–2 radicals of amino, dimethylamino, acetamino, hydroxy, methoxy, methylthio, halo, methyl or trifluoromethyl radicals;
(2) heterocyclyl radical optionally substituted by 1–2 radicals of hydroxy or $C_1$–$C_4$ alkyl; or
(3) aryl or heteroaryl radicals optionally substituted by 1–2 radicals of amino, dimethylamino, hydroxy, methoxy, methylthio, halo, methyl or trifluoromethyl radicals;
more preferably, each $R_{20}$ is independently
(1) $C_1$–$C_6$ alkyl radicals optionally substituted by 1–3 radicals of amino, methylamino, dimethylamino, t-butoxycarbonylamino, N-((t-butoxy)carbonyl)-N-(methyl)amino, aminocarbonylamino, hydroxy, butoxy, methoxy, butylthio, methylthio, methylsulfinyl, methylsulfonyl, halo or $C_5$–$C_6$ cycloalkyl, heterocyclyl, phenyl or heteroaryl radicals optionally substituted by 1–2 radicals of amino, dimethylamino, acetamino, hydroxy, methoxy, methylthio, halo, methyl or trifluoromethyl radicals;
(2) heterocyclyl radical; or
(3) aryl or heteroaryl radicals optionally substituted by 1–2 radicals of amino, dimethylamino, hydroxy, methoxy, methylthio, halo, methyl or trifluoromethyl radicals; most preferably, each $R_{20}$ is independently
(1) $C_1$–$C_6$ alkyl radicals optionally substituted by 1–3 radicals of amino, methylamino, dimethylamino, hydroxy or phenyl or heteroaryl radicals optionally substituted by 1–2 radicals of amino, dimethylamino, hydroxy, methoxy, methylthio, halo, methyl or trifluoromethyl radicals;
(2) heterocyclyl radical; or
(3) aryl or heteroaryl radicals optionally substituted by 1–2 radicals of amino, dimethylamino, hydroxy, methoxy, methylthio, halo, methyl or trifluoromethyl radicals;
each $R_{21}$ is independently hydrogen radical or $R_{20}$;
each $R_{22}$ is independently
(1) hydrogen radical;
(2) alkyl radical optionally substituted by a radical of heterocyclyl, aryl or heteroaryl optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl; or
(3) heterocyclyl, aryl or heteroaryl radicals optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl;
preferably, each $R_{22}$ is independently
(1) hydrogen radical;
(2) $C_1$–$C_4$ alkyl radical optionally substituted by a radical of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, (Ci—$C_4$ alkoxy) carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals; or (3) heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals;

more preferably, each $R_{22}$ is independently (1) hydrogen radical; or (2) $C_1$–$C_4$ alkyl radical optionally substituted by a radical of phenyl or heteroaryl optionally substituted by 1–3 radicals of amino, di-($C_1$–$C_2$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;

more preferably, each $R_{22}$ is independently hydrogen or $C_1$–$C_4$ alkyl radical; and most preferably, each $R_{22}$ is independently hydrogen or methyl radical;

$R_{11}$ is an aryl or heteroaryl radical other than an "N"-heteroaryl radical, and $R_{12}$ is an "N"-heteroaryl radical, wherein the aryl, heteroaryl and "N"-heteroaryl radicals are optionally substituted by 1–3 radicals of (1) $R_{30}$;

(2) halo or cyano radicals;

(3) —C(O)—$R_{30}$, —C(O)—$OR_{29}$, —C(O)—$NR_{31}R_{32}$ or —C($NR_{31}$)—$NR_{31}R_{32}$ radicals;

(4) —$OR_{29}$, —O—C(O)—$R_{29}$, —O—C(O)—$NR_{31}R_{32}$ or —O—C(O)—$NR_{33}$—S(O)$_2$—$R_{30}$ radicals;

(5) —$SR_{29}$, —S(O)—$R_{30}$, —S(O)$_2$—$R_{30}$, —S(O)$_2$—$NR_{31}R_{32}$, —S(O)$_2$—$NR_{33}$—C(O)—$R_{30}$, —S(O)$_2$—$NR_{33}$—C(O)—$OR_{30}$ or —S(O)$_2$—$NR_{33}$—C(O)—$NR_{31}R_{32}$ radicals; or (6) —$NR_{31}R_{32}$, —$NR_{33}$—C(O)—$R_{29}$, —$NR_{33}$—C(O)—$OR_{30}$, —$NR_{33}$—C(O)—$NR_{31}R_{32}$, —$NR_{33}$—C($NR_{31}$)—$NR_{31}R_{32}$, —$NR_{33}$—S(O)$_2$—$R_{30}$ or —$NR_{33}$—S(O)$_2$—$NR_{31}R_{32}$ radicals;

provided that the total number of aryl, heteroaryl, cycloalkyl and heterocyclyl radicals substituted on each of $R_{11}$ and $R_{12}$ is 0–1;

preferably, $R_{11}$ is an aryl or heteroaryl radical other than an "N"-heteroaryl radical, and $R_{12}$ is a "N"-heteroaryl radical, wherein the aryl, heteroaryl and "N"-heteroaryl radicals are optionally substituted by 1–2 radicals of (1) $R_{30}$;

(2) halo or cyano radicals;

(3) —C(O)—$R_{30}$, —C(O)—$OR_{29}$, —C(O)—$NR_{31}R_{32}$ or —C($NR_{31}$)—$NR_{31}R_{32}$ radicals;

(4) —$OR_{29}$, —O—C(O)—$R_{29}$, —O—C(O)—$NR_{31}R_{32}$ or —O—C(O)—$NR_{33}$—S(O)$_2$—$R_{30}$ radicals;

(5) —$SR_{29}$, —S(O)—$R_{30}$, —S(O)$_2$—$R_{30}$, —S(O)$_2$—$NR_{31}R_{32}$, S(O)$_2$—$NR_{33}$—C(O)—$R_{30}$, —S(O)$_2$—$NR_{33}$—C(O)—$OR_{30}$ or —S(O)$_2$—$NR_{33}$—C(O)—$NR_{31}R_{32}$ radicals; or (6) —$NR_{31}R_{32}$, —$NR_{33}$—C(O)—$R_{29}$, —$NR_{33}$—C(O)—$OR_{30}$, —$NR_{33}$—C(O)—$NR_{31}R_{32}$, —$NR_{33}$—C($NR_{31}$)—$NR_{31}R_{32}$, —$NR_{33}$—S(O)$_2$—$R_{30}$ or —$NR_{33}$—S(O)$_2$—$NR_{31}R_{32}$ radicals;

provided that the total number of aryl, heteroaryl, cycloalkyl and heterocyclyl radicals substituted on each of $R_{11}$ and $R_{12}$ is 0–1;

more preferably, $R_{11}$ is an aryl or heteroaryl radical other than an "N"-heteroaryl radical, and $R_{12}$ is a "N"-heteroaryl radical, wherein the aryl, heteroaryl and "N"-heteroaryl radicals are optionally substituted by 1–2 radicals of (1) $R_{30}$;

(2) halo or cyano radicals;

(3) —C(O)—$R_{30}$, —C(O)—$OR_{29}$, —C(O)—$NR_{31}R_{32}$ or —C($NR_{31}$)—$NR_{31}R_{32}$ radicals; or (4) —$OR_{29}$, —$SR_{29}$, —S(O)—$R_{30}$, —S(O)$_2$—$R_{30}$, —S(O)$_2$—$NR_{31}R_{32}$, —$NR_{31}R_{32}$, —$NR_{33}$—C(O)—$R_{29}$ or —$NR_{33}$—C(O)—$OR_{30}$ radicals;

more preferably, $R_{11}$ is an aryl or heteroaryl radical other than an "N"-heteroaryl radical, and $R_{12}$ is a "N"-heteroaryl radical, wherein the aryl, heteroaryl and "N"-heteroaryl radicals are optionally substituted by 1–2 radicals of (1) $R_{30}$;

(2) halo or cyano radicals;

(3) —C(O)—$R_{30}$, —C(O)—$OR_{29}$, —C(O)—$NR_{31}R_{32}$ or —C($NR_{31}$)—$NR_{31}R_{32}$ radicals; or (4) —$OR_{29}$, —$SR_{29}$, —S(O)—$R_{30}$, —S(O)$_2$—$R_{30}$, —S(O)$_2$—$NR_{31}R_{32}$, —$NR_{31}R_{32}$ or —$NR_{33}$—C(O)—$R_{29}$ radicals;

more preferably, $R_{11}$ is an aryl or heteroaryl radical other than an "N"-heteroaryl radical, and $R_{12}$ is a "N"-heteroaryl radical, wherein the aryl, heteroaryl and "N"-heteroaryl radicals are optionally substituted by 1–2 radicals of (1) $R_{30}$;

(2) halo or cyano radicals; or (3) —C(O)—$NR_{31}R_{32}$, —$OR_{29}$, —$SR_{29}$, —S(O)—$R_{30}$, —S(O)$_2$—$R_{30}$, —S(O)$_2$—$NR_{31}R_{32}$, —$NR_{31}R_{32}$ or —$NR_{33}$—C(O)—$R_{29}$ radicals;

more preferably, $R_{11}$ is an aryl or heteroaryl radical other than an "N"-heteroaryl radical, optionally substituted by 1–2 radicals of (1) $R_{30}$; (2) halo or cyano radicals; or (3) —C(O)—$NR_{31}R_{32}$, —$OR_{29}$, —$SR_{29}$, —S(O)—$R_{30}$, —S(O)$_2$—$R_{30}$, —S(O)$_2$—$NR_{31}R_{32}$, —$NR_{31}R_{32}$ or —$NR_{33}$—C(O)—$R_{29}$ radicals; more preferably, $R_{11}$ is an aryl radical optionally substituted by 1–2 radicals of methyl, amino, dimethylamino, acetamido, hydroxy, halo, cyano, methoxy, methylthio, methylsulfinyl, methylsulfonyl, aminocarbonyl, methyl or trifluoromethyl radicals; more preferably, $R_{11}$ is an unsubstituted phenyl or naphthyl radical or a phenyl radical substituted by 1–2 radicals of methyl, amino, dimethylamino, acetamido, hydroxy, halo, cyano, methoxy, methylthio, methylsulfinyl, methylsulfonyl, aminocarbonyl, methyl or trifluoromethyl radicals; and most preferably, $R_{11}$ is an unsubstituted phenyl radical or a phenyl radical substituted by 1–2 radicals of methyl, amino, dimethylamino, acetamido, hydroxy, halo, cyano, methoxy, methylthio, methylsulfonyl, methyl or trifluoromethyl radicals;

more preferably, $R_{12}$ is an "N"-heteroaryl radical optionally substituted by 1–2 radicals of (1) $R_{30}$; (2) halo or cyano radicals; or (3) —C(O)—$NR_{31}R_{32}$, —$OR_{29}$, —$SR_{29}$, —$NR_{31}R_{32}$ or —$NR_{33}$—C(O)—$R_{29}$ radicals; more preferably, $R_{12}$ is an "N"-heteroaryl radical optionally substituted by 1–2 radicals of amino, dimethylamino, acetamido, hydroxy, halo, cyano, methoxy, methyl or trifluoromethyl radicals; more preferably, $R_{12}$ is a 4-pyridyl, 4-pyrimidyl, 4-quinolinyl, 7-imidazo[4,5-b]pyridinyl, 8-quinazolinyl, 6-(1H)-purinyl, or a 4-imidazolyl radical optionally substituted by a radical of amino, dimethylamino, acetamido, hydroxy, halo, cyano, methoxy, methyl or trifluoromethyl radicals; and most preferably, $R_{12}$ is a 4-pyridyl or 4-pyrimidyl radical optionally substituted by a radical of amino, dimethylamino, acetamido, hydroxy, halo, cyano, methoxy, methyl or trifluoromethyl radicals;

wherein each $R_{30}$ is independently (1) alkyl, alkenyl or alkynyl radicals optionally substituted by 1–3 radicals of —$NR_{31}R_{31}$, —$CO_2R_{23}$, hydroxy, alkoxy, alkylthio, alkylsulfinyl, alkylsulfonyl, cyano, halo or aralkoxy, aralkylthio, aralkylsulfonyl, heterocyclyl, aryl or heteroaryl radicals optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl;

(2) heterocyclyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or (3) aryl or heteroaryl radicals optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl or haloalkyl;

preferably, each $R_{30}$ is independently (1) $C_1$–$C_4$ alkyl, $C_2$–$C_4$ alkenyl or $C_2$–$C_4$ alkynyl radicals optionally substituted by 1–3 radicals of —$NR_{31}R_{31}$, —$CO_2R_{23}$, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo or aryl-$C_1$–$C_4$-alkoxy, aryl-$C_1$–$C_4$-alkylthio, aryl-$C_1$–$C_4$-alkylsulfonyl, heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals;

(2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or (3) aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;

more preferably, each $R_{30}$ is independently (1) $C_1$–$C_4$ alkyl radical optionally substituted by 1–3 radicals of (a) —$NR_{31}R_{31}$;

(b) $C_1$–$C_4$ alkoxy-carbonyl or phenoxycarbonyl or phenylmethoxycarbonyl optionally substituted by 1–3 radicals of amino, alkylamino, di-($C_1$–$C_4$-alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or trifluoromethyl; or (c) hydroxy, $C_1$–$C_4$ alkoxy, $C_1$–$C_4$ alkylthio, or phenyl-$C_1$–$C_4$-alkoxy, phenyl-$C_1$–$C_4$-alkylthio, heterocyclyl, phenyl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;

(2) $C_1$–$C_4$ haloalkyl of 1–3 halo radical; or (3) aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or trifluoromethyl radicals;

more preferably, each $R_{30}$ is independently (1) $C_1$–$C_4$ alkyl radical optionally substituted by (a) amino, $C_1$–$C_4$ alkylamino or di-($C_1$–$C_4$-alkyl)amino radicals; or (b) hydroxy, $C_1$–$C_4$ alkoxy, heterocyclyl, phenyl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or trifluoromethyl radicals;

(2) $C_1$–$C_2$ haloalkyl of 1–3 halo radical; or (3) aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or trifluoromethyl radicals;

more preferably, each $R_{30}$ is independently (1) $C_1$–$C_4$ alkyl radical optionally substituted by a phenyl or heteroaryl radical optionally substituted by 1–3 radicals of amino, di-($C_1$–$C_2$ alkyl)amino, acetamido, hydroxy, $C_1$–$C_2$ alkoxy, halo, $C_1$–$C_4$ alkyl or trifluoromethyl radicals;

(2) trifluoromethyl radical; or (3) aryl or heteroaryl radicals optionally substituted by 1–3 radicals of amino, di-($C_1$–$C_2$ alkyl)amino, acetamido, hydroxy, $C_1$–$C_2$ alkoxy, halo, $C_1$–$C_4$ alkyl or trifluoromethyl radicals;

more preferably, each $R_{30}$ is independently (1) $C_1$–$C_4$ alkyl radical optionally substituted by a phenyl or heteroaryl radical optionally substituted by 1–3 radicals of amino, dimethylamino, acetamido, hydroxy, halo, methoxy, methyl or trifluoromethyl radicals;

(2) trifluoromethyl radical; or (3) aryl or heteroaryl radicals optionally substituted by 1–3 radicals of amino, dimethylamino, acetamido, hydroxy, halo, methoxy, methyl or trifluoromethyl radicals;

most preferably, $R_{30}$ is independently (1) $C_1$–$C_4$ alkyl radical optionally substituted by a phenyl or heteroaryl radical optionally substituted by 1–2 radicals of amino, dimethylamino, acetamido, hydroxy, halo, methoxy, methyl or trifluoromethyl radicals;

(2) trifluoromethyl radical; or (3) aryl or heteroaryl radicals optionally substituted by 1–3 radicals of amino, dimethylamino, acetamido, hydroxy, halo, methoxy, methyl or trifluoromethyl radicals;

each $R_{29}$ is independently hydrogen radical or $R_{30}$; and each $R_{31}$ is independently (1) hydrogen radicals;

(2) alkyl radical optionally substituted by an cycloalkyl, aryl, heterocyclyl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or (3) aryl, heteroaryl, heterocyclyl or cycloalkyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl;

preferably, each $R_{31}$ is independently (1) hydrogen radicals;

(2) $C_1$–$C_4$ alkyl radical optionally substituted by an $C_3$–$C_8$ cycloalkyl, aryl, heterocyclyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or (3) aryl, heteroaryl, heterocyclyl or $C_3$–$C_8$ cycloalkyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

more preferably, each $R_{31}$ is independently (1) hydrogen radicals; or (2) $C_1$–$C_4$ alkyl radical optionally substituted by an phenyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, $C_1$–$C_4$ alkyl or trifluoromethyl radicals;

more preferably, each $R_{31}$ is independently hydrogen or $C_1$–$C_4$ alkyl radicals; and most preferably, each $R_{31}$ is independently hydrogen, methyl or ethyl radicals;

each $R_{32}$ is independently (1) hydrogen radicals;

(2) alkyl radical optionally substituted by an cycloalkyl, aryl, heterocyclyl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or (3) aryl, heteroaryl, heterocyclyl or cycloalkyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl;

preferably, each $R_{32}$ is independently (1) hydrogen radicals;

(2) $C_1$–$C_4$ alkyl radical optionally substituted by an $C_3$–$C_8$ cycloalkyl, aryl, heterocyclyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or (3) aryl, heteroaryl, heterocyclyl or $C_3$–$C_8$ cycloalkyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

more preferably, each $R_{32}$ is independently (1) hydrogen radicals;

(2) $C_1$–$C_4$ alkyl radical optionally substituted by an $C_3$–$C_6$ cycloalkyl, aryl, heterocyclyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or (3) aryl, heteroaryl, heterocyclyl or $C_3$–$C_6$ cycloalkyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

more preferably, each $R_{32}$ is independently (1) hydrogen radicals;

(2) $C_1$–$C_4$ alkyl radical optionally substituted by phenyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkyl or trifluoromethyl radicals; or (3) phenyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, (Ci—$C_4$ alkoxy)carbonylamino, hydroxy, $C_1$–$C_4$ alkoxy, $C_1$–$C_4$ alkyl or trifluoromethyl radicals;

more preferably, each $R_{32}$ is independently (1) hydrogen radicals;

(2) $C_1$–$C_4$ alkyl radical or $C_1$–$C_2$ alkyl radical substituted by phenyl or heteroaryl radical optionally substituted by 1–3 radicals of amino, dimethylamino, acetamido, hydroxy, methoxy, methyl or trifluoromethyl radicals; or (3) phenyl or heteroaryl radical optionally substituted by 1–3 radicals of amino, dimethylamino, acetamido, hydroxy, methoxy, methyl or trifluoromethyl radicals;

most preferably, $R_{32}$ is independently (1) hydrogen or $C_1$–$C_4$ alkyl radical; or (2) phenyl or heteroaryl radical optionally substituted by 1–2 radicals of amino, dimethylamino, acetamido, hydroxy, methoxy, methyl or trifluoromethyl radicals; and wherein each $R_{33}$ is independently (1) hydrogen radical; or (2) alkyl radical optionally substituted by a radical of heterocyclyl, aryl or heteroaryl optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl;

preferably, each $R_{33}$ is independently (1) hydrogen radical; or (2) $C_1$–$C_4$ alkyl radical optionally substituted by a radical of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

more preferably, each $R_{33}$ is independently hydrogen or $C_1$–$C_4$ alkyl radical; and most preferably, each $R_{33}$ is independently hydrogen or methyl radical; and provided that when X is C—H, then Q is other than a phenyl radical; and when X is N and J is C—H, A is other than a 4-(methylsulfonyl)phenyl, 4-(aminosulfonyl)phenyl, 4-(trifluoromethylcarbonylaminosulfonyl)phenyl or 4-(methylaminosulfonyl)phenyl radical.

The compounds of this invention may have in general several asymmetric centers and are typically depicted in the form of racemic mixtures. This invention is intended to encompass racemic mixtures, partially racemic mixtures and separate enantiomers and diastereomers.

Compounds of interest include the following:

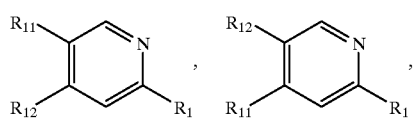

-continued

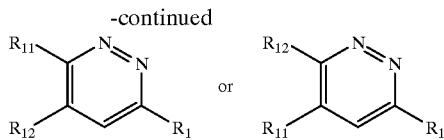

and preferably,

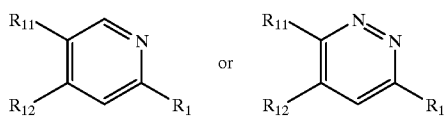

wherein $R_1$, $R_{11}$ and $R_{12}$ are one of the combinations given in the following table:

| $R^{11}$ | $R^{12}$ | $R^1$ |
|---|---|---|
| Phenyl | 4-pyridyl | 3-phenylpropylamino |
| 3-fluorophenyl | 4-pyridyl | 3-phenylpropylamino |
| 4-fluorophenyl | 4-pyridyl | 3-phenylpropylamino |
| 4-fluorophenyl | 4-pyrimidyl | 3-phenylpropylamino |
| 3-tolyl | 4-pyrimidyl | 3-phenylpropylamino |
| 3-tolyl | 4-pyridyl | 3-phenylpropylamino |
| 3-CF$_3$-phenyl | 4-pyridyl | 3-phenylpropylamino |
| 3,4-dichlorophenyl | 4-pyridyl | 3-phenylpropylamino |
| 3,4-dimethylphenyl | 4-pyridyl | 3-phenylpropylamino |
| 2-thienyl | 4-pyrimidyl | 3-phenylpropylamino |
| 2-furyl | 4-pyridyl | 3-phenylpropylamino |
| 2-benzothienyl | 4-pyridyl | 3-phenylpropylamino |
| 2-benzofuryl | 4-pyridyl | 3-phenylpropylamino |
| Phenyl | 4-pyridyl | 3-benzyl-1-piperidinyl |
| 3-fluorophenyl | 4-pyridyl | 3-benzyl-1-piperidinyl |
| 4-fluorophenyl | 4-pyridyl | 3-benzyl-1-pyrrolidinyl |
| 3-CF$_3$-phenyl | 4-pyrimidyl | 3-benzyl-1-piperidinyl |
| 3,4-dimethylphenyl | 4-pyrimidyl | 3-benzyl-1-piperidinyl |
| 3-tolyl | 4-pyridyl | 3-benzyl-1-piperidinyl |
| 3-CF$_3$-phenyl | 4-pyridyl | 3-benzyl-1-piperidinyl |
| 3,4-dichlorophenyl | 4-pyridyl | 3-benzyl-1-piperidinyl |
| 3,4-dimethylphenyl | 4-pyridyl | 2-benzyl-4-morpholino |
| 2-thienyl | 4-pyridyl | 3-benzyl-1-piperidinyl |
| 2-furyl | 4-pyridyl | 3-benzyl-1-piperidinyl |
| 2-benzothienyl | 4-pyridyl | 3-benzyl-1-piperidinyl |
| 2-benzofuryl | 4-pyridyl | 3-benzyl-1-piperidinyl |
| Phenyl | 4-pyridyl | 3-benzyl-1-piperazinyl |
| 3-fluorophenyl | 4-pyridyl | 3-benzyl-1-piperazinyl |
| 4-fluorophenyl | 4-pyridyl | 3-benzyl-1-piperazinyl |
| 3-tolyl | 4-pyridyl | 3-benzyl-1-piperazinyl |
| 3-CF$_3$-phenyl | 4-pyridyl | 3-benzyl-1-piperazinyl |
| 3-fluorophenyl | 4-pyrimidyl | 3-benzyl-1-piperazinyl |
| Phenyl | 4-pyrimidyl | 3-benzyl-1-piperazinyl |
| 3,4-dichlorophenyl | 4-pyridyl | 3-benzyl-1-piperazinyl |
| 3,4-dimethylphenyl | 4-pyridyl | 3-benzyl-1-piperazinyl |
| 2-thienyl | 4-pyridyl | 3-benzyl-1-piperazinyl |
| 2-furyl | 4-pyridyl | 3-benzyl-1-piperazinyl |
| 2-benzothienyl | 4-pyrimidyl | 3-benzyl-1-piperazinyl |
| 2-benzofuryl | 4-pyridyl | 3-benzyl-1-piperazinyl |
| Phenyl | 4-pyridyl | 2-amino-3-phenylpropylamino |
| 3-fluorophenyl | 4-pyridyl | 2-amino-3-phenylpropylamino |
| 4-fluorophenyl | 4-pyridyl | 2-amino-3-phenylpropylamino |
| 3-tolyl | 4-pyridyl | 2-amino-3-phenylpropylamino |
| 3-CF$_3$-phenyl | 4-pyridyl | 2-amino-3-phenylpropylamino |
| 3,4-dichlorophenyl | 4-pyridyl | 2-amino-3-phenylpropyl amino |
| 3,4-dimethylphenyl | 4-pyridyl | 2-amino-3-phenylpropyl amino |
| 3-fluorophenyl | 4-pyrimidyl | 2-amino-3-phenylpropyl amino |
| 3-tolyl | 4-pyrimidyl | 2-amino-3-phenylpropyl amino |
| 2-thienyl | 4-pyridyl | 2-amino-3-phenylpropylamino |
| 2-furyl | 4-pyrimidyl | 2-amino-3-phenylpropylamino |
| 2-benzothienyl | 4-pyridyl | 2-amino-3-phenylpropylamino |
| 2-benzofuryl | 4-pyridyl | 2-amino-3-phenylpropylamino |
| Phenyl | 4-pyridyl | 3-amino-3-phenylpropylamino |
| 4-fluorophenyl | 4-pyridyl | 3-amino-3-phenylpropylamino |
| 3,4-dimethylphenyl | 4-pyrimidyl | 3-amino-3-phenylpropylamino |
| 3-fluorophenyl | 4-pyrimidyl | 3-amino-3-phenylpropylamino |
| 3-tolyl | 4-pyridyl | 3-amino-3-phenylpropylamino |
| 3-CF$_3$-phenyl | 4-pyridyl | 3-amino-3-phenylpropylamino |
| 2-thienyl | 4-pyridyl | 3-amino-3-phenylpropylamino |
| 2-furyl | 4-pyridyl | 3-amino-3-phenylpropylamino |
| 2-benzothienyl | 4-pyridyl | 3-amino-3-phenylpropylamino |
| 2-benzofuryl | 4-pyrimidyl | 3-amino-3-phenylpropylamino |
| Phenyl | 4-pyridyl | 3-amino-3-phenyl-2,2-dimethylpropylamino |
| 3-fluorophenyl | 4-pyridyl | 3-amino-3-phenyl-2,2-dimethylpropylamino |
| 4-fluorophenyl | 4-pyridyl | 3-amino-3-phenyl-2,2-dimethylpropylamino |
| 3-tolyl | 4-pyridyl | 3-amino-3-phenyl-2,2-dimethylpropylamino |
| 3-CF$_3$-phenyl | 4-pyridyl | 3-amino-3-phenyl-2,2-dimethylpropylamino |
| 3,4-dichlorophenyl | 4-pyridyl | 3-amino-3-phenyl-2,2-dimethylpropylamino |
| 3,4-dimethylphenyl | 4-pyridyl | 3-amino-3-phenyl-2,2-dimethylpropylamino |
| 3-fluorophenyl | 4-pyrimidyl | 3-amino-3-phenyl-2,2-dimethylpropylamino |
| 3-tolyl | 4-pyrimidyl | 3-amino-3-phenyl-2,2-dimethylpropylamino |
| 2-thienyl | 4-pyridyl | 3-amino-3-phenyl-2,2-dimethylpropylamino |
| 2-furyl | 4-pyrimidyl | 3-amino-3-phenyl-2,2-dimethylpropylamino |
| 2-benzothienyl | 4-pyridyl | 3-amino-3-phenyl-2,2-dimethylpropylamino |
| 2-benzofuryl | 4-pyridyl | 3-amino-3-phenyl-2,2-dimethylpropylamino |

Further compounds of interest include the following:

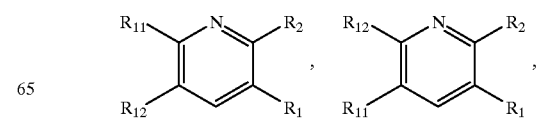

-continued

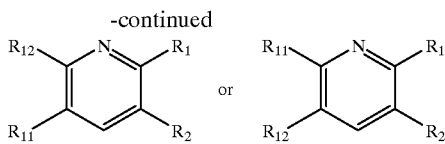

and preferably,

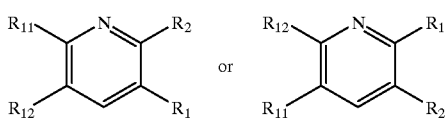

wherein $R_2$ is a hydrogen, methyl, trifluoromethyl, cyano, phenyl or 4-pyridyl radical, preferably, $R_2$ is a hydrogen, methyl or trifluoromethyl radical, and $R_1$, $R_{11}$ and $R_{12}$ are one of the combinations given in the following table:

| $R^{11}$ | $R^{12}$ | $R^1$ |
|---|---|---|
| Phenyl | 4-pyridyl | 3-phenylpropylamino |
| 3-fluorophenyl | 4-pyridyl | 3-phenylpropylamino |
| 4-fluorophenyl | 4-pyridyl | 3-phenylpropylamino |
| 4-fluorophenyl | 4-pyrimidyl | 3-phenylpropylamino |
| 3-tolyl | 4-pyrimidyl | 3-phenylpropylamino |
| 3-tolyl | 4-pyridyl | 3-phenylpropylamino |
| 3-CF$_3$-phenyl | 4-pyridyl | 3-phenylpropylamino |
| 3,4-dichlorophenyl | 4-pyridyl | 3-phenylpropylamino |
| 3,4-dimethyl phenyl | 4-pyridyl | 3-phenylpropylamino |
| 2-thienyl | 4-pyrimidyl | 3-phenylpropylamino |
| 2-furyl | 4-pyridyl | 3-phenylpropylamino |
| 2-benzothienyl | 4-pyridyl | 3-phenylpropylamino |
| 2-benzofuryl | 4-pyridyl | 3-phenylpropylamino |
| Phenyl | 4-pyridyl | 3-benzyl-1-piperidinyl |
| 3-fluorophenyl | 4-pyridyl | 3-benzyl-1-piperidinyl |
| 4-fluorophenyl | 4-pyridyl | 3-benzyl-1-pyrrolidinyl |
| 3-CF$_3$-phenyl | 4-pyrimidyl | 3-benzyl-1-piperidinyl |
| 3,4-dimethyl phenyl | 4-pyrimidyl | 3-benzyl-1-piperidinyl |
| 3-tolyl | 4-pyridyl | 3-benzyl-1-piperidinyl |
| 3-CF$_3$-phenyl | 4-pyridyl | 3-benzyl-1-piperidinyl |
| 3,4-dichlorophenyl | 4-pyridyl | 3-benzyl-1-piperidinyl |
| 3,4-dimethyl phenyl | 4-pyridyl | 2-benzyl-4-morpholino |
| 2-thienyl | 4-pyridyl | 3-benzyl-1-piperidinyl |
| 2-furyl | 4-pyridyl | 3-benzyl-1-piperidinyl |
| 2-benzothienyl | 4-pyridyl | 3-benzyl-1-piperidinyl |
| 2-benzofuryl | 4-pyridyl | 3-benzyl-1-piperidinyl |
| Phenyl | 4-pyridyl | 3-benzyl-1-piperazinyl |
| 3-fluorophenyl | 4-pyridyl | 3-benzyl-1-piperazinyl |
| 4-fluorophenyl | 4-pyridyl | 3-benzyl-1-piperazinyl |
| 3-tolyl | 4-pyridyl | 3-benzyl-1-piperazinyl |
| 3-CF$_3$-phenyl | 4-pyridyl | 3-benzyl-1-piperazinyl |
| 3-fluorophenyl | 4-pyrimidyl | 3-benzyl-1-piperazinyl |
| Phenyl | 4-pyrimidyl | 3-benzyl-1-piperazinyl |
| 3,4-dichlorophenyl | 4-pyridyl | 3-benzyl-1-piperazinyl |
| 3,4-dimethyl phenyl | 4-pyridyl | 3-benzyl-1-piperazinyl |
| 2-thienyl | 4-pyridyl | 3-benzyl-1-piperazinyl |
| 2-furyl | 4-pyridyl | 3-benzyl-1-piperazinyl |
| 2-benzothienyl | 4-pyrimidyl | 3-benzyl-1-piperazinyl |
| 2-benzofuryl | 4-pyridyl | 3-benzyl-1-piperazinyl |
| Phenyl | 4-pyridyl | 2-amino-3-phenylpropylamino |
| 3-fluorophenyl | 4-pyridyl | 2-amino-3-phenylpropylamino |
| 4-fluorophenyl | 4-pyridyl | 2-amino-3-phenylpropylamino |
| 3-tolyl | 4-pyridyl | 2-amino-3-phenylpropylamino |
| 3-CF$_3$-phenyl | 4-pyridyl | 2-amino-3-phenylpropylamino |
| 3,4-dichlorophenyl | 4-pyridyl | 2-amino-3-phenylpropylamino |
| 3,4-dimethyl phenyl | 4-pyridyl | 2-amino-3-phenylpropylamino |
| 3-fluorophenyl | 4-pyrimidyl | 2-amino-3-phenylpropylamino |
| 3-tolyl | 4-pyrimidyl | 2-amino-3-phenylpropylamino |
| 2-thienyl | 4-pyridyl | 2-amino-3-phenylpropylamino |
| 2-furyl | 4-pyrimidyl | 2-amino-3-phenylpropylamino |
| 2-benzothienyl | 4-pyridyl | 2-amino-3-phenylpropylamino |
| 2-benzofuryl | 4-pyridyl | 2-amino-3-phenylpropylamino |
| Phenyl | 4-pyridyl | 3-amino-3-phenylpropylamino |
| 4-fluorophenyl | 4-pyridyl | 3-amino-3-phenylpropylamino |
| 3,4-dimethyl phenyl | 4-pyrimidyl | 3-amino-3-phenylpropylamino |
| 3-fluorophenyl | 4-pyrimidyl | 3-amino-3-phenylpropylamino |
| 3-tolyl | 4-pyridyl | 3-amino-3-phenypropylamino |
| 3-CF$_3$-phenyl | 4-pyridyl | 3-amino-3-phenyipropylamino |
| 2-thienyl | 4-pyridyl | 3-amino-3-phenylpropylamino |
| 2-furyl | 4-pyridyl | 3-amino-3-phenylpropylamino |
| 2-benzothienyl | 4-pyridyl | 3-amino-3-phenylpropylamino |
| 2-benzofuryl | 4-pyrimidyl | 3-amino-3-phenylpropylamino |
| Phenyl | 4-pyridyl | 3-amino-3-phenyl-2,2-dimethylpropylamino |
| 3-fluorophenyl | 4-pyridyl | 3-amino-3-phenyl-2,2-dimethylpropylamino |
| 4-fluorophenyl | 4-pyridyl | 3-amino-3-phenyl-2,2-dimethylpropylamino |
| 3-tolyl | 4-pyridyl | 3-amino-3-phenyl-2,2-dimethylpropylamino |
| 3-CF$_3$-phenyl | 4-pyridyl | 3-amino-3-phenyl-2,2-dimethylpropylamino |
| 3,4-dichlorophenyl | 4-pyridyl | 3-amino-3-phenyl-2,2-dimethylpropylamino |
| 3,4-dimethyl phenyl | 4-pyridyl | 3-amino-3-phenyl-2,2-dimethylpropylamino |
| 3-fluorophenyl | 4-pyrimidyl | 3-amino-3-phenyl-2,2-dimethylpropylamino |
| 3-tolyl | 4-pyrimidyl | 3-amino-3-phenyl-2,2-dimethylpropylamino |
| 2-thienyl | 4-pyridyl | 3-amino-3-phenyl-2,2-dimethylpropylamino |
| 2-furyl | 4-pyrimidyl | 3-amino-3-phenyl-2,2-dimethylpropylamino |
| 2-benzothienyl | 4-pyridyl | 3-amino-3-phenyl-2,2-dimethylpropylamino |
| 2-benzofuryl | 4-pyridyl | 3-amino-3-phenyl-2,2-dimethylpropylamino |

Still further compounds of interest include the following:

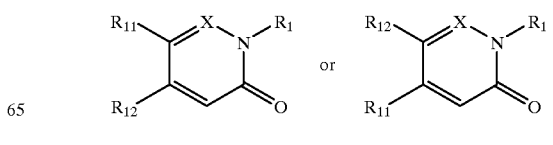

wherein X is N or C—H, and $R_1$, $R_{11}$ and $R_{12}$ are one of the combinations given in the following table:

| $R^{11}$ | $R^{12}$ | $R^1$ |
|---|---|---|
| Phenyl | 4-pyridyl | 3-phenylpropyl |
| 3-fluorophenyl | 4-pyridyl | 3-phenylpropyl |
| 4-fluorophenyl | 4-pyridyl | 3-phenylpropyl |
| 3-tolyl | 4-pyridyl | 3-phenylpropyl |
| 3-trifluoromethylphenyl | 4-pyridyl | 3-phenylpropyl |
| 3,4-dichlorophenyl | 4-pyridyl | 3-phenylpropyl |
| 3,4-dimethylphenyl | 4-pyridyl | 3-phenylpropyl |
| Phenyl | 4-pyridyl | 2-amino-3-phenylpropyl |
| 3-fluorophenyl | 4-pyridyl | 2-amino-3-phenylpropyl |
| 4-fluorophenyl | 4-pyridyl | 2-amino-3-phenylpropyl |
| 3-tolyl | 4-pyridyl | 2-amino-3-phenylpropyl |
| 3-trifluoromethylphenyl | 4-pyridyl | 2-amino-3-phenylpropyl |
| 3,4-dichlorophenyl | 4-pyridyl | 2-amino-3-phenylpropyl |
| 3,4-dimethylphenyl | 4-pyrimidyl | 2-amino-3-phenylpropyl |
| Phenyl | 4-pyridyl | 3-amino-3-phenylpropyl |
| 4-fluorophenyl | 4-pyridyl | 3-amino-3-phenylpropyl |
| 3-tolyl | 4-pyridyl | 3-amino-3-phenylpropyl |
| 3-trifluoromethylphenyl | 4-pyridyl | 3-amino-3-phenylpropyl |
| 2-thienyl | 4-pyridyl | 2-amino-3-phenylpropyl |
| 3-benzofuryl | 4-pyridyl | 2-amino-3-phenylpropyl |
| Phenyl | 4-pyrimidyl | 3-amino-3-phenylpropyl |
| 4-fluorophenyl | 4-pyrimidyl | 3-amino-3-phenylpropyl |
| 3-tolyl | 4-pyrimidyl | 3-amino-3-phenylpropyl |
| 3-trifluoromethylphenyl | 4-pyrimidyl | 2-amino-3-phenylpropyl |
| 2-thienyl | 4-pyrimidyl | 2-amino-3-phenylpropyl |
| 3-benzofuryl | 4-pyrimidyl | 2-amino-3-phenylpropyl |
| Phenyl | 4-(2-amino-pyrimidyl | 3-amino-3-phenylpropyl |
| 4-fluorophenyl | 4-(2-amino-pyrimidyl | 3-amino-3-phenylpropyl |
| 3-tolyl | 4-(2-amino-pyrimidyl | 3-amino-3-phenylpropyl |
| 3-trifluoromethylphenyl | 4-(2-amino-pyrimidyl | 2-amino-3-phenylpropyl |
| 2-thienyl | 4-(2-amino-pyrimidyl | 2-amino-3-phenylpropyl |
| 3-benzofuryl | 4-(2-amino-pyrimidyl | 2-amino-3-phenylpropyl |
| Phenyl | 4-quinolyl | 3-amino-3-phenylpropyl |
| 4-fluorophenyl | 4-quinolyl | 3-amino-3-phenylpropyl |
| 3-tolyl | 4-quinolyl | 3-amino-3-phenylpropyl |
| 3-trifluoromethylphenyl | 4-quinolyl | 2-amino-3-phenylpropyl |
| 2-thienyl | 4-quinolyl | 2-amino-3-phenylpropyl |
| 3-benzofuryl | 4-quinolyl | 2-amino-3-phenylpropyl |
| Phenyl | 4-pyridyl | 3-amino-3-phenyl-2,2-dimethylpropyl |
| 3-fluorophenyl | 4-pyridyl | 3-amino-3-phenyl-2,2-dimethylpropyl |
| 4-fluorophenyl | 4-pyridyl | 3-amino-3-phenyl-2,2-dimethylpropyl |
| 3-tolyl | 4-pyridyl | 3-amino-3-phenyl-2,2-dimethylpropyl |
| 3-$CF_3$-phenyl | 4-pyridyl | 3-amino-3-phenyl-2,2-dimethylpropyl |
| 3,4-dichlorophenyl | 4-pyridyl | 3-amino-3-phenyl-2,2-dimethylpropyl |
| 3,4-dimethylphenyl | 4-pyridyl | 3-amino-3-phenyl-2,2-dimethylpropyl |
| 3-fluorophenyl | 4-pyrimidyl | 3-amino-3-phenyl-2,2-dimethylpropyl |
| 3-tolyl | 4-pyrimidyl | 3-amino-3-phenyl-2,2-dimethylpropyl |
| 2-thienyl | 4-pyridyl | 3-amino-3-phenyl-2,2-dimethylpropyl |
| 2-furyl | 4-pyrimidyl | 3-amino-3-phenyl-2,2-dimethylpropyl |
| 2-benzothienyl | 4-pyridyl | 3-amino-3-phenyl-2,2-dimethylpropyl |
| 2-benzofuryl | 4-pyridyl | 3-amino-3-phenyl-2,2-dimethylpropyl |
| Phenyl | 4-pyridyl | 2-benzyl-4-piperidinyl |
| 3-fluorophenyl | 4-pyridyl | 2-benzyl-4-piperidinyl |
| 4-fluorophenyl | 4-pyridyl | 2-benzyl-4-piperidinyl |
| 3-$CF_3$-phenyl | 4-pyrimidyl | 2-benzyl-4-piperidinyl |
| 3,4-dimethylphenyl | 4-pyrimidyl | 2-benzyl-4-piperidinyl |
| 3-tolyl | 4-pyridyl | 2-benzyl-4-piperidinyl |
| 3 -$CF_3$-phenyl | 4-pyridyl | 2-benzyl-4-piperidinyl |
| 3,4-dichlorophenyl | 4-pyridyl | 2-benzyl-4-piperidinyl |
| 3,4-dimethylphenyl | 4-pyridyl | 2-benzyl-4-piperidinyl |
| 2-thienyl | 4-pyridyl | 2-benzyl-4-piperidinyl |
| 2-furyl | 4-pyridyl | 2-benzyl-4-piperidinyl |
| 2-benzothienyl | 4-pyrimidyl | 2-benzyl-4-piperidinyl |
| 2-benzofuryl | 4-pyrimdyl | 2-benzyl-4-piperidinyl |
| Phenyl | 4-pyridyl | phenylethyl |
| 3-fluorophenyl | 4-pyridyl | phenylethyl |
| 4-fluorophenyl | 4-pyridyl | phenylethyl |
| 3-tolyl | 4-pyridyl | phenylethyl |
| 3-trifluoromethylphenyl | 4-pyridyl | phenylethyl |
| 3,4-dichlorophenyl | 4-pyridyl | phenylethyl |
| 3,4-dimethylphenyl | 4-pyridyl | phenylethyl |
| Phenyl | 4-pyridyl | benzyl |
| 3-fluorohenyl | 4-pyridyl | benzyl |
| 4-fluorophenyl | 4-pyridyl | benzyl |
| 3-tolyl | 4-pyridyl | benzyl |
| 3-trifluoromethylphenyl | 4-pyridyl | benzyl |
| 3,4-dichlorophenyl | 4-pyridyl | benzyl |
| 3,4-dimethylphenyl | 4-pyrimidyl | benzyl |
| Phenyl | 4-pyrimidyl | 2-chlorophenylmethyl |
| 4-fluorophenyl | 4-pyridyl | 2-chlorophenylmethyl |
| 3-tolyl | 4-pyridyl | 2-chlorophenylmethyl |
| 3-trifluoromethylphenyl | 4-pyridyl | 2-chlorophenylmethyl |
| 2-thienyl | 4-pyridyl | 2-chlorophenylmethyl |
| 3-benzofuryl | 4-pyridyl | 2-chlorophenylmethyl |
| Phenyl | 4-pyrimidyl | 4-pyridylmethyl |
| 4-fluorophenyl | 4-pyrimidyl | 4-pyridylmethyl |
| 3-tolyl | 4-pyrimidyl | 4-pyridylmethyl |
| 3-trifluoromethylphenyl | 4-pyrimidyl | 4-pyridylmethyl |
| 2-thienyl | 4-pyrimidyl | 4-pyridylmethyl |
| 3-benzofuryl | 4-pyrimidyl | 4-pyridylmethyl |
| Phenyl | 4-(2-amino-pyrimidyl | 4-pyrolidinylmethyl |
| 4-fluorophenyl | 4-(2-amino-pyrimidyl | 4-pyrolidinylmethyl |
| 3-tolyl | 4-(2-amino-pyrimidyl | 4-pyrolidinylmethyl |
| 3-trifluoromethylphenyl | 4-(2-amino-pyrimidyl | 4-pyrolidinylmethyl |
| 2-thienyl | 4-(2-amino-pyrimidyl | 4-pyrolidinylmethyl |
| 2-benzothiophenyl | 4-pyridyl | 4-pyrolidinylmethyl |
| 2-quinolyl | 4-pyridyl | 4-pyrolidinylmethyl |
| 3-isopropylphenyl | 4-pyridyl | 4-pyrolidinylmethyl |

Additional preferred compounds are included in the Examples, infra.

As utilized herein, the following terms shall have the following meanings:

"a" means the bond order of the bond between J and the adjacent ring carbon atom to which W is attached. "a" may be either a single or double bond. "b" means the bond order of the bond between W and the adjacent ring carbon atom to which W is attached. "b" may be either a single or double bond.

"Alkyl", alone or in combination, means a straight-chain or branched-chain alkyl radical containing preferably 1–15 carbon atoms ($C_1$–$C_{15}$), more preferably 1–8 carbon atoms ($C_1$–$C_8$), even more preferably 1–6 carbon atoms ($C_1$–$C_6$), yet more preferably 1–4 carbon atoms ($C_1$–$C_4$), still more preferably 1–3 carbon atoms ($C_1$–$C_3$), and most preferably 1–2 carbon atoms ($C_1$–$C_2$). Examples of such radicals include methyl, ethyl, n-propyl, isopropyl, n-butyl, isobutyl, sec-butyl, tert-butyl, pentyl, iso-amyl, hexyl, octyl and the like.

"Hydroxyalkyl", alone or in combination, means an alkyl radical as defined above wherein at least one hydrogen radical is replaced with a hydroxyl radical, preferably 1–3 hydrogen radicals are replaced by hydroxyl radicals, more preferably 1–2 hydrogen radicals are replaced by hydroxyl radicals, and most preferably one hydrogen radical is replaced by a hydroxyl radical. Examples of such radicals include hydroxymethyl, 1-, 2-hydroxyethyl, 1-, 2-, 3-hydroxypropyl, 1,3-dihydroxy-2-propyl, 1,3-dihydroxybutyl, 1,2,3,4,5,6-hexahydroxy-2-hexyl and the like.

"Alkenyl", alone or in combination, means a straight-chain or branched-chain hydrocarbon radical having one or more double bonds, preferably 1–2 double bonds and more preferably one double bond, and containing preferably 2–15 carbon atoms ($C_2$–$C_{15}$), more preferably 2–8 carbon atoms ($C_2$–$C_8$), even more preferably 2–6 carbon atoms ($C_2$–$C_6$), yet more preferably 2–4 carbon atoms ($C_2$–$C_4$), and still more preferably 2–3 carbon atoms ($C_2$–$C_3$). Examples of such alkenyl radicals include ethenyl, propenyl, 2-methylpropenyl, 1,4-butadienyl and the like.

"Alkoxy", alone or in combination, means a radical of the type "R—O—" wherein "R" is an alkyl radical as defined above and "O" is an oxygen atom. Examples of such alkoxy radicals include methoxy, ethoxy, n-propoxy, isopropoxy, n-butoxy, iso-butoxy, sec-butoxy, tert-butoxy and the like.

"Alkoxycarbonyl", alone or in combination, means a radical of the type "R—O—C(O)—" wherein "R—O—" is an alkoxy radical as defined above and "C(O)" is a carbonyl radical.

"Alkoxycarbonylamino", alone or in combination, means a radical of the type "R—O—C(O)—NH—" wherein "R—O—C(O)" is an alkoxycarbonyl radical as defined above, wherein the amino radical may optionally be substituted, such as with alkyl, aryl, aralkyl, cycloalkyl, cycloalkylalkyl and the like.

"Alkylthio", alone or in combination, means a radical of the type "R—S—" wherein "R" is an alkyl radical as defined above and "S" is a sulfur atom. Examples of such alkylthio radicals include methylthio, ethylthio, n-propylthio, isopropylthio, n-butylthio, iso-butylthio, sec-butylthio, tert-butylthio and the like.

"Alkylsulfinyl", alone or in combination, means a radical of the type "R—S(O)—" wherein "R" is an alkyl radical as defined above and "S(O)" is a mono-oxygenated sulfur atom. Examples of such alkylsulfinyl radicals include methylsulfinyl, ethylsulfinyl, n-propylsulfinyl, isopropylsulfinyl, n-butylsulfinyl, iso-butylsulfinyl, sec-butylsulfinyl, tert-butylsulfinyl and the like.

"Alkylsulfonyl", alone or in combination, means a radical of the type "R—S(O)$_2$—" wherein "R" is an alkyl radical as defined above and "S(O)$_2$" is a di-oxygenated sulfur atom. Examples of such alkylsulfonyl radicals include methylsulfonyl, ethylsulfonyl, n-propylsulfonyl, isopropylsulfonyl, n-butylsulfonyl, iso-butylsulfonyl, sec-butylsulfonyl, tert-butylsulfonyl and the like.

"Aryl", alone or in combination, means a phenyl or biphenyl radical, which is optionally benzo fused or heterocyclo fused and which is optionally substituted with one or more substituents selected from alkyl, alkoxy, halogen, hydroxy, amino, azido, nitro, cyano, haloalkyl, carboxy, alkoxycarbonyl, cycloalkyl, alkanoylamino, amido, amidino, alkoxycarbonylamino, N-alkylamidino, alkylamino, dialkylamino, aminoalkyl, alkylaminoalkyl, dialkylaminoalkyl, N-alkylamido, N,N-dialkylamido, aralkoxycarbonylamino, alkylthio, alkylsulfinyl, alkylsulfonyl, oxo and the like. Examples of aryl radicals are phenyl, o-tolyl, 4-methoxyphenyl, 2-(tert-butoxy)phenyl, 3-methyl-4-methoxyphenyl, 2-$CF_3$-phenyl, 2-fluorophenyl, 2-chlorophenyl, 3-nitrophenyl, 3-aminophenyl, 3-acetamidophenyl, 2-amino-3-(aminomethyl)phenyl, 6-methyl-3-acetamidophenyl, 6-methyl-2-aminophenyl, 6-methyl-2,3-diaminophenyl, 2-amino-3-methylphenyl, 4,6-dimethyl-2-aminophenyl, 4-hydroxyphenyl, 3-methyl-4-hydroxyphenyl, 4-(2-methoxyphenyl)phenyl, 2-amino-1-naphthyl, 2-naphthyl, 3-amino-2-naphthyl, 1-methyl-3-amino-2-naphthyl, 2,3-diamino-1-naphthyl, 4,8-dimethoxy-2-naphthyl and the like.

"Aralkyl" and "arylalkyl", alone or in combination, means an alkyl radical as defined above in which at least one hydrogen atom, preferably 1–2, is replaced by an aryl radical as defined above, such as benzyl, 1-, 2-phenylethyl, dibenzylmethyl, hydroxyphenylmethyl, methylphenylmethyl, diphenylmethyl, dichlorophenylmethyl, 4-methoxyphenylmethyl and the like. For example, phenylmethyl means a methylene diradical substituted with a phenyl radical, i.e., Ph—$CH_2$—, whereas a methylphenyl means a phenylene diradical substituted with a methyl radical, i.e., $CH_3$—Ph—.

"Aralkoxyl", alone or in combination, means an alkoxy radical as defined above in which at least one hydrogen atom, preferably 1–2, is replaced by an aryl radical as defined above, such as benzyloxy, 1-, 2-phenylethoxy, dibenzylmethoxy, hydroxyphenylmethoxy, methylphenylmethoxy, dichlorophenylmethoxy, 4-methoxyphenylmethoxy and the like.

"Aralkoxycarbonyl", alone or in combination, means a radical of the type "R—O—C(O)—" wherein "R—O—" is an aralkoxy radical as defined above and "—C(O)—" is a carbonyl radical.

"Alkanoyl", alone or in combination, means a radical of the type "R—C(O)—" wherein "R" is an alkyl radical as defined above and "—C(O)—" is a carbonyl radical. Examples of such alkanoyl radicals include acetyl, trifluoroacetyl, hydroxyacetyl, propionyl, butyryl, valeryl, 4-methylvaleryl, and the like.

"Alkanoylamino", alone or in combination, means a radical of the type "R—C(O)—NH—" wherein "R—C(O)—" is an alkanoyl radical as defined above, wherein the amino radical may optionally be substituted, such as with alkyl, aryl, aralkyl, cycloalkyl, cycloalkylalkyl and the like.

"Aminocarbonyl", alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like.

"Aminosulfonyl", alone or in combination, means an amino substituted sulfonyl radical.

"Benzo", alone or in combination, means the divalent radical $C_6H_4=$ derived from benzene. "Benzo fused" forms a ring system in which benzene and a cycloalkyl or aryl group have two carbons in common, for example tetrahydronaphthylene and the like.

"Bicyclic" as used herein is intended to include both fused ring systems, such as naphthyl and β-carbolinyl, and substituted ring systems, such as biphenyl, phenylpyridyl and diphenylpiperazinyl.

"Cycloalkyl", alone or in combination, means a saturated or partially saturated, preferably one double bond, monocyclic, bicyclic or tricyclic carbocyclic alkyl radical, preferably monocyclic, containing preferably 5–12 carbon atoms ($C_5$–$C_{12}$), more preferably 5–10 carbon atoms ($C_5$–$C_{10}$), even more preferably 5–7 carbon atoms ($C_5$–$C_7$), which is optionally benzo fused or heterocyclo fused and which is optionally substituted as defined herein with respect to the definition of aryl. Examples of such cycloalkyl radicals include cyclopentyl, cyclohexyl, dihydroxycyclohexyl, ethylenedioxycyclohexyl, cycloheptyl, octahydronaphthyl, tetrahydronaphthyl, octahydroquinolinyl, dimethoxytetrahydronaphthyl, 2,3-dihydro-1H-indenyl, azabicyclo[3.2.1]octyl and the like.

"Heteroatoms" means nitrogen, oxygen and sulfur heteroatoms.

"Heterocyclo fused" forms a ring system in which a heterocyclyl or heteroaryl group of 5–6 ring members and a cycloalkyl or aryl group have two carbons in common, for example indole, isoquinoline, tetrahydroquinoline, methylenedioxybenzene and the like.

"Heterocyclyl" means a saturated or partially unsaturated, preferably one double bond, monocyclic or bicyclic, preferably monocyclic, heterocycle radical containing at least one, preferably 1 to 4, more preferably 1 to 3, even more preferably 1–2, nitrogen, oxygen or sulfur atom ring member and having preferably 3–8 ring members in each ring, more preferably 5–8 ring members in each ring and even more preferably 5–6 ring members in each ring. "Heterocyclyl" is intended to include sulfone and sulfoxide derivatives of sulfur ring members and N-oxides of tertiary nitrogen ring members, and carbocyclic fused, preferably 3–6 ring carbon atoms and more preferably 5–6 ring carbon atoms, and benzo fused ring systems. "Heterocyclyl" radicals may optionally be substituted on at least one, preferably 1–4, more preferably 1–3, even more preferably 1–2, carbon atoms by halogen, alkyl, alkoxy, hydroxy, oxo, thioxo, aryl, aralkyl, heteroaryl, heteroaralkyl, amidino, N-alkylamidino, alkoxycarbonylamino, alkylsulfonylamino and the like, and/or on a secondary nitrogen atom by hydroxy, alkyl, aralkoxycarbonyl, alkanoyl, alkoxycarbonyl, heteroaralkyl, aryl or aralkyl radicals. More preferably, "heterocyclyl", alone or in combination, is a radical of a monocyclic or bicyclic saturated heterocyclic ring system having 5–8 ring members per ring, wherein 1–3 ring members are oxygen, sulfur or nitrogen heteroatoms, which is optionally partially unsaturated or benzo-fused and optionally substituted by 1–2 oxo or thioxo radicals. Examples of such heterocyclyl radicals include pyrrolidinyl, piperidinyl, piperazinyl, morpholinyl, thiamorpholinyl, 4-benzyl-piperazin-1-yl, pyrimidyl, tetrahydrofuryl, pyrazolidonyl, pyrazolinyl, pyridazinonyl, pyrrolidonyl, tetrahydrothienyl and its sulfoxide and sulfone derivatives, 2,3-dihydroindolyl, tetrahydroquinolinyl, 1,2,3,4-tetrahydroisoquinolinyl, 1,2,3,4-tetrahydro-1-oxo-isoquinolinyl, 2,3-dihydrobenzofuryl, benzopyranyl, methylenedioxyphenyl, ethylenedioxyphenyl and the like.

"Heteroaryl" means a monocyclic or bicyclic, preferably monocyclic, aromatic heterocycle radical, having at least one, preferably 1 to 4, more preferably 1 to 3, even more preferably 1–2, nitrogen, oxygen or sulfur atom ring members and having preferably 5–6 ring members in each ring, which is optionally saturated carbocyclic fused, preferably 3–4 carbon atoms ($C_3$–$C_4$) to form 5–6 ring membered rings and which is optionally substituted as defined above with respect to the definitions of aryl. Examples of such heteroaryl groups include thienyl, furyl oxazolyl, thiazolyl, benzothiazolyl, benzofuryl, benzothienyl, imidazolyl, pyrrolyl, pyrazolyl, pyridyl, 3-(2-methyl)pyridyl, 3-(4-trifluoromethyl)pyridyl, pyrimidyl, 5-(4-trifluoromethyl) pyrimidyl, pyrazinyl, triazolyl, indolyl, quinolinyl, 5,6,7,8-tetrahydroquinolyl, 5,6,7,8-tetrahydroisoquinolinyl, quinoxalinyl, benzimidazolyl, benzoxazolyl and the like.

""N"-heteroaryl" means an aromatic 5–10 membered monocyclic or bicyclic, preferably a monocyclic, aromatic heterocycle radical containing at least one, preferably 1 to 3, more preferably 1 to 2, even more preferably 1 nitrogen atoms with the remaining atoms being carbon, and having preferably 5–6 ring members in each ring, which is optionally saturated carbocyclic fused, preferably 3–4 carbon atoms ($C_3$–$C_4$) to form 5–6 ring membered rings and which is optionally substituted as defined above with respect to the definitions of aryl. Examples of such "N"-heteroaryl groups include imidazolyl, pyrrolyl, pyrazolyl, pyridyl, 4-(2-amino) pyridyl, 3-(4-trifluoromethyl)pyridyl, pyrimidyl, 5-(4-trifluoromethyl)pyrimidyl, pyrazinyl, triazolyl, indolyl, quinolinyl, imidazopyridine, 5,6,7,8-tetrahydroquinolyl, 5,6,7,8-tetrahydroisoquinolinyl, benzimidazolyl, and the like.

"Heteroaralkyl" and "heteroarylalkyl," alone or in combination, means an alkyl radical as defined above in which at least one hydrogen atom, preferably 1–2, is replaced by a heteroaryl radical as defined above, such as 3-furylpropyl, 2-pyrrolyl propyl, chloroquinolinylmethyl, 2-thienylethyl, pyridylmethyl, 1-imidazolylethyl and the like.

"Halogen" and "halo", alone or in combination, means fluoro, chloro, bromo or iodo radicals.

"Haloalkyl", alone or in combination, means an alkyl radical as defined above in which at least one hydrogen atom, preferably 1–3, is replaced by a halogen radical, more preferably fluoro or chloro radicals. Examples of such haloalkyl radicals include 1,1,1-trifluoroethyl, chloromethyl, 1-bromoethyl, fluoromethyl, difluoromethyl, trifluoromethyl, bis(trifluoromethyl)methyl and the like.

"Pharmacologically acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulphuric acid, phosphoric acid, methanesulphonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al, *J. Pharm. Sci.* 66, 1 (1977).

"Leaving group" (refered to as "L" in the Schemes) generally refers to groups readily displaceable by a nucleophile, such as an amine, a thiol or an alcohol nucleophile. Such leaving groups are well known in the art.

Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6–10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, tri-fluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also sutiable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium flouride reagent, either as a discrete reaction step or in situ during a reaction with the alcohol group. Suitable silylating agents are, for example, trimethylsilyl chloride, tert-buty-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydroylsis and hydrogenolysis conditions well known to those skilled in the art.

The symbols used above have the following meanings:

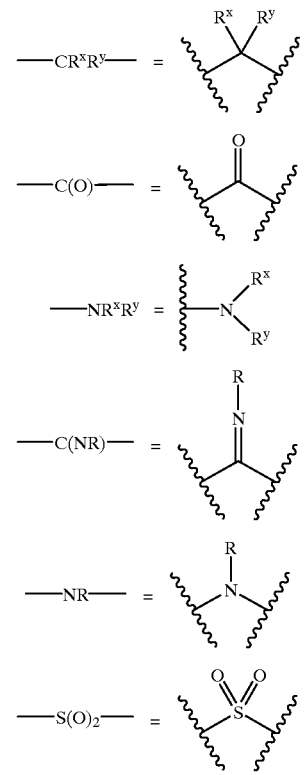

Prodrugs of the compounds of this invention are also contemplated by this invention. A prodrug is an active or inactive compound that is modified chemically through in vivo physiological action, such as hydrolysis, metabolism and the like, into a compound of this invention following adminstration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

Compounds according to the invention can be synthesized according to one or more of the following methods. It should be noted that the general procedures are shown as it relates to preparation of compounds having unspecified stereochemistry. However, such procedures are generally applicable to those compounds of a specific stereochemistry, e.g., where the stereochemistry about a group is (S) or (R). In addition, the compounds having one stereochemistry (e.g., (R)) can often be utilized to produce those having opposite stereochemistry (i.e., (S)) using well-known methods, for example, by inversion.

The invention relates to substituted pyridines or pyridazines which are useful for the treatment of inflammatory disease and diseases in which IL-1 and TNF play a role. Substituted pyridines and pyridazines embodied in the current invention may be prepared as described in the following schemes and synthetic examples.

Pyridines of Formula I wherein X=C—H and J=N may be prepared utilizing the chemistry outlined in Schemes 1 through 3. As shown in Scheme 1, The $R_{12}$ and $R_{11}$ substituents are conveniently introduced from the alcohol and aldehyde precursors to provide dione III. 3,4-substituted pyridones VIIIa and VIIIb may be prepared from cyclopentenones IV and V, respectively, via Beckmann rearrangement and acetate elimination on the intermediate oximes (one isomer represented by VII).

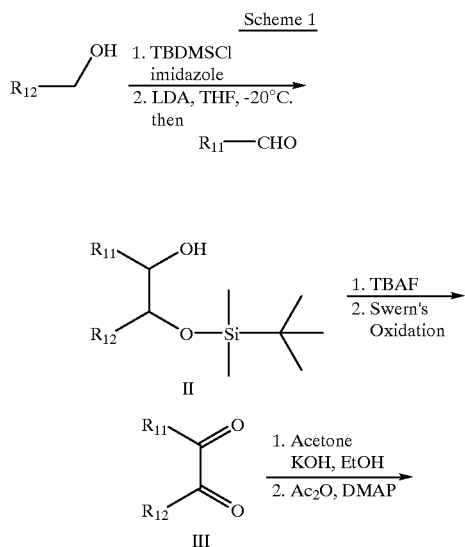

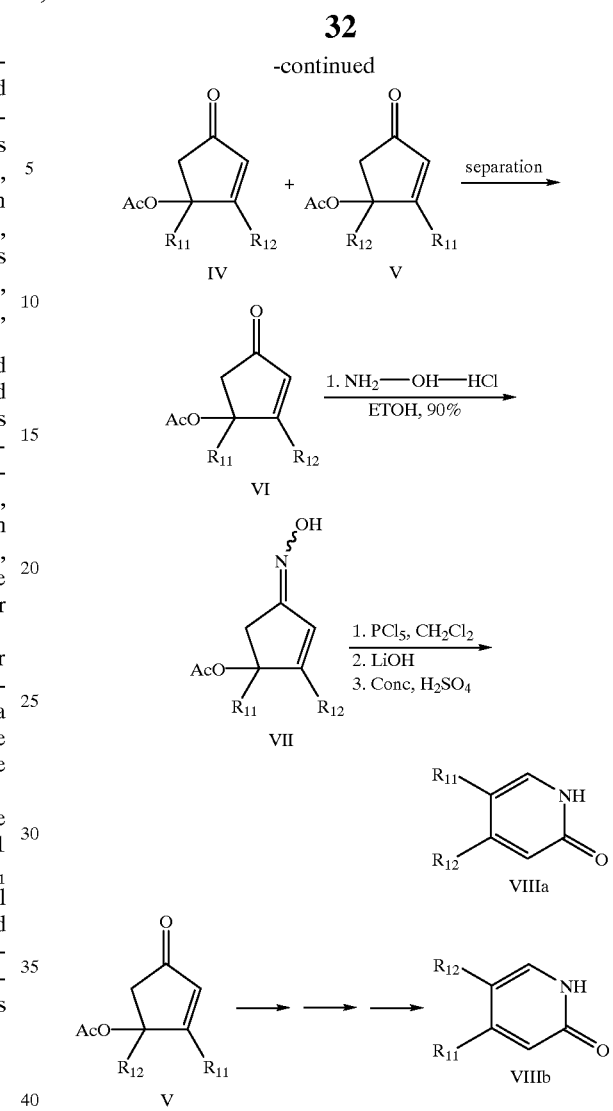

Pyridones VIIIa and VIIIb may be further modified by reaction with $POCl_3$ or $SO_2Cl_2$, as shown in Scheme 2, to form the intermediate 2-chloropyridine which can be used in a variety of displacement reactions with $HNR_5R_{21}$, or $HOR_{21}$, or $HSR_{21}$ in the presence or absence of base at temperatures from 25° C. to 250° C., or carbon bound substituents may be introduced using palladium or nickel catalyzed cross coupling reactions with aryl or alkyl boronic acids, aryl or alkyl stannanes, or aryl or alkyl zinc halides to form compounds of Formula I. Intermediate 2-chloropyridines may be converted to 2-bromopyridines, which are more preferable as partners in palladium or nickel catalyzed cross coupling reactions, by reaction with HBr in HOAc. Furthermore, pyridones VIIIa and VIIIb may be alkylated with an alkyl halide, mesylate, tosylate or the like, in the presence or absence of base, or may be alkylated with an alcohol under Mitsunobu conditions ($Ph_3P$, dialkylazodicarboxylate) to provide compounds of Formula I wherein X=C—H, J=N, and W=—$OR_{21}$.

Scheme 2

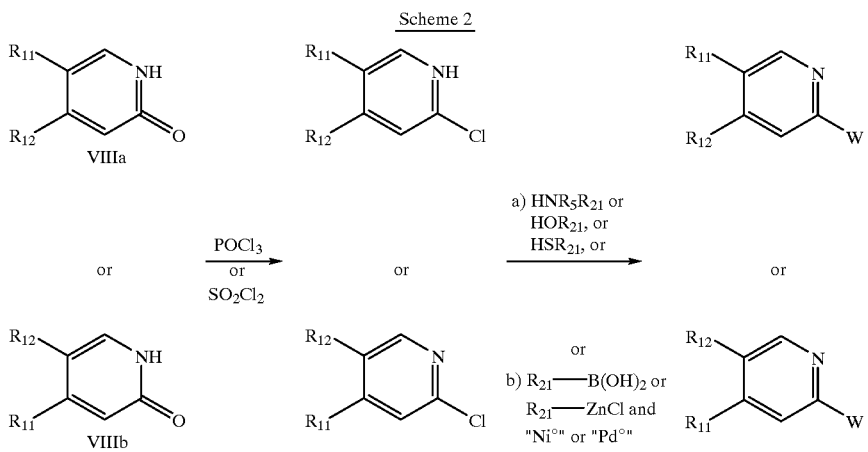

An alternative general route to compounds of formula I wherein X=C—H and J=N is shown in Scheme 3. 4-substituted pyridine IX can be converted to the N oxide X by reaction with an oxidizing agent such as peroxides, peracids, or oxone, followed by treatment with $POCl_3$ to afford XI. Treatment of XI with an amine, alcohol, or sulfide in the presence or absence of a base at a temperature from 25° C. to 250° C. affords XII which is subsequently halogenated by treatment with an appropriate halogenating reagent such as $Br_2$ to afford XIII. Introduction of an $R_{11}$ or $R_{12}$ substituent to XIII may be performed as shown, utilizing an aryl or heteroaryl or "N"-heteroaryl boronic acid, or alternatively, utilizing a corresponding stannane or corresponding zinc halide in the presence of an appropriate palladium or nickel catalyst in an aprotic solvent to provide XIV.

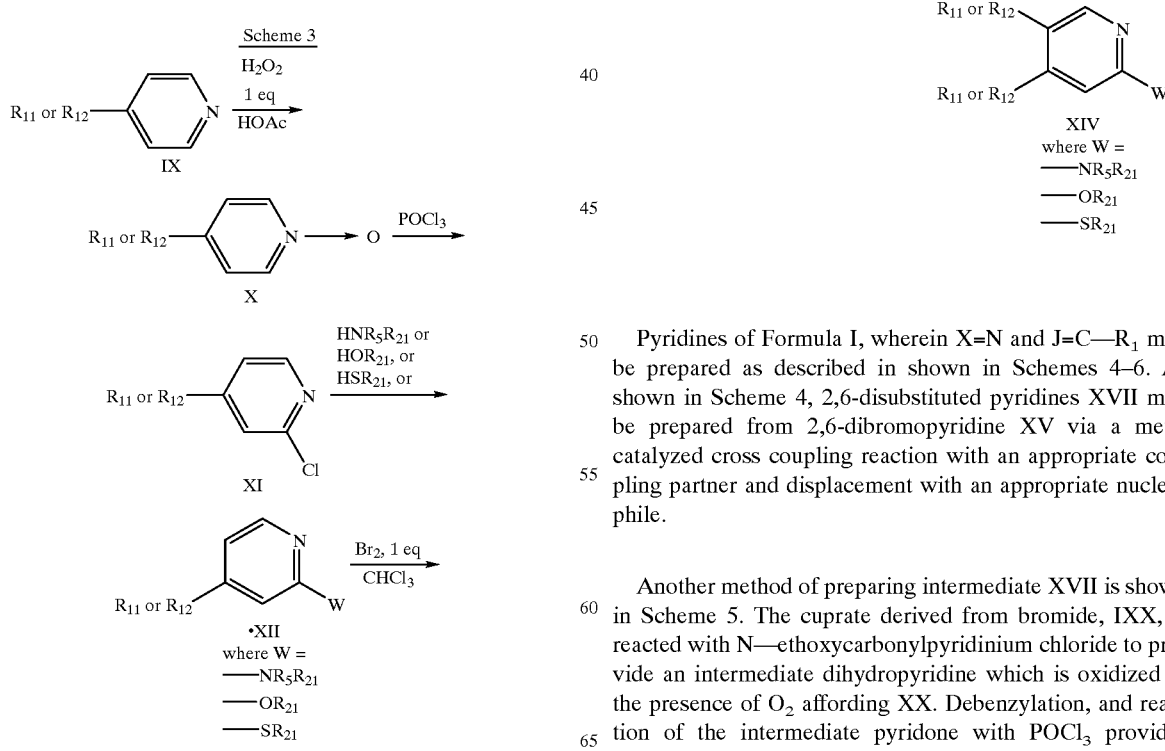

Pyridines of Formula I, wherein X=N and J=C—$R_1$ may be prepared as described in shown in Schemes 4–6. As shown in Scheme 4, 2,6-disubstituted pyridines XVII may be prepared from 2,6-dibromopyridine XV via a metal catalyzed cross coupling reaction with an appropriate coupling partner and displacement with an appropriate nucleophile.

Another method of preparing intermediate XVII is shown in Scheme 5. The cuprate derived from bromide, IXX, is reacted with N—ethoxycarbonylpyridinium chloride to provide an intermediate dihydropyridine which is oxidized in the presence of $O_2$ affording XX. Debenzylation, and reaction of the intermediate pyridone with $POCl_3$ provides 2-chloropyridine XXI, which may may be converted to XVII as described above and shown in the Scheme.

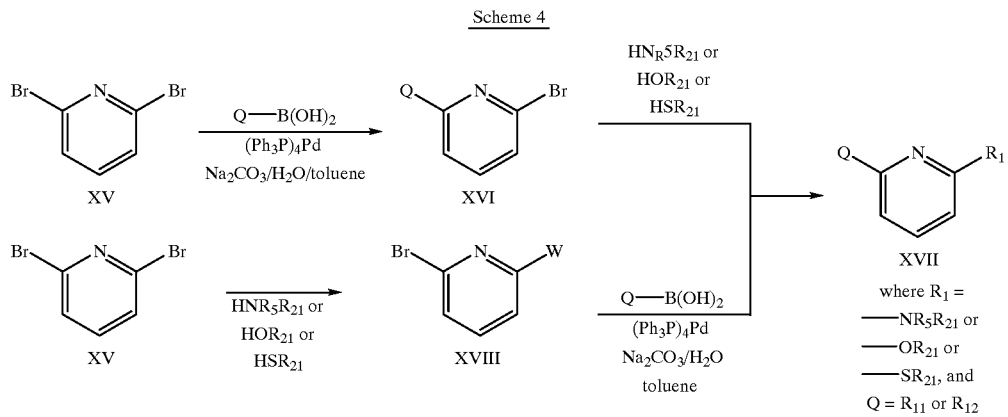

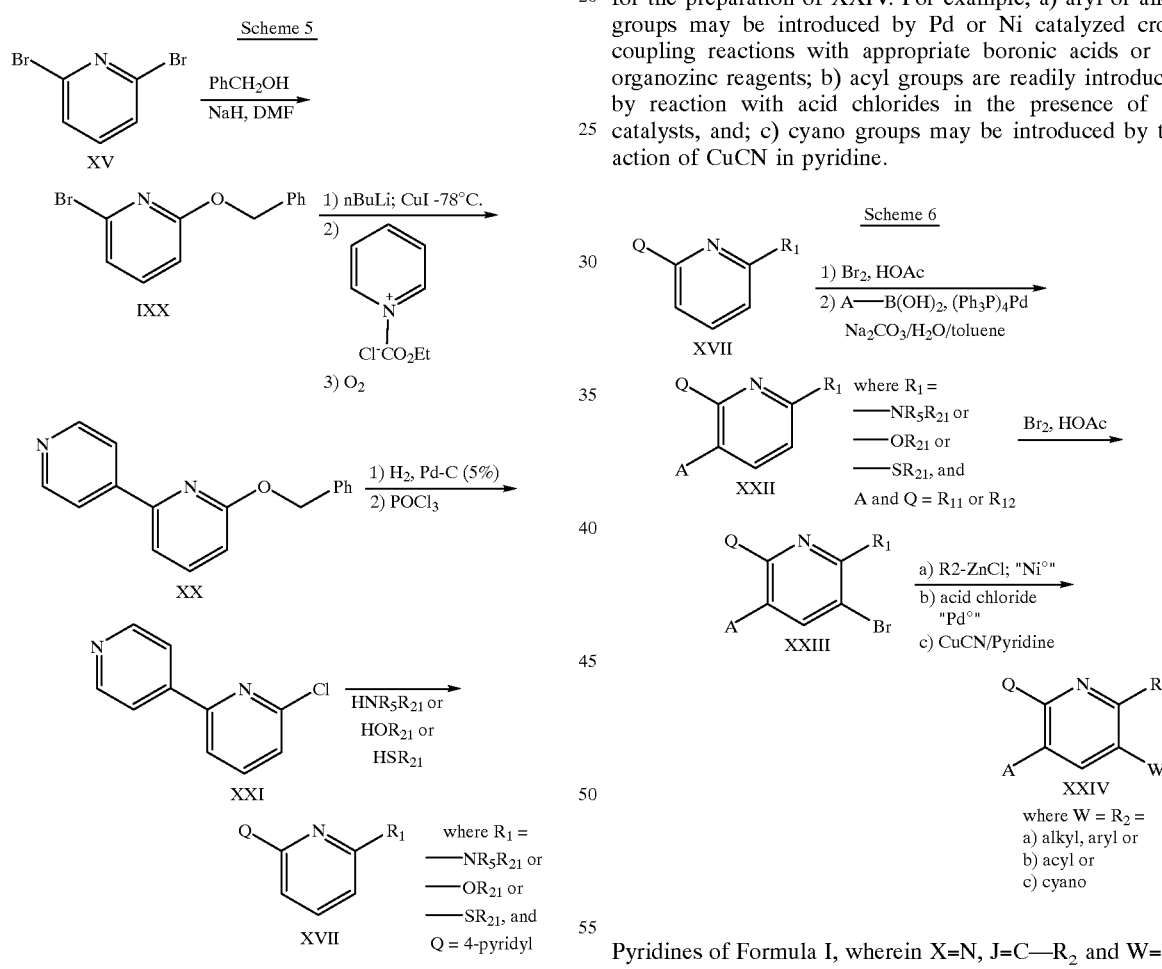

Elaboration of 2,6-disubstitutedpyridines XVII to provide compounds of Formula I wherein X=N, and J=C—$R_1$ is shown in Scheme 6. Bromination of XVII provides an intermediate bromopyridine (not shown) which upon reaction with an aryl or heteroaryl or "N"-heteroaryl boronic acid, or a corresponding organostannane or organozinc halide in the presence of an appropriate palladium or nickel catalyst in an aprotic solvent affords XXII. Introduction of $R_2$ substituents (W=C—$R_1$) may be accomplished by bromination of XXII providing a versatile intermediate, XXIII for the preparation of XXIV. For example, a) aryl or alkyl groups may be introduced by Pd or Ni catalyzed cross coupling reactions with appropriate boronic acids or organozinc reagents; b) acyl groups are readily introduced by reaction with acid chlorides in the presence of Pd catalysts, and; c) cyano groups may be introduced by the action of CuCN in pyridine.

Pyridines of Formula I, wherein X=N, J=C—$R_2$ and W=$R_1$ may be prepared as described in shown in Schemes 7 and 8. 2–Chloro-3-bromo-5-carbomethoxypyridine XXIX may be prepared as described in J. Org. Chem., (1984), 49(26), pp. 5237–5247. Hydrolysis of XXIX followed by coupling of the intermediate pyridone with an appropriate boronic acid and subsequent esterification provides XXX (Scheme 7). Conversion of the pyridone to the intermediate 2-chloropyridine may be performed by treatment with $POCl_3$ or $SO_2Cl_2$. Treatment with an appropriate boronic acid, organostannane or organozinc reagent in the presence of Pd or Ni catalysis provides XXXI.

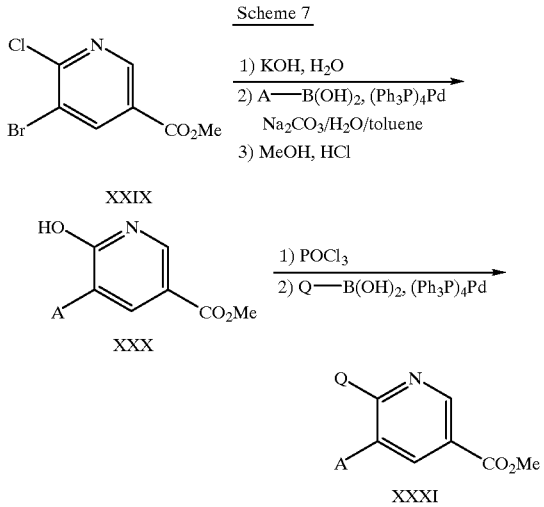

Scheme 7

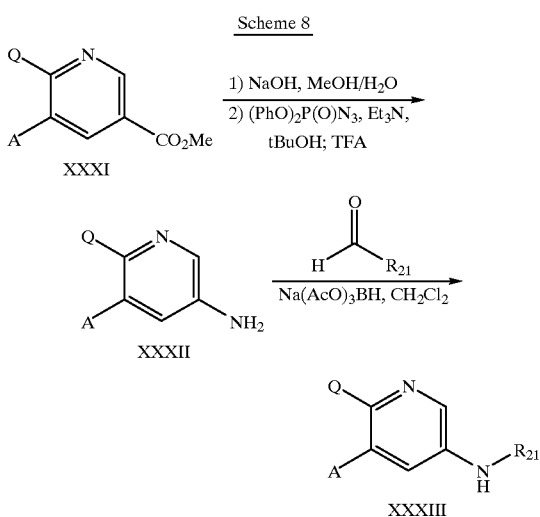

Scheme 8 illustrates the conversion of XXXI to the amine XXXII via a modified curtius reaction (Ninomiya, K, et. al., Tetrahedron (1974) 30(14):2151–2157). Compounds of formula I wherein $W=R_1=NH-R_{21}$ are prepared by reductive alkylation to provide XXXIII.

Scheme 8

A widely applicable method for the preparation of pyridazines involves the condensation of a 1,4-dicarbonyl compound with hydrazine (Scheme 9). An oxidative step is required to give the aromatic pyridazine unless the carbonyl component is unsaturated.

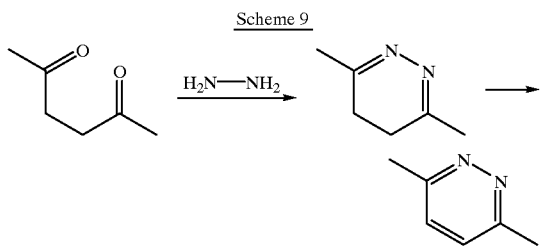

Scheme 9

Thus, a 4-keto carbonic acid or -ester may be reacted with hydrazine to give a dihydropyridazinone which may be dehydrogenated by a bromination-dehydrobromination step or by using sodium 3-nitrobenzenesulfonate as an oxidant (Scheme 10) (e.g. Th. Curtius, J. Prakt. Chem. 50, 509, 1894; Gabriel and Colman, Chem. Ber. 32,395, 1899; D. Libermann and A. Rouaix, Bull. Soc. Chim. Fr. 117, 1959; E. Ravina et al., Arch. Pharm. (Weinheim) 324, 455, 1991).

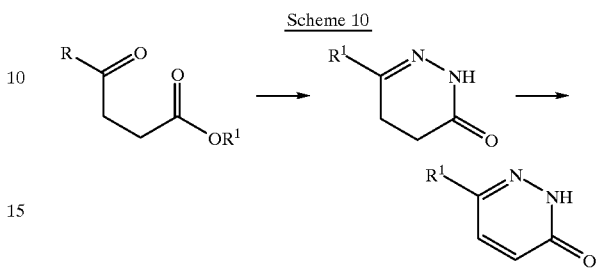

Scheme 10

This approach allows the preparation of 5,6-disubstituted 2H-pyridazin-3-ones by using the corresponding 3,4-disubstituted 4-keto butyric acid or -ester as demonstrated in Scheme 11 (Almstroem, Just. Lieb. Ann. Chem. 400, 137, 1913; E. Ravina et al., Eur. J. Med. Chem. -Chim. Ther.20, 475, 1985; E. Ravina et al., Arch. Pharm. (Weinheim), 324, 455, 1991):

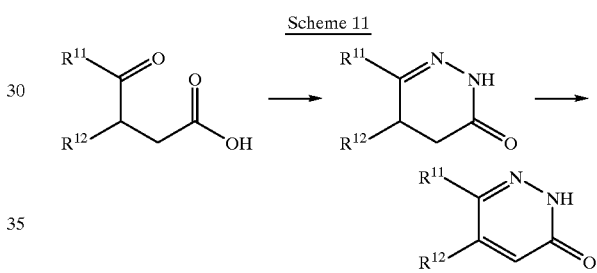

Scheme 11

In a related approach (Scheme 12) that does not require an oxidation step, glyoxylic acid may be reacted with a methylen ketone in a thermic condensation reaction to give a disubstituted 5-hydroxy-2(5H)-furanone. Reaction of this intermediate with hydrazine then may lead directly to the disubstituted pyridazinone (C.-G. Wermuth et al., J.Med.Chem. 30, 239, 1987):

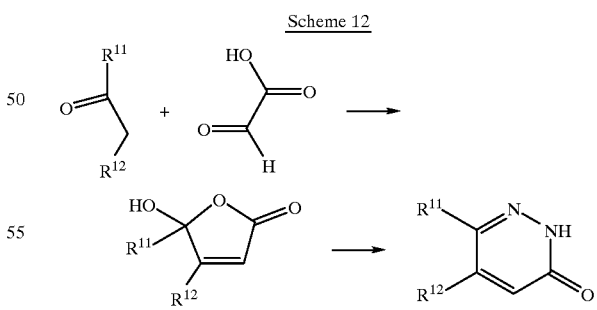

Scheme 12

2H-Pyridazin-3-ones can easily be converted into 3-chloropyridazines (Scheme 13) by treatment with e.g. phosphorus oxychloride at elevated temperature (e.g. Gabriel and Colman, Chem. Ber. 32,395, 1899; D. Libermann and A. Rouaix, Bull. Soc. Chim. Fr. 117, 1959; E. Ravina et al. Arch. Pharm. (Weinheim), 324, 455, 1991; F. Khalifa, Arch. Pharm. (Weinheim) 323, 883, 1990)). The 3-chloropyridazine represents a versatile intermediate for nucleophilic substitution reactions with e.g. primary or secondary amines (e.g. E. Ravina, Arch. Pharm.(Weinheim) 324, 455 (1991)).

Scheme 13

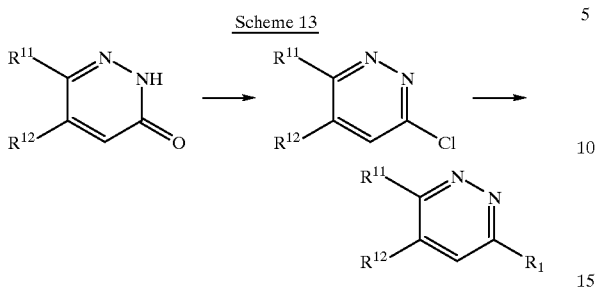

Furthermore, the 3-chloropyridazine may also be subjected to palladium or nickel catalyzed cross coupling reactions with aryl boronic acids or arylzinc halides to provide compounds wherein the 3-substituent is an aryl or heteroaryl (e.g. A. Turck et al. Bull. Soc. Chim. Fr. 130, 488, 1993).

A synthesis leading to 6-substituted-3-(4-fluorophenyl)-4-(4-pyridyl)-pyridazines XL is displayed in Scheme 14. Ketone XXXIV (P. J. Gilligan et al., J. Med. chem. 35, 4344, 1992) may be alkylated with ethyl bromoacetate in the presence of sodium ethoxide (E. Knoevenagel, Chem. Ber. 21, 1344, 1888) to give the ketoester XXXV. Cyclization with hydrazine monohydrate to give the dihydropyridazinone XXXVI is followed by a bromination-dehydrobromination step using bromine in acetic acid and leading to (2H)-pyridazin-3-one XXXVII.

Scheme 14

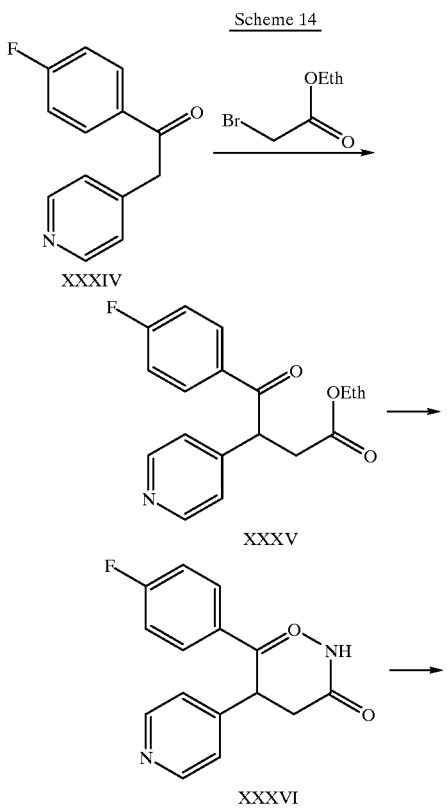

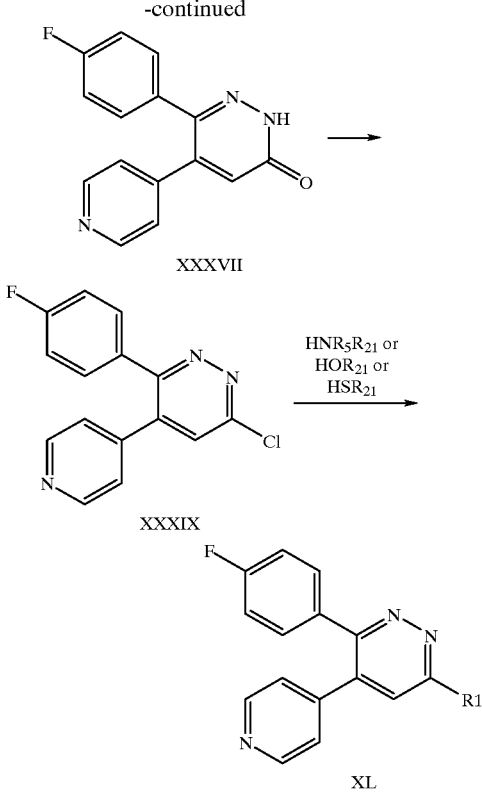

where $R_1$ =
—$NR_5R_{21}$
—$OR_{21}$
—$SR_{21}$

XXXVII may be converted into the chloro derivative XXXIX by treatment with a chlorinating agent such as phosphorus oxychloride at elevated temperature. Treatment of XXXIX with an amine, alcohol, or sulfide in the presence or absence of a base at a temperature from 25° C. to 250° C. yields XL.

Substituted halopyridines may be readily prepared from the corresponding pyridones using phosphorus oxychloride or pentachloride.

Amines of formula $NHR_5R_{21}$ and $NHR_{31}R_{32}$ are commercially available or can be readily prepared by those skilled in the art from commercially available starting materials. For example, an amide, nitro or cyano group can be reduced under reducing conditions, such as in the prescence of a reducing agent like lithium aluminum hydride and the like, to form the corresponding amine. Alkylation and acylation of amino groups are well known in the art. Chiral and achiral substituted amines can be prepared from chiral amino acids and amino acid amides (for example, alkyl, aryl, heteroaryl, cycloalkyl, arylalkyl, heteroarylalkyl, cycloalkylalkyl and the like) using methods well known in the art, such as H. Brunner, P. Hankofer, U. Holzinger, B. Treittinger and H. Schoenenberger, Eur. J. Med. Chem. 25, 35–44, 1990; M. Freiberger and R. B. Hasbrouck, J. Am. Chem. Soc. 82, 696–698, 1960; Dornow and Fust, Chem. Ber. 87, 984, 1954; M. Kojima and J. Fujita, Bull. Chem. Soc. Jpn. 55, 1454–1459, 1982; W. Wheeler and D. O'Bannon, Journal of Labelled Compounds and Radiopharmaceuticals XXXI, 306, 1992; and S. Davies, N. Garrido, O. Ichihara and I. Walters, J. Chem. Soc., Chem. Commun. 1153, 1993.

Alkyl sulfonic acids, aryl sulfonic acids, heterocyclyl sulfonic acids, heteroaryl sulfonic acids, alkylmercaptans, arylmercaptans, heterocyclylmercaptans, heteroarylmercaptans, alkylhalides, arylhalides, heterocyclylhalides, heteroarylhalides, and the like are commercially available or can be readily prepared from starting materials commercially available using standard methods well known in the art.

Thioether derivatives can be converted into the corresponding sulfone or sulfoxide by oxidizing the thioether derivative with a suitable oxidation agent in a suitable solvent. Suitable oxidation agents include, for example, hydrogen peroxide, sodium meta-perborate, oxone (potassium peroxy monosulfate), meta-chloroperoxybenzoic acid, periodic acid and the like, including mixtures thereof. Suitable solvents include acetic acid (for sodium meta-perborate) and, for other peracids, ethers such as THF and dioxane, and acetonitrile, DMF and the like, including mixtures thereof.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. The following Examples are presented for illustrative purposes only and are not intended, nor should they be construed, as limiting the invention in any manner. Those skilled in the art will appreciate that modifications and variations of the compounds disclosed herein can be made without violating the spirit or scope of the present invention.

EXAMPLE 1

The following amines were prepared as intermediates and used to obtain compounds claimed within the scope of this invention.

EXAMPLE 1A

Procedure for the Preparation of 3-phenylbutylamine

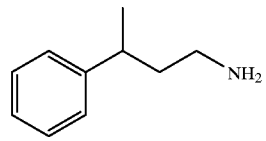

A mixture of 3-phenylbutyraldehyde (3 ml, 20.18 mmol), ammonium acetate (15 g, 195 mmol) and sodium cyanoborohydride (900 mg, 14.32 mmol) in methanol (50 ml) was stirred overnight under an argon atmosphere. The reaction was acidified to pH 2 by the addition of conc HCl. The solvent was evaporated, dichloromethane and water were added, and the aqueous layer was made basic (pH 12) by the addition of solid potassium hydroxide. Extraction (dichloromethane) and concentration gave the title compound as an oil. ES-MS (m/z): 150.2 (M+H)$^+$; $^1$H NMR (CDCl$_3$): d 7.40–7.17 (m, 5H, Ph), 2.81 (q, 1H, CH), 2.62 (m, 2H, CH$_2$), 1.76 (dq, 2H, CH$_2$), 1.29 (d, 3H, CH$_3$).

EXAMPLE 1B

Procedure for the Preparation of 3-(2-methylphenyl)propylamine

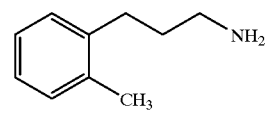

Diethyl cyanomethylphosphonate (5.0 ml, 30.9 mmol) was added to a stirring suspension of sodium hydride (60% oily suspension, 1.24 g, 31 mmol) in tetrahydrofuran (50 ml) under argon. After 30 min, 2-methylbenzaldehyde (3.6 ml, 31.1 mmol) was added and stirring continued for 1 h. The reaction was quenched by the addition of water and extracted with dichloromethane followed by drying and evaporation of the organic solution. Column chromatography (hexane; hexane:ethylacetate=3:1) provided 2-(2-methylphenyl)acrylonitrile as an oil. This material (3.8 g), 10% palladium on carbon (3.8 g) and 12 N hydrochloric acid (11.8 ml, 142 mmol) in methanol (125 ml) were hydrogenated with hydrogen at atmospheric pressure for 2 d. The catalyst was removed by filtration and the solvent was evaporated. The resultant material was partitioned between dichloromethane and water. The aqueous layer was made basic with 10 N sodium hydroxide and extracted with dichloromethane, followed by drying and evaporation. The resultant material was purified on a silica gel column (chloroform:methanol:triethylamine=85:10:5) to provide the title compound as an oil.

EXAMPLE 1C

Procedure for the Preparation of 2-Methyl-3-phenylpropylamine

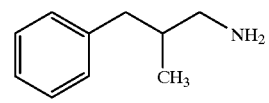

A mixture of commercially available 2-methyl-3-phenylpropylamide (4.32 g, 26.5 mmol) and lithium aluminium hydride (1.3 g, 34.3 mmol) in tetrahydrofuran (184 ml) was stirred at room temperature for 5 h. The reaction mixture was poured into saturated aqueous sodium sulfate and extracted with dichloromethane followed. The combined organic extracts were dried (sodium sulfate) and evaporated to provide the amine as an oil. For alternative preparations see: Dornow and Fust, Chem. Ber. 87, 984 (1954).

EXAMPLE 1D

Procedure for the Preparation of 3-Fluoro-3-phenylpropylamine

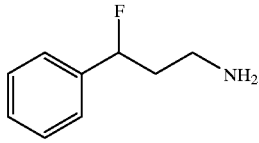

Step A. 3-Hydroxy-3-phenylpropionitrile: Sodium borohydride (1.4 g, 37.00 mmol) was added in portions to a stirring solution of benzoylacetonitrile (10 g, 68.90 mmol) in methanol (200 ml) at ice-bath temperature. After 30 min, the reaction was quenched by the addition of a few drops of acetic acid followed by evaporation. The mixture was partitioned between dichloromethane and water and the combined organic extracts were dried (magnesium, sulfate) and evaporated to provide the Step A compound as a syrup. (cf. Florin, C.; Chantegrel, J.; Charlon, C.; Marsura, A.; Luu-Duc, C. Nouvelle voie de synthese des a-fluorophenylacetonitriles. *Ann. pharmaceuttiques fr.* 1985, 43, 595–599.)

Step B. 3-Fluoro-3-phenylpropionitrile: A solution of 3-hydroxy-3-phenylpropionitrile (3.5 g, 23.8 mmol) in dichloromethane (20 ml) was added at −78° C. to a stirred solution of diethylaminosulfur trifluoride (5 g, 31 mmol) in dichloromethane (23 ml). After 1.5 h, the mixture was allowed to reach room temperature. The reaction was quenched by the addition of water, followed by extraction with dichloromethane, drying of the organic phase and evaporation. Flash chromatography on a column of silica gel (hexane-ethyl acetate=5:1) provided 3-fluoro-3-phenylpropionitrile. $^1$H NMR (CDCl$_3$): d 7.50–7.29 (m, 5H, Ph), 5.73 (dt, 1H, J$_{H,F}$ 46.2 Hz, CHF), 3.00 and 2.96 (dd, t, each 1H, CH$_2$).

Step C. 3-Fluoro-3-phenylpropylamine: A 2N borane-dimethyl sulfide complex solution in tetrahydrofuran (8.8 ml, 17.6 mmol) was added dropwise at room temperature to a stirred solution of 3-fluoro-3-phenylpropionitrile (2 g, 13.41 mmol) in tetrahydrofuran (12 ml). The mixture was warmed to 50° C., the dimethylsulfide was distilled off, and the mixture was then refluxed for 2.5 h. After cooling to 0° C., 1N methanolic hydrogen chloride (20 ml) was added, and the mixture was concentrated. To the resulting concentrate was added dichloromethane and water, and solid potassium hydroxide was added to acheive a pH of aproximately 12. Extraction (dichloromethane) and concentration gave the crude product as a mixture of phenylpropylamine and 3-fluoro-3-phenylpropylamine. Column chromatography on a column of Iatrobeads® (chloroform-methanol-triethylamine=90:7:3) provided the title compound 3-fluoro-3-phenylpropylamine in the first fraction. ES-MS (m/z): 154.0 (M+H)$^+$; $^1$H NMR (CDCl$_3$): d 7.45–7.28 (m, 5H, Ph), 5.60 (ddd, 1H, J$_{H,F}$ 48.2 Hz, CHF), 2.91 (t, 2H, CH$_2$N), 2.15 and 1.96 (2m, each 1H, CH$_2$).

EXAMPLE 1E

Procedure for the Preparation of 2-Fluoro-3-phenylpropylamine

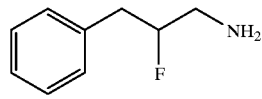

Step A. 1-Azido-2-hydroxy-3-phenylpropane: A mixture of (2,3-epoxypropyl)benzene (9.69 g, 72.22 mmol), sodium azide (16.5 g, 253.8 mmol) and ammonium chloride (6.3 g, 109.5 mmol) in methanol (190 ml) and water (32 ml) was heated at reflux for 1.5 h. The solvent was evaporated, the remainder was partitioned between dichloromethane and water. The organic solution was dried and evaporated to give the Step A compound as an MS (m/z): 178.1 (M+H)$^+$; $^1$H NMR (CDCl$_3$): d 7.43–7.15 (m, 5H, Ph), 4.08 (m, 1H, CH), 3.41 and 3.32 (2dd, each 1H, CH$_2$), 2.85 and 2.83 (2d, each 1H, CH$_2$) , 1.98 (bs, OH).

Step B. 1-Azido-2-fluoro-3-phenylpropane: A solution of 1-azido-2-hydroxy-3-phenylpropane (3.5 g, 19.75 mmol) in dichloromethane (23 ml) was added at −78° C. to a stirred solution of diethylaminosulfur trifluoride (3.4 ml, 25.74 mmol) in dichloromethane (23 ml). The mixture was slowly warmed to room temperature over 2.5 h. The reaction was quenched by the addition of water, and extracted with dichloromethane. Concentration and prification by flash chromatography on a column of silica gel (hexane-ethyl acetate=8:1 to 6:1:1) provided 1-Azido-2-fluoro-3-phenylpropane as an oil. $^1$H NMR (CDCl$_3$): d 7.46–7.20 (m, 5H, Ph), 4.86 (m, 1H, J$_{H,F}$ 48.2 Hz, CHF), 3.41 (m, 2H, CH$_2$), 3.04 (m, 2H, CH$_2$).

Step C. 2-Fluoro-3-phenylpropylamine: A mixture of 1-azido-2-fluoro-3-phenylpropane (900 mg, 5.0 mmol) and 20% palladium-on-carbon (wet, 50%, 500 mg) in methanol (40 ml) was hydrogenated under a balloon of hydrogen for 2 h. The catalyst was removed by filtration and the solvent was evaporated. The resultant product was purified on a short column of Iatrobeads® (chloroform-methanol-triethylamine=90:7:1) to provide the title compound as an oil. ES-MS (m/z): 153.9 (M+H)$^+$; $^1$H NMR (CDCl$_3$): d 7.40–7.22 (m, 5H, Ph), 4.68 (m, 1H, J$_{H,F}$ 48.7 Hz, CHF), 3.11–2.83 (m, 4H, 2CH$_2$).

EXAMPLE 1F

Procedure for the Preparation of 2-amino-3-(2-fluorophenyl)-propylamine

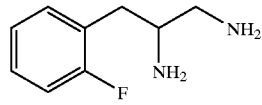

Step A. Methyl 2-amino-3-(2-fluorophenyl)propionate
5 g (27.3 mmol) of (D,L)-(2-fluoro-phenyl)alanine was suspended in 50 ml methanolic HCl and stirred at room temperature for 3 days. The reaction mixture was concentrated in vacuo and dried to give a yellow oil. MS (m/z): 198 (M+H)$^+$; C$_{10}$H$_{12}$FNO$_2$ requir. 197.2.

Step B. 2-Amino-3-(2-fluorophenyl)propionamide
Methyl 2-amino-3-(2-fluorophenyl) propionate was suspended in 50 ml 30% ammonium hydroxide and stirred at room temperature for 18 hrs. The mixture was filtered, washed with cold water and 2-amino-3-(2-fluorophenyl)

propionamide was collected as a white solid. MS (m/z): 183.1 (M+H)[1] C$_9$H$_{11}$FN$_2$O requir. 182.2.

Step C. 2-Amino-3-(2-fluorophenyl)-propylamine: 2-Amino-3-(2-fluorophenyl)propionamide was added carefully to a chilled (5°) mixture of LAH (1.0 g, 26.3 mmol) and 20 ml THF under argon. The reaction was then heated at reflux for 10 hrs. The reaction was cooled to 5° C. and carefully treated with Na$_2$SO$_4$.10 H$_2$O. The resulting mixture was stirred for 18 hrs, then filtered to remove the solids. The filtrate was concentrated in vacuo to give an amber oil. MS (m/z): 169 (M+H)$^+$; C$_9$H$_{13}$FN$_2$ requir. 168.19

EXAMPLE 1G

Procedure for the Preparation of 2-Amino-2-methyl-3-phenylpropylamine

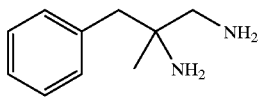

Step A: D,L-α-methyl phenylalanine amide: A solution of commercially available D,L-α-methyl phenylalanine methyl ester (5.0 g, 25.7 mmol) in aqu. 28% ammonium hydroxide (50 ml) was kept at room temperature for 3 d. The resulting white precipitate of D,L-α-methyl phenylalanine amide was filtered and dried.

Step B: 2-Amino-2-methyl-3-phenylpropylamine: D,L-α-methyl phenylalanine amide (2.0 g, 11.22 mmol) was reduced with lithium aluminium hydride (1.3 g, 34.26 mmol) in boiling tetrahydrofuran for 24 h. The reaction was quenched by the addition of sodium sulfate decahydrate at ice-bath temperature. The salts were filtered off, followed by evaporation to leave the title compound as an oil. MS (m/z): 165.1 (M+H)$^+$; C$_{10}$H$_{16}$N$_2$ requir. 164.2. An alternative preparation was reported by M. Freiberger and R. B. Hasbrouck, J. Am. Chem. Soc. 82, 696–698 (1960).

EXAMPLE 1H

Procedure for the Preparation of (S)-1,2-benzylethylenediamine

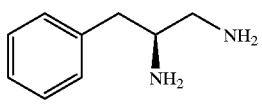

(S)-1,2-Benzylethylendiamine was prepared according to the literature (H. Brunner, P. Hankofer, U. Holzinger, B. Treittinger and H. Schoenenberger, Eur. J. Med. Chem. 25, 35–44, (1990)) by reduction of L-phenylalanine amide with lithium aluminium hydride. The (R)-enantiomer was prepared in the same manner from D-phenylalanine amide.

EXAMPLE 1I

Procedure for the Preparation of (S)-2-N,N-Dimethylamino-3-phenylpropylamine

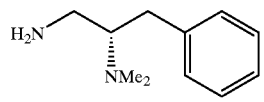

Sodium triacetoxyhydride (13.0 g, 61.3 mmol) was added to a stirring mixture of phenylalanine amide (3.6 g, 21.9 mmol) and 37% formaldehyde solution (4.4 ml, 58.7 mmol) in 1,2-dichloroethane (77 ml). After stirring for 2 h, the reaction was quenched by the addition of sat. aqu. sodium hydrogencarbonate. Then potassium hydroxide pellets were added followed by extraction with dichloromethane, drying of the organic solution and evaporation. The resulting (S)-2-N,N-dimethylamino-3-phenylpropylamide was reduced with lithium aluminium hydride according to the literature (H. Brunner, P. Hankofer, U. Holzinger, B. Treittinger and H. Schoenenberger, Eur. J. Med. Chem. 25, 35–44, (1990)) to provide the title compound.

EXAMPLE 1J

Procedure for the Preparation of (S)-2-N-Ethylamino-3-phenylpropylamine

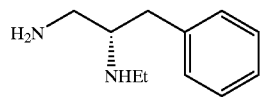

(S)-2-N-Ethylamino-3-phenylpropylamine: Acetic anhydride (1.2 ml, 12.7 mmol) was added to a stirring solution of L-phenylalanine amide (1.0 g, 6.10 mmol) in methanol (25 ml). After 1.5 h at room temperature, it was evaporated followed by drying in an oil pump vacuum. The resultant L-N-ethylphenylalanine amide (6.1 mmol) was reduced with lithium aluminium hydride (570 mg, 15.0 mmol) in tetrahydrofuran (65 mml) at 55° C. for 4 h. The reaction mixture was poured into sat. aqu. sodium hydrogencarbonate followed by extraction with dichloromethane, drying and evaporation. Column chromatography on silica gel (chloroform:methanol:triethylamine=90:7:3) provided the amine as a yellowish oil. MS (m/z): 179.1 (M+H)$^+$; C$_{11}$H$_{18}$N$_2$ requir. 178.3.

EXAMPLE 1K

Procedure for the Preparation of (S)-2-Benzylpiperazine

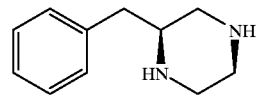

Lithium aluminium hydride (1.6 g, 42.16 mmol) was added in portions to a stirred mixture of (S)-2-benzylpiperazine-3,6-dione (3.0 g, 14.70 mmol) and tetrahydrofuran (80 ml) at 0° C. After 30 min at ice-bath temperature, the mixture was refluxed for 4 h with stirring. The reaction was quenched by the portionwise addition of sodium sulfate decahydrate and some methanol until hydrogen evolution ceased. It was filtered and the solids were washed several

EXAMPLE 1L

Procedure for the Preparation of ((S)-1,2,3,4-tetrahydroisoquinolin-3-ylmethyl)amine

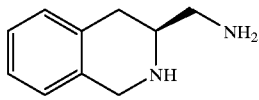

The title compound was obtained from the reduction of (S)-decahydroquinoline-3-carboxamides according to the procedure set forth in Example 1c. Alternatively the title compound may be prepared from (S)-decahydroquinoline-3-carboxylic acid using the procedures described in Example 1f.

Example 1M

Procedure for the Preparation of 1-Phenyl-1,3-propanediamine

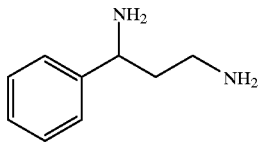

3-Phenyl-3-aminopropionic acid (S. G. Cohen and S. Y. Weinstein, J. Am. Chem. Soc. 86, 725–728, 1964) was converted into 1-phenyl-1,3-propanediamine as reported in the literature (M. Kojima and J. Fujita, Bull. Chem. Soc. Jpn. 55, 1454–1459 (1982)).

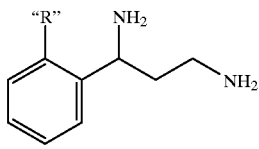

"R" = F, or Me, or Cl

Analogously, 1-(2-fluorophenyl)-1,3-propanediamine, 1-(2-methylphenyl)-1,3-propanediamine and 1-(2-chlorophenyl)-1,3-propanediamine were prepared by using the above procedure and the appropriately substituted 3-phenyl-3-aminopropionic acid.

EXAMPLE 1N

Procedure for the Preparation of (S)-1-Phenyl-1,3-propanediamine

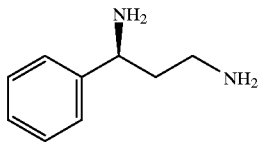

S-3-N-tert.-Butoxycarbonylamino-3-phenylpropionitrile was prepared according to the literature (W. J. Wheeler and D. D. O'Bannon, J. Label.Compds. Radiopharm. XXXI (4), 305–315, 1992) from D-(−)-α-phenylglycinol. For reduction (D. Mitchell and T. M. Koenig, Synth. Comm. 25 (8), 1231–1238, 1995), borane-methyl sulfide complex (2N, 3 ml, 6 mmol) was added dropwise to a solution of the nitrile (1 g, 4.06 mmol) in tetrahydrofuran (6 ml). Methyl sulfide was distilled off and the resulting solution refluxed for 2.5 h. With ice-cooling, methanolic hydrogen chloride (1N, 3 ml) was added followed by evaporation. The remainder was taken up in methanol (10 ml) and 4N hydrogen chloride/dioxane (10 ml) was added. After 1 h at room temperature, it was evaporated and the aqueous solution of the resultant product was washed with dichloromethane. The aqueous solution was made basic by the addition of solid potassium hydroxide followed by repeated dichloromethane extractions. Drying and evaporation of the dichloromethane solution left the crude diamine as an oil. MS (m/z): 150.8 (M+H)$^+$; $C_9H_{14}N_2$ requir. 150.2. The enantiomer, (R)-1-phenyl-1,3-propanediamine, was prepared analogously from L-(+)-α-phenylglycinol. MS (m/z): 150.9 (M+H)$^+$; $C_9H_{14}N_2$ requir. 150.2.

EXAMPLE 1O

Procedure for the Preparation of (1R,2R)-2-methyl-1-phenyl-1,3-propanediamine

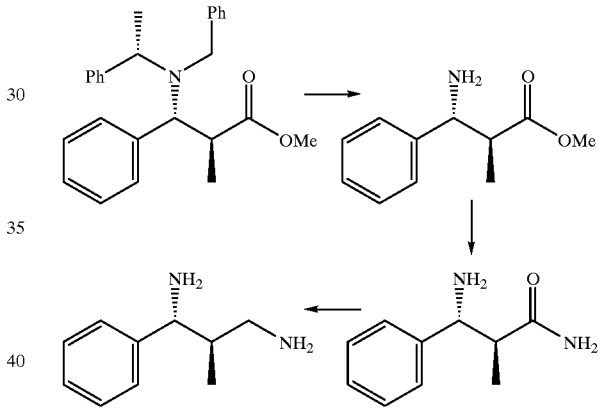

Step A: Methyl(2S,3R,αS)-3-(N-benzyl-N-α-methylbenzylamino)-2-methyl-3-phenylpropionate was prepared as reported for the 2R,3S,αR-enantiomer (S).G. Davies and I. A. S. Walters, J. Chem. Soc. Perkin Trans.I, 1129–1139 (1994).

Step B: Methyl(2S,3R)-3-amino-2-methyl-3-phenylpropionate: A mixture of methyl(2S,3R,αS)-3-(N-benzyl-N-αmethylbenzylamino)-2-methyl-3-phenylpropionate (13.0 g, 33.55 mmol) and 10% palladium-on-carbon (13.0 g) in glacial acetic acid (260 ml) was hydrogenated under a balloon of hydrogen for 24 h. The catalyst was removed by filtration followed by evaporation and co-distillation with toluene to provide the title compound as a white solid. MS (m/z): 194.2 (M+H)$^+$; $C_{11}H_{15}NO_2$ requir. 193.3.

Step C: (2S,3R)-3-Amino-2-methyl-3-phenylpropionamide: A solution of methyl(2S,3R)-3-amino-2-methyl-3-phenylpropionate (6.3 g, 33 mmol) in 2N methanolic ammonia (20 ml) and ammonium hydroxide (28–30%, 40 ml) was stirred at room temperature. After 4d, concentration followed by chromatography on a short column of silica gel (dichloromethane-methanol-conc. ammonium hydroxide= 93:7:0.7; 90:10:0.8) provided the amide as a white solid. MS (m/z): 179.2 (M+H)$^+$; $C_{10}H_{14}N_2$O requir. 178.2.

Step D: (1R,2R)-2-methyl-1-phenyl-1,3-propanediamine: Lithium aluminium hydride (2.3 g, 60.60 mmol) was added in portions to a stirring solution of (2S,3R)-3-amino-2-methyl-3-phenylpropionamide (2.6 g, 14.59 mmol) in tetrahydrofuran (54 ml) at ice-bath temperature. After 45 min, the mixture was heated at reflux for 16 h. With ice-bath cooling, the reaction was quenched by the portionwise addition of sodium sulfate decahydrate and some methanol until hydrogen evolution ceased. The solids were removed by filtration and washed with dichloromethane. The combined filtrates were evaporated to provide the title compound. MS (m/z): 165.2 (M+H)$^+$; $C_{10}H_{16}N_2$ requir. 164.3.

EXAMPLE 1P

Procedure for the Preparation of (1S,2S)-2-methyl-1-phenyl-1,3-propanediamine

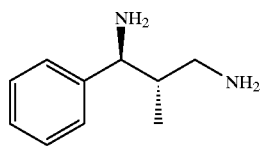

The title compound was prepared as described in the example for the synthesis of the enantiomer, (1R,2R)-2-methyl-1-phenyl-1,3-propanediamine, from methyl(2R,3S,αR)-3-(N-benzyl-N-α-methylbenzylamino)-2-methyl-3-phenylpropionate (Davies et al., J. Chem. Soc. Chem. Commun. 1153–1155, 1993). The title compound was obtained as a crystallizing oil, MS (m/z): 165.3 (M+H)$^+$; $C_{10}H_{16}N_2$ requir. 164.3.

EXAMPLE 1Q

Procedure for the Preparation of 3-phenyl-2,2-dimethyl-1,3-propanediamine

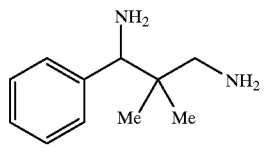

The title compound was prepared according to the procedure described in: W. Ten Hoeve and H. Wynberg, Synth. Commun. 24 (15), 2215–2221, 1994, MS (m/z): 179.1 (M+H)$^+$; $C_{11}H_{18}N_2$ requir. 168.1.

EXAMPLE 1R

Procedure for the Preparation of 3-phenyl-2,2-dimethyl-1-aminopropane

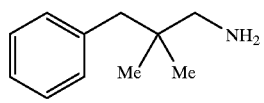

Step A: of 2,2-dimethyl-3-phenyl-1-azidopropane
Diisopropyl azodicarboxylate ( 19.7 mL, 100 mmol) was added dropwise to a stirred mixture of 2,2-dimethyl-3-phenyl-1-propanol (8.2 gm, 50 mmol), triphenylphosphine (26.2 gm, 100 mmol), and Zn(N$_3$)$_2$.2 pyridine (11.5 gm, 37.5 mmol) in toluene (250 mL). [reference: Synthesis, (1990) page 131] After 2.5 h, celite (25 gm) was added, and the mixture was filtered and concentrated to an oil. Purification (SiO$_2$, 40% EtOAc/hexanes) gave the step A product as an oil.

Step B: of 2,2-dimethyl-3-phenyl-1-aminopropane
A mixture of 2,2-dimethyl-3-phenyl-1-azidopropane (3 gm), 10% Pd-C, methanol (60 mL) and tetrahydrofuran (15 mL) was stirred under 1 atmosphere of hydrogen at rt for 18 h. The mixture was filtered and concentrated to give the title compound as an oil, MS (m/z): 164.1 (M+H)$^+$; $C_{11}H_{17}N$ requir. 163.1.

EXAMPLE 1S

Procedure for the Preparation of 1-(aminomethyl)-2-benzylcyclopentane

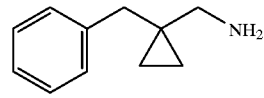

Step A: 1-benzyl-1-cyclopropanecarbonitrile: A solution of cyclopropyl cyanide (3.0 mL, 40 mmol) in 20 mL THF was dropwise added to a stirred, freshly prepared, mixture of lithium diisopropylamide (40 mmol) in THF (100 mL) at −78° C. After 30 min, a solution of benzyl bromide 7.8 mL, 60 mmol) in THF (20 mL) was dropwise added. The resulting mixture was warmed slowly over several hrs and stirred at rt 48 hr. The reaction was quenched (250 mL saturated NH$_4$Cl), extracted with ether (3×100 mL) and the combined organic extracts were dried (MgSO$_4$), filtered and concentrated to afford a yellow oil.

Step B: 1-(aminomethyl)-2-benzylcyclopentane
A solution of 1-benzyl-1-cyclopropanecarbonitrile (9.16 gm, 58 mmol), 10% Pd-C (1.5 gm), in MeOH (200 mL), THF (50 mL), and conc.HCl (6 mL) was shaken under a hydrogen atmosphere (50 psi) for 15 hr. The mixture was concentrated, water (300 mLO was added and made basic (pH 10–11) with 2N NaOH. The mixture was extracted with EtOAc (2×100 mL), the combined organic layers were dried (MgSO$_4$), filtered and concentrated to provide the title compound.

EXAMPLE 2

Procedure for the Preparation of 6-bromo-[2,4']bipyridine

Step A: pyridine-4-boronic acid: 4-bromopyridine hydrochloride (19.46 gm, 0.1 mole) was neutralized with 60 mL of 2 M aqueous Na$_2$CO$_3$ and extracted with ether (200 mL). The dried (MgSO$_4$) organic layer was concentrated to obtain 4-bromopyridine which was dropwise added to a cooled (−78° C.) stirred solution of t-butyllithium (88 mL, 1.7 M in hexanes) in ether (150 mL). 30 min after complete addition, triisopropyl borate (22 mL, 0.2 mole) was dropwise added. The reaction mixture was warmed to rt and quenched with 50% aqueous methanol (40 mL), followed by water (100 mL). Acidification of the mixture with conc HCl (to pH 5.5–6.0) provided a white precipitate which was collected by filtration and rinsed (H$_2$O) and dried to give pyridine-4-boronic acid.

Step B: 6-bromo-[2,4']bipyridine: Dry N$_2$ was bubbled through a stirred solution of 2,6-dibromopyridine (1.6 gm, 6.7 mmole), pyridine-4-boronic acid (317 mg, 2.6 mmol), and Pd(PPh$_3$)$_4$ (160 mg) in aqueous 2M Na$_2$CO$_3$ (8 mL) and toluene (8 mL) at rt for 20 min. The reaction mixture was then heated to reflux for 10 hr. After cooling to rt CH$_2$Cl$_2$ (100 mL) was added and the mixture was washed with brine and dried (Na$_2$SO$_4$). Purification (Sio$_2$, CH$_2$Cl$_2$/MeOH/NH$_4$OH: 100/11/8) gave 6-bromo-[2,4']bipyridine. MS (m/z): Calcd. C$_{10}$H$_7$N$_2$Br (M$^+$): 235, found: 234.9.

EXAMPLE 3

General Procedure for the Preparation of 6-alkylamino-3-bromo-2-(4-pyridyl)pyridines

EXAMPLE 3A

Preparation of 6-((S)-2-Amino-3-phenylpropylamino)-3-bromo-2-(4-pyridyl)pyridine

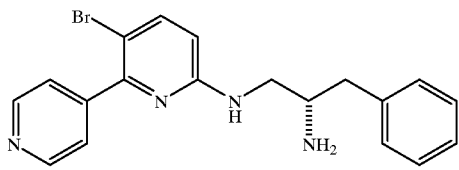

Step A: Preparation of 6-((S)-2-Amino-3-phenylpropylamino)-2-(4-pyridyl)pyridine: A neat mixture of 6-bromo-[2,4']bipyridine (2.35 gm, 10 mmole) and (S)-2-amino-3-phenylpropylamine (3 gm, 20 mmole) was heated to 190° C. for 4 hr. The reaction was cooled to rt and purified (SiO$_2$, CH$_2$Cl$_2$/MeOH/NH$_4$OH: 100/11/8) to give the step 1 compound. (This reaction provides major products wherein the less hindered amine functionality displaces the bromide,when the nucleophile is an alkyldiamine) MS (m/z): Calcd. C$_{19}$H$_{20}$N$_4$ (M$^+$): 304, found (M+H)$^+$: 305.2.
Step B: Preparation of 6-((S)-2-Amino-3-phenylpropylamino)-3-bromo-2-(4-pyridyl)pyridine: A mixture of bromine (1.6 gm, 10 mmole) and HOAc (10 mL) was added in three portions to a stirred solution of 6-((S)-2-Amino-3-phenylpropylamino)-2-(4-pyridyl)pyridine (3.04 gm, 10 mmole) in HOAc (20 mL) at rt. After 1 hr, the mixture was concentrated and purified (SiO$_2$, CH$_2$Cl$_2$/MeOH/NH$_4$OH: 100/11/8) to give 6 -((S)-2-Amino-3-phenylpropylamino)-3-bromo-2-(4-pyridyl)pyridine. MS (m/z): Calcd. C$_{19}$H$_{19}$N$_4$Br (M$^+$): 383, found : 383.1 and 385.1.
The following compounds (derivatives of 3-bromopyridine) may be prepared according to the procedure set forth in Example 3A, using the appropriate amine in Step A, followed by bromination as in Step B.

EXAMPLE 3B 6-(3-phenylpropylamino)-3-bromo-2-(4-pyridyl)pyridine

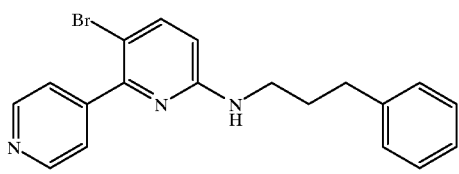

EXAMPLE 3C 6-((R,S)-2-methyl-3-phenylpropylamino)-3-bromo-2-(4-pyridyl)pyridine

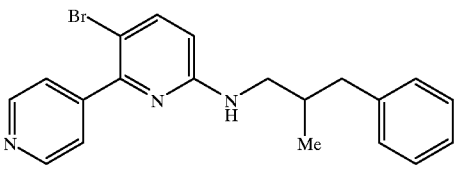

EXAMPLE 3D 6-(2,2-dimethyl-3-phenylpropylamino)-3-bromo-2-(4-pyridyl)pyridine

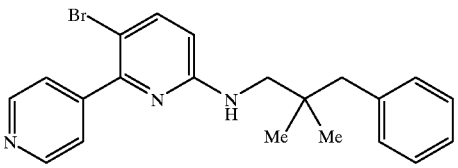

EXAMPLE 3E 6-((R,S)-3-amino-2,2-dimethyl-3-phenylpropylamino)-3-bromo-2-(4-pyridyl)pyridine

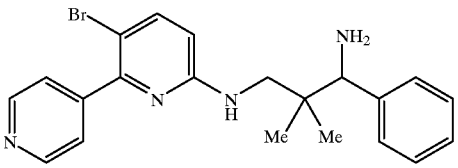

EXAMPLE 3F 6-((R,S)-3-amino-3-phenylpropylamino)-3-bromo-2-(4-pyridyl)pyridine

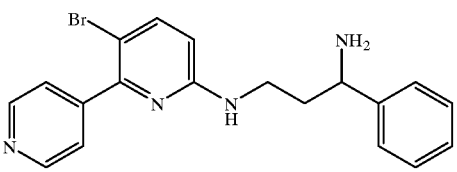

EXAMPLE 3G 6-((R,S)-3-amino-3-(2-chlorophenyl)propylamino)-
3-bromo-2-(4-pyridyl)pyridine

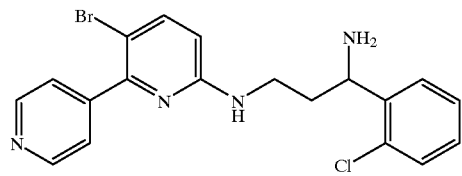

EXAMPLE 3H 6-((R,S)-3-amino-3-(2-fluorophenyl)propylamino)-
3-bromo-2-(4-pyridyl)pyridine

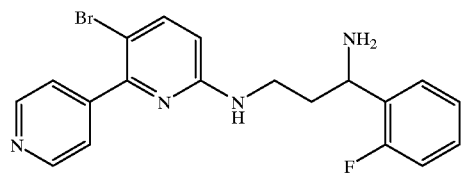

EXAMPLE 3I 6-((R,S)-3-amino-3-(2-methylphenyl)propylamino)-
3-bromo-2-(4-pyridyl)pyridine

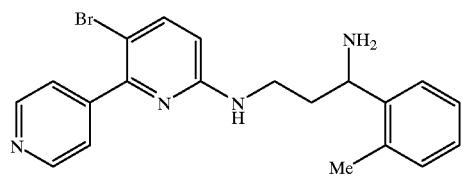

EXAMPLE 3J 6-((S)-2-methyl-(R)-3-amino-3-phenylpropylamino)-
3-bromo-2-(4-pyridyl)pyridine

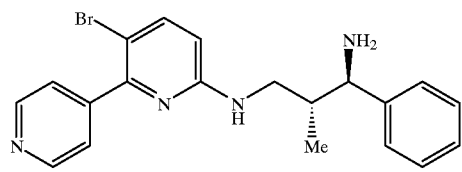

EXAMPLE 3K 6-(1,2,3,4-tetrahydroisoquinolinyl-3-methylamino)-
3-bromo-2-(4-pyridyl)pyridine

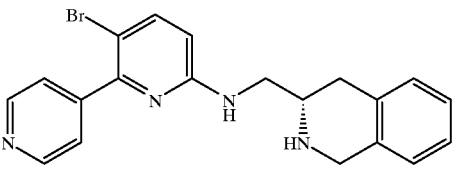

EXAMPLE 3L 6-(N-(3-benzylpiperazin-1-yl)-3-bromo-2-(4-
pyridyl)pyridine

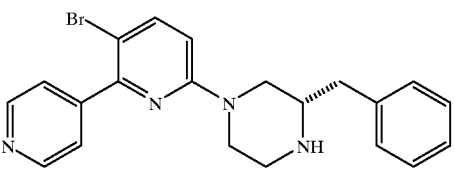

EXAMPLE 4

General Procedure for the Preparation of 6-
alkylamino-3-aryl-2-(4-pyridyl)pyridines

EXAMPLE 4A

Preparation 6-((S)-2-Amino-3-phenylpropylamino)-
3-(3-methylphenyl)-2-(4-pyridyl)pyridine

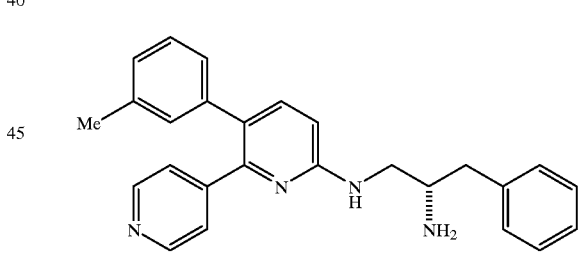

To a stirred, degassed mixture of 6-((S)-2-Amino-3-phenylpropylamino)-3-bromo-2-(4-pyridyl)pyridine (4.2 gm, 10.9 mmole), 3-methylbenzene boronic acid (1.8 gm, 13 mmole), in aqueous 2 M $Na_2CO_3$ (50 mL) and toluene (50 mL) at rt was added $Pd(PPh_3)_4$ (400 mg, 0.35 mmole). The mixture was heated to reflux for 12 hrs, cooled to rt, and extracted with toluene. The combined organic layers were washed with brine, concentrated and purified ($SiO_2$, $CH_2Cl_2$/MeOH/$NH_4OH$: 100/11/8) to give the title compound. MS (m/z): Calcd. $C_{26}H_{26}N_4$ ($M^+$): 394, found $(M+H)^+$: 395.1.

The following compounds were prepared according to the procedure set forth in Example 4A, using the appropriate boronic acid and using the 3-bromopyridine derivative (whose preparation is described in Example 3).

EXAMPEL 4B 6-((S)-2-Amino-3-phenylpropylamino)-3-(3-trifluoromethylphenyl)-2-(4-pyridyl)pyridine MS (m/z): Calcd. $C_{26}H_{23}N_4F_3$ (M+): 448, found (M+H)+: 449.3.

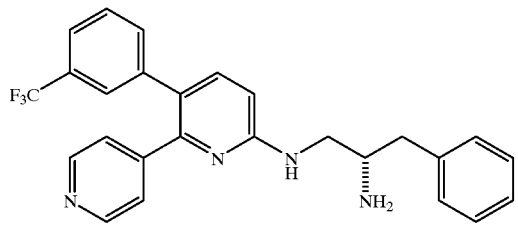

EXAMPLE 4C 6-((S)-2-Amino-3-phenylpropylamino)-3-(2-napthyl)-2-(4-pyridyl)pyridine MS (m/z): Calcd. $C_{29}H_{26}N_4$ (M+): 431, found (M+H)+: 431.5.

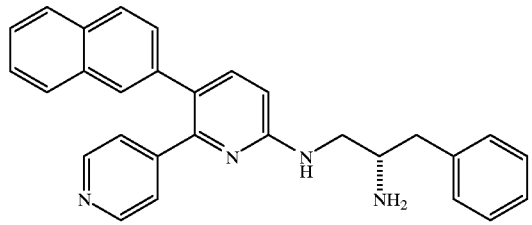

EXAMPLE 4D 6-((S)-2-Amino-3-phenylpropylamino)-3-(4-chlorophenyl)-2-(4-pyridyl)pyridine MS (m/z): Calcd. $C_{25}H_{23}N_4Cl$ (M+): 414, found (M+H)+: 415.4.

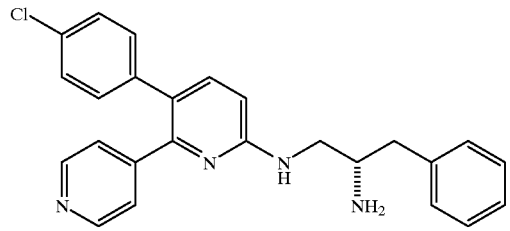

EXAMPLE 4E 6-((S)-2-Amino-3-phenylpropylamino)-3-(3-isopropylphenyl)-2-(4-pyridyl)pyridine MS (m/z): Calcd. $C_{28}H_{30}N_4$ (M+): 422, found (M+H)+: 423.2.

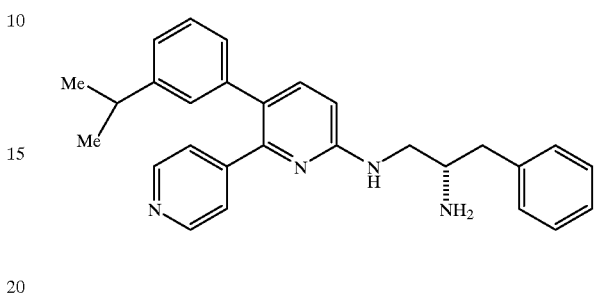

EXAMPLE 4F 6-((S)-2-Amino-3-phenylpropylamino)-3-(4-methoxyphenyl)-2-(4-pyridyl)pyridine MS (m/z): Calcd. $C_{26}H_{26}ON_4$ (M+): 410, found (M+H)+: 411.3

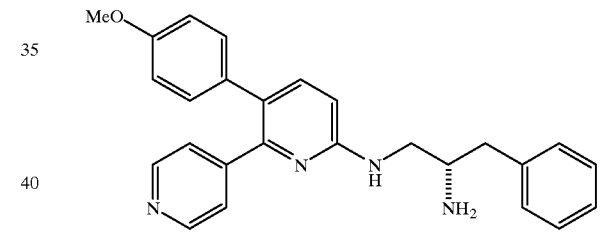

EXAMPLE 4G 6-((S)-2-Amino-3-phenylpropylamino)-3-(4-chloro-3-fluorophenyl)-2-(4-pyridyl)pyridine MS (m/z): Calcd. $C_{25}H_{22}N_4FCl$ (M+): 432, found (M+H)+: 433.3

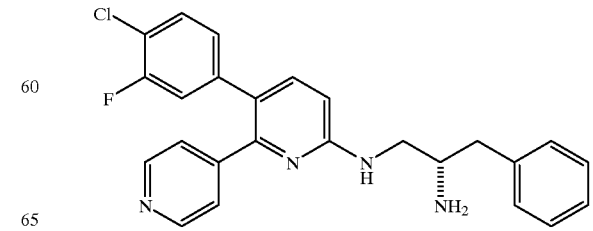

EXAMPLE 4H 6-((S)-2-Amino-3-phenylpropylamino)-3-(2-benzothiophenyl)-2-(4-pyridyl)pyridine MS (m/z): Calcd. $C_{27}H_{24}N_4S$ (M$^+$): 436, found (M+H)$^+$: 437.5

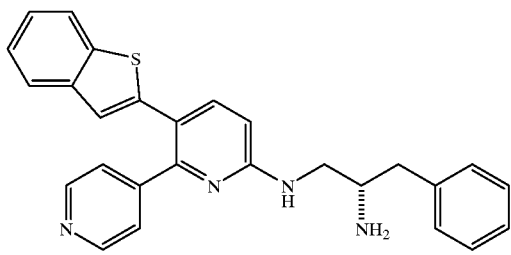

The following compounds can be prepared according to the procedure set forth in Example 4A, using the appropriate boronic acid and using the 3-bromopyridine derivative (whose preparation is described in Example 3).

EXAMPLE 4I

6-((S)-2-Amino-3-phenlpropylamino)-3-(3-fluorophenyl)-2-(4-pyridyl)pyridine

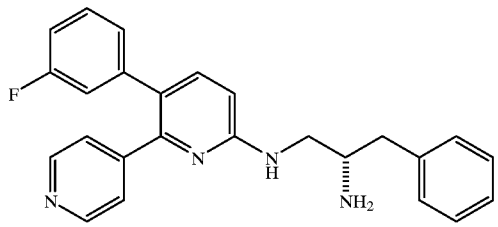

EXAMPLE 4J 6-((S)-2-Amino-3-phenylpropylamino)-3-(4-fluorophenyl)-2-(4-pyridyl)pyridine

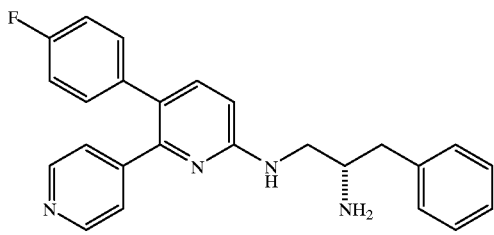

EXAMPLE 4K 6-(3-Amino-3-phenylpropylamino)-3-(3-methylphenyl)-2-(4-pyridyl)pyridine

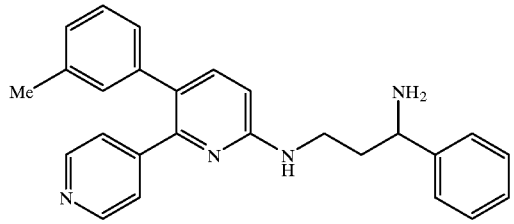

EXAMPLE 4L 6-(3-Amino-3-phenylpropylamino)-3-(4-fluorophenyl)-2-(4-pyridyl)pyridine

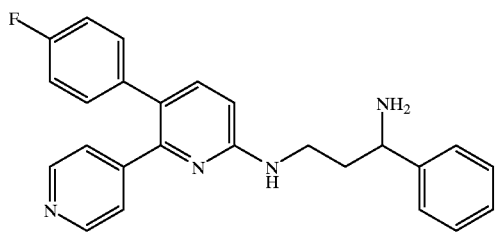

EXAMPLE 4M 6-(3-Amino-3-phenylpropylamino)-3-(3-trifluoromethylphenyl)-2-(4-pyridyl)pyridine

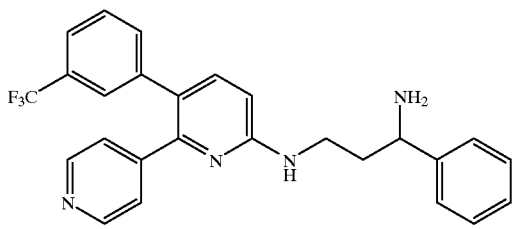

EXAMPLE 4N 6-(3-Amino-3-phenylpropylamino)-3-(2-benzothiophenyl)-2-(4-pyridyl)pyridine

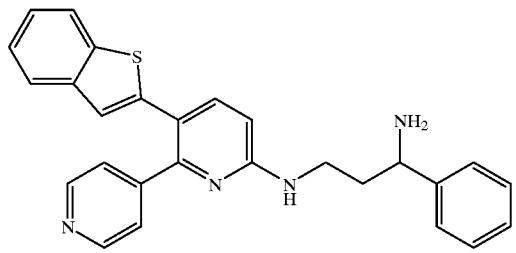

EXAMPLE 4O 6-(3-amino-2,2-dimethyl-3-phenylpropylamino)-(3-methylphenyl)-2-(4-pyridyl)pyridine

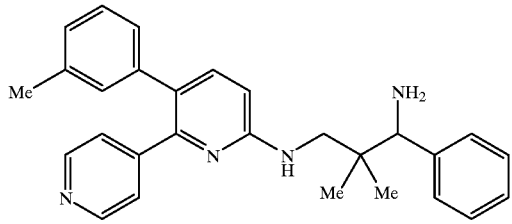

EXAMPLE 4P 6-(3-amino-2,2-dimethyl-3-phenylpropylamino)-(4-fluorophenyl)-2-(4-pyridyl)pyridine

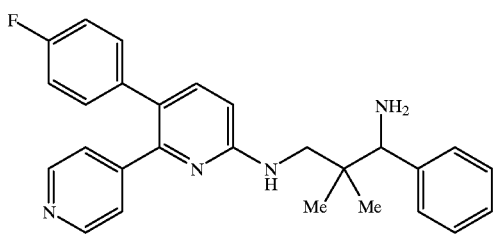

EXAMPLE 4Q 6-(3-amino-2,2-dimethyl-3-phenylpropylamino)-(4-chloro-3-fluorophenyl)-2-(4-pyridyl)pyridine

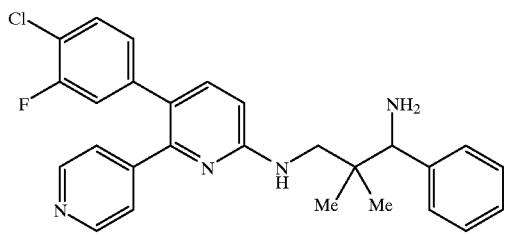

EXAMPLE 4R 6-(3-amino-2,2-dimethyl-3-phenylpropylamino)-(2-benzothiophenyl)-2-(4-pyridyl)pyridine

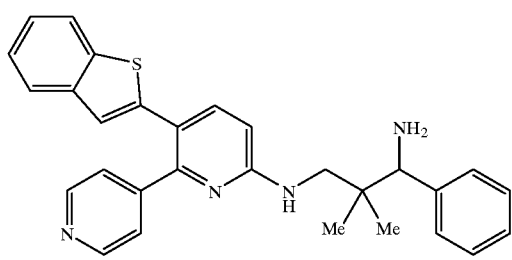

EXAMPLE 4S 6-(3-amino-3-(2-chlorophenyl)propylamino)-(3-methylphenyl)-2-(4-pyridyl)pyridine

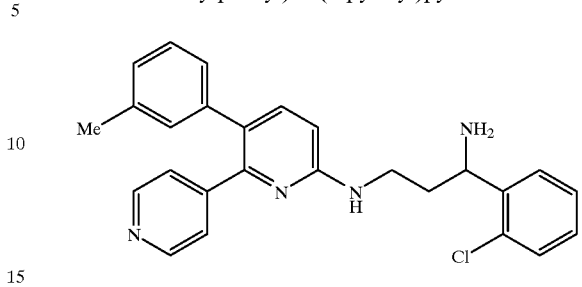

EXAMPLE 4T 6-(3-amino-3-(2-chlorophenyl)propylamino)-(4-fluorophenyl)-2-(4-pyridyl)pyridine

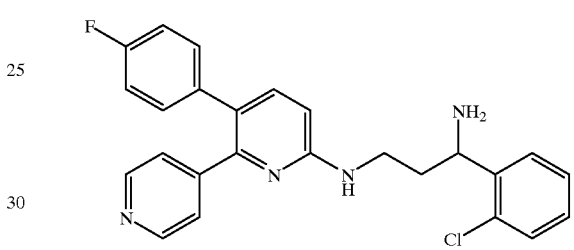

EXAMPLE 4U 6-(3-amino-3-(2-fluorophenyl)propylamino)-3-(3-methylphenyl)-2-(4-pyridyl)pyridine

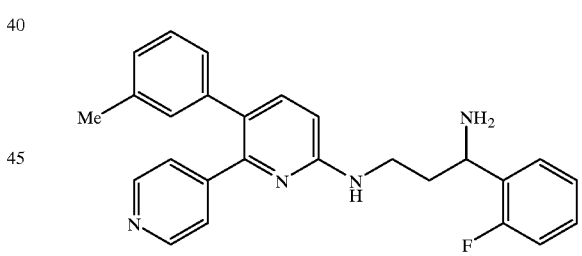

EXAMPLE 4V 6-(3-amino-3-(2-methylphenyl)propylamino)-3-(3-trifluoromethylphenyl)-2-(4-pyridyl)pyridine

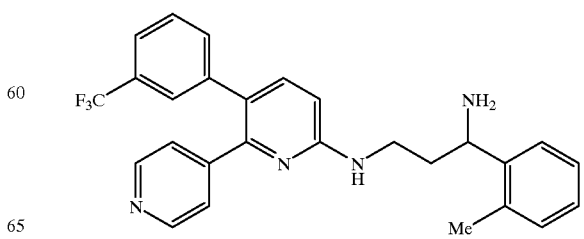

EXAMPLE 4W 6-((S)-2-methyl-(R)-3-amino-3-phenylpropylamino)-
3-(4-fluorophenyl)-2-(4-pyridyl)pyridine

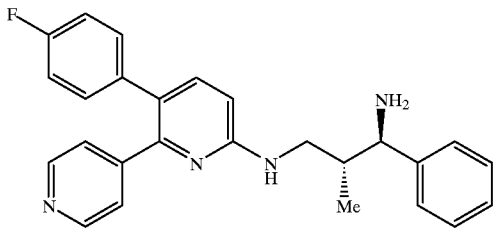

EXAMPLE 4X 6-((S)-2-methyl-(R)-3-amino-3-phenylpropylamino)-
3-(3-methylphenyl)-2-(4-pyridyl)pyridine

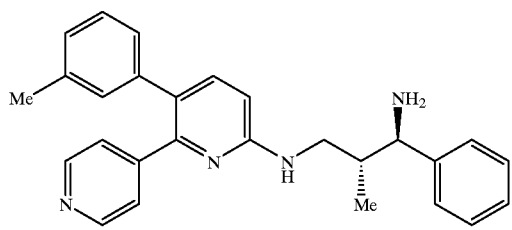

EXAMPLE 4Y 6-(1,2,3,4-tetrahydroisoquinolinyl-3-methylamino)-
3-(3-chloro-4-fluorophenyl)-2-(4-pyridyl)pyridine

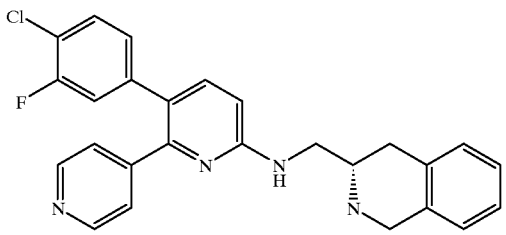

EXAMPLE 4Z 6-(N-(3-benzylpiperazin-1-yl)-3-(4-fluorophenyl)-2-
(4-pyridyl)pyridine

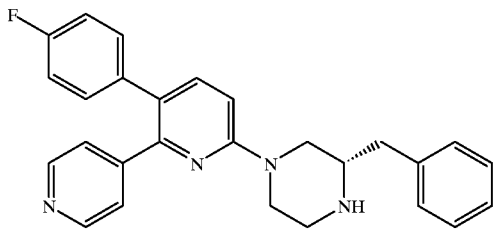

EXAMPLE 5

Procedure for the Preparation of 6-(4-
Fluorophenyl)-5-(4-pyridyl)-2H-pyridazin-3-one

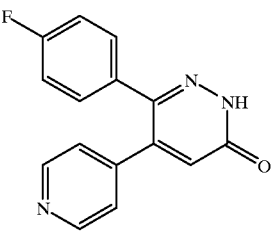

Step A: Ethyl 3-(4-fluorobenzoyl)-3-(4-pyridyl)-propionate: Sodium (400 mg, 17.40 mmol) was added to a stirred solution of 1-(4-fluorophenyl)-2-(4-pyridyl)ethanone (3.35 g, 15.58 mmol) (P. J. Gilligan et al., J. Med. Chem. 35, 4344, 1992) in ethanol (50 ml) at room temperature. After dissolution of the sodium, ethyl bromoacetate (1.93 ml, 17.40 mmol) was added dropwise at ice-bath temperature. After stirring for 4 h at room temperature, the reaction mixture was concentrated by evaporation. It was diluted with dichloromethane and made neutral by washing with diluted acetic acid followed by drying of the organic solution and evaporation. Flash chromatography (hexane-acetone=3:1,2:1) provided the title compound as a syrup. MS (m/z): 302.2 (M+H)$^+$; $C_{17}H_{16}FNO_3$ requir. 301.3.

Step B: 6-(4-Fluorophenyl)-4,5-dihydro-5-(4-pyridyl)-2H-pyridazin-3-one: A solution of ethyl 3-(4-fluorobenzoyl)-3-(4-pyridyl)-propionate (1.0 g, 3.32 mmol) and hydrazine monohydrate (1 ml, 20.6 mmol) in ethanol (1 ml) was refluxed for 2.5 h. The solvent and hydrazine monohydrate were evaporated. The remainder was taken up in n-butanol and the mixture was heated at reflux for 45 min. Evaporation was followed by column chromatography on silica gel (3–7.5% methanol/dichloromethane) to provide the title compound. MS (m/z): 270.2 (M+H)$^+$; $C_{15}H_{12}FN_3O$ requir. 269.3.

Step C: 6-(4-Fluorophenyl)-5-(4-pyridyl)-2H-pyridazin-3-one: A solution of bromine (78.3 µl, 1.48 mmol) in acetic acid (6 ml) was added dropwise to a stirred solution of 6-(4-fluorophenyl)-4,5-dihydro-5-(4-pyridyl)-2H-pyridazin-3-one (314 mg, 1.17 mmol) in acetic acid (4.6 ml) at room temperature. After 2 h at room temperature, more bromine (41.7 µl, 0.78 mmol) in acetic acid (3.2 ml) was added to the turbid mixture. A gum precipitated. After 30 minutes, it was evaporated and co-evaporated with toluene. Residual acid was neutralized with methanolic 2N ammonia followed by evaporation. The resulting product was purified on a column of silica gel (3–5% methanol/dichloromethane) to provide the title compound as a solid. MS (m/z): 268.1 (M+H)$^+$; $C_{15}H_{16}FN_3O$ requir. 267.3.

EXAMPLE 6

Procedure for the Preparation of 6-[((S)-2-amino-3-phenylpropyl)-amino]-3-(4-fluorophenyl)-4-(4-pyridyl)pyridazine

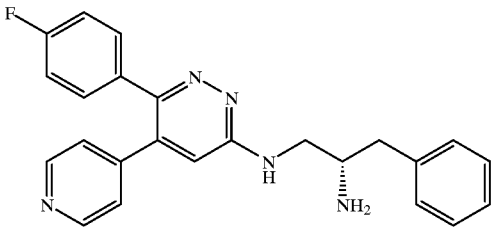

Step A: 6-Chloro-3-(4-fluorophenyl)-4-(4-pyridyl) pyridazine: A stirred mixture of 6-(4-fluorophenyl)-5-(4-pyridyl)-2H-pyridazin-3-one (105 mg, 0.40 mmol) and phosphorus oxychloride (2 ml) was heated at reflux for 2 h. It was evaporated, followed by co-evaporation with toluene and drying of the resultant product in an oil pump vacuum for several hours. Then dichloromethane was added and dil. ammonium hydroxide to neutrality with cooling. The organic solution was washed with water, dried and evaporated to leave the title compound. MS (m/z): 286.0 (M)$^+$; $C_{15}H_9ClFN_3$ requir. 285.7.

Step B: 6-[((S)-2-amino-3-phenylpropyl)-amino]3-(4-fluorophenyl)-4-(4-pyridyl)-pyridazine: A stirred mixture of 6-chloro-3-(4-fluorophenyl)-4-(4-pyridyl)pyridazine (102 mg, 0.36 mmol) and (S)-1,2-benzylethylendiamine (200 μl, ~1.3 mmol) was heated at 160° C. for 2 h. The resultant product was applied to a column of silica gel (dichloromethane-methanol=93:7; dichloromethane-methanol-conc. ammonium hydroxide=93:7:0.7) to provide the title compound. MS (m/z): 400.1 (M+H)$^+$; $C_{24}H_{22}FN_5$ requir. 399.5.

EXAMPLE 7

Procedure for Preparation of 2-((S)-2-amino-3-phenylpropylamino)-5-(3-methylphenyl)-4-(4-pyridyl)pyridine

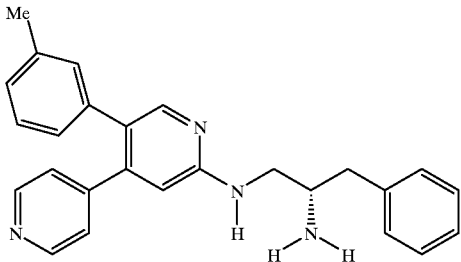

Step A: Preparation of 4-(tert-butyl-dimethyl-silanyloxymethyl)-pyridine: To a stirred solution of 4-pyridylcarbinol (21.8 g, 0.20 mole) in DMF (200 mL) at 25° C. was added imidazole (15.64 g, 0.23 mole) and t-butyldimethylsilyl chloride (31.65 g, 0.21 mole). The reaction mixture was allowed to stirred at that temperature for 3 hr. Standard aqueous work up (ethyl acetate extraction, washed with water and brine, dried with $MgSO_4$, evaporation), followed by chromatographic purification (silica gel, hexane/ethyl acetate) gave the title compound. $^1$H-NMR (CDCl$_3$, 400 MHz) δ: 8.50(d, 2H), 7.25(d, 2H), 4.86(s, 2H), 0.90(s, 9H), 0.05(s, 6H).

Step B: Preparation of 2-(tert-butyl-dimethyl-silanyloxy)-2-pyridine-4-yl-1-m-tolyl-ethanol: To a solution of 4-(tert-butyl-dimethyl-silanyloxymethyl)-pyridine (5 g, 22 mmole) in THF (100 mL) at −20° C. was added LDA (2M, 13.2 mL, 26.4 mmole) dropwise. The mixture was stirred at that temperature for 1 hr before addition of 3-methylbenalhehyde (2.9 g, 24 mmole) in THF (20 mL). The reaction was then warmed up to r. t. for additional 1 hr. The mixture was diluted with EtOAc, washed with NH$_4$Cl and brine, dried with MgSO$_4$, evaporarted and, finally, purified on column (silica gel, hexane/ethyl acetate) to give the title compound.

Step C: Preparation of 1-pyridine-4-yl-2-m-tolyl-ethane-1,2-diol: To a solution of 2-(tert-butyl-dimethyl-silanyloxy)-2-pyridine-4-yl-1-m-tolyl-ethanol (5 g, 14.5 mmole) in THF (50 mL) was added t-butylamonium fluoride (1M, 16 mL, 16 mmole) at 25° C. The solution was stirred at that temperature for 1 hr before evaporation of solvent and purification (silica gel, hexane/ethyl acetate) to give the title compound. MS (m/z): Calcd. $C_{14}H_{15}NO_2(M^+)$: 229, found (M+H)$^+$: 230.1, (M−H)$^−$: 228.1

Step D: Preparation of 1-pyridine-4-yl-2-m-tolyl-ethane-1,2-dione: Dimethylsufoxide (2.85 mL, 40 mmole) was dropwise added into a solution of trifluoroacetic anhydride (4.24 mL, 30 mmole) in methylene chloride (100 mL) at 78° C. The reaction mixture was stirred at that temperature for 10 min before the addition of 1-pyridine-4-yl-2-m-tolyl-ethane-1,2-diol (2.29 g, 10 mmole) in methylene chloride (50 mL). The mixture was stirred additional 1 hr at that temperature. Finally, the mixture was quenched with triethylamine (8.5 mL, 60 mmole) and the resulting mixture was allowed to warmed to r.t. The reaction was diluted with methylene chloride, washed with NH$_4$Cl and brine, dried with MgSO$_4$, evaporated, and finally, purified through a silica column (ethyl acetate/hexane) to give the title compound. MS (m/z): Calcd. $C_{14}H_{11}NO_2(M^+)$: 225, found (M+H)$^+$: 226.1.

Step E: Preparation of 4-hydroxy-3-pyridine-4-yl-4-m-tolyl-cyclopent-2-en-1-one: To a solution of 1-pyridine-4-yl-2-m-tolyl-ethane-1,2-dione (1.8 g, 8.0 mmole) in acetone (20 mL) was added crushed KOH (448 mg, 8.0 mmole) in one portion at r.t. The reaction mixture was stirred at that temperature for 1 hr before quenching the reaction with aqueous NH$_4$Cl. Standard aqueous work up, followed by chromatographic purification (silica gel, hexane/ethyl acetate) gave the a mixture of the title compound and the regiosiomer, 4-hydroxy-4-pyridine-4-yl-3-m-tolyl-cyclopent-2-en-1-one. MS (m/z): Calcd. $C_{17}H_{15}NO_2(M^+)$: 265, found (M+H)$^+$: 265.9.

Step F: Preparation of 4-acetoxy-3-pyridine-4-yl-4-m-tolyl-cyclopent-2-en-1-one: To a solution of 4-hydroxy-3-pyridine-4-yl-4-m-tolyl-cyclopent-2-en-1-one and it's regioisomer (265 mg, 1.0 mmole) in methylene chloride (5 mL) was added dimethylamino pyridine (183 mg, 1.5 mmole) and acetic anhydride (0.12 mL, 1.2 mmole) at r.t. The reaction mixture was stirred at that temperature for 1 hr before quenching the reaction with 1 mL of methanol. Concentration and purification (silica, hexane/ethyl acetate) gave the title compound as the faster eluting isomer. MS (m/z): Calcd. $C_{19}H_{17}NO_3(M^+)$: 307, found (M+H)$^+$: 308.1.

Step G: Preparation of 1-acetoxy-4-hydroxyimino-2-pyridine-4-yl-1-m-tolyl-cyclopent-2-ene: To a solution 4-acetoxy-3-pyridine-4-yl-1-m-tolyl-cyclopent-2-en-1-one (307 mg, 1.0 mmole) in ethanol (10 mL) was added hydroxylamine hydrochloride (105 mg, 1.5 mmole) and pyridine (5 drops) at r. t. The reaction mixture was heated to 70° C. for 3 hr before cooling down to r.t. Concentration and purification (silica gel, hexane/ethyl acetate) gave the title compound. MS (m/z): Calcd. $C_{19}H_{18}N_2O_3(M^+)$: 322, found (M+H)$^+$: 323.2.

Step H: Preparation of 5-acetoxy-5-m-tolyl-5,6-dihydro-1H-[4,4']bipyridinyl-2-one: To a solution of 1-acetoxy-4-hydroxyimino-2-pyridine-4-yl-1-m-tolyl-cyclopent-2-ene (322 mg, 1.0 mmole) in methylene chloride (10 mL) at r.t. was added $PCl_5$ (417 mg, 2.0 mmole) in one portion. The reaction mixture was stirred at that temperature for 1 hour before quenching the reaction with sodium bicarbonate solution. Stanard basic work up, followed by purification gave the title compound. MS (m/z): Calcd. $C_{19}H_{18}N_2O_3$ ($M^+$): 322, found $(M+H)^+$: 322.9.

Step I: Preparation of 5-hydroxy-5-m-tolyl-5,6-dihydro-1H-[4,4']bipyridinyl-2-one: To a solution of 5-acetoxy-5-m-tolyl-5,6-dihydro-1H-[4,4']bipyridinyl-2-one (322 mg, 1.0 mmole) in THF (5 mL) and water (5 mL) at r.t. was added LiOH (126 mg, 3.0 mmole) in one portion. The reaction mixture was stirred at that temperature for 1 hr before quenching the mixture with aqueous $NH_4Cl$. Standard work up (extraction of compound with methylene chloride), followed by purification (methano/methylene chloride) gave the title compound. MS (m/z): Calcd. $C_{17}H_{16}N_2O_2(M^+)$: 280, found $(M+H)^+$: 281.0.

Step J: Preparation of 5-m-tolyl-1H-[4,4']bipyridinyl-2-one: To a solution of 5-hydroxy-5-m-tolyl-5,6-dihydro-1H-[4,4']bipyridinyl-2-one (280 mg, 1.0 mmole) in $CHCl_3$ (5 mL) at r.t. was added 1 ml of conc. $H_2SO_4$. The resulting mixture was heated to 55° C. for 1 hr. The mixture was cooled down to r.t. and was carefully quenched with aqueous sodium carbonate. Standard work up (extraction of compound with methylene chloride), followed by purification (silica gel, methanol/methylene chloride) gave the title compound. MS (m/z): Calcd. $C_{17}H_{14}N_2O(M^+)$: 262, found $(M+H)^+$: 263.3.

Step K: Preparation of 2-chloro-5-(3-methylphenyl)-4-(4-pyridyl)pyridine: 5-m-tolyl-1H-[4,4']bipyridinyl-2-one (262 mg, 1.0 mmole) in $POCl_3$ (5 mL) was heated to 105° C. for 12 hr. $POCl_3$ was removed under reduced pressure. The residue was diluted with methylene chloride and was carefully quenched with aqueous sodium carbonate. Standard work up, followed by purification (silica gel, hexane/ethyl acetate) gave the title compound. MS (m/z): Calcd. $C_{17}H_{13}N_2Cl$ ($M^+$): 280.5, found $(M+H)^+$: 281.0 and 283.1.

Step L: Preparation of 2-((S)-2-amino-3-phenylpropylamino)-5-(3-methylphenyl)-4-(4-pyridyl)pyridine: A mixture of 2-chloro-5-(3-methylphenyl)-4-(4-pyridyl)pyridine (281 mg, 1.0 mmole) and (S)-1,2-benzylethylenediamine (375 mg, 2.5 mmole) was heated to 160° C. for 5 hr. The mixture was cooled down and was added 2 mL of methylene chloride. The resulting mixture was subjected to chromatographic purification (silica gel, methanol/methylene chloride) to give the title compound. MS (m/z): Calcd. $C_{26}H_{26}N_4$ ($M^+$): 394, found $(M+H)^+$: 395.1

EXAMPLE 8

An alternative procedure for the preparation 2-((S)-2-amino-3-phenylpropylamino)-5-(3-methylphenyl)-4-(4-pyridyl)pyridine Step A: Preparation of 2-((S)-2-amino-3-phenylpropylamino)-4-(4-pyridyl)pyridine: A mixture of 2-chloro-[4,4']-bipyridine (Moran, D. B. et al, *J. Heterocyclic Chem.* 1986, 23, 1071) (1 g, 5.26 mmole) and (S)-1,2-benzylethylenediamine (1.8 g, 12 mmole) was heated to 190° C. for 3 hr. The mixture was cooled down to room temperature and was subjected to chromatographic purification (20% MeOH in $CH_2Cl_2$) to give the title compound. MS (m/z): Calcd. $C_{19}H_{20}N_4$ ($M^+$): 304, found $(M+H)^+$: 305.4. $^1$H-NMR ($CDCl_3$, 400 MHz) δ: 8.60(d, 2H), 8.0(d, 1H), 7.38–7.10(m, 5H), 7.26(d, 2H), 6.62(d, 1H), 6.45(s, 1H), 5.82(bs, 1H), 3.70–3.40(m, 3H), 2.95(m, 2H).

Step B: Preparation of 2-((S)-2-amino-3-phenylpropylamino)-5-bromo-4-(4-pyridyl)pyridine: Bromine (757 mg, 4.7 mmole) in $CHCl_3$ (10 mL) was added in one portion to a stirring solution of 2-((S)-2-amino-3-phenylpropylamino)-4-(4-pyridyl)pyridine (1.44 g, 4.7 mmole) in $CHCl_3$ (30 mL) at room temperature. After 1 hr, the mixture was partitioned between dichloromethane and aqueous sodium bicarbonate. The organic solvent was washed with brine, dried and evaporated. The residue was purified on a column of silica gel ($CH_2Cl_2$-MeOH-Conc. $NH_4OH$=1000:110:8). MS (m/z): Calcd. $C_{19}H_{19}N_4Br$ ($M^+$): 383, found: 383, 385.1. $^1$H-NMR ($CDCl_3$, 400 MHz) δ: 8.62(d, 2H), 8.20(s, 1H), 7.30–7.10(m, 7H), 6.32(s, 1H), 5.78(bs, 1H), 3.70–3.30(m, 3H), 2.97(dd, 1H), 2.92(dd, 1H).

Step C: Preparation of 2-((S)-2-amino-3-phenylpropylamino)-5-(3-methylohenyl)-4-(4-pyridyl)pyridine: A mixture of 2-((S)-2-amino-3-phenylpropylamino)-5-bromo-4-(4-pyridyl)pyridine (4.2 g, 10.9 mmole), aqueous $Na_2CO_3$, (2M, 50 mL) and 3-methylbenzene boronic acid (1.8 g, 13 mmole) in toluene (50 mL) was stirred for 10 min. The mixture was thoroughly degassed (10 min) with nitrogen, before the addition of tetrakis(triphenyl phosphine)palladium (400 mg, 0.35 mmole). After heating at reflux for 12 hr, the reaction mixture was diluted with toluene and washed with brine. The organic solvent was dried and evaporated and the residue was subjected to chromatographic purification ($CH_2Cl_2$-MeOH-Conc. $NH_4OH$=1000:110:8). MS (m/z): Calcd. $C_{26}H_{26}N_4$ ($M^+$): 394, found $(M+H)^+$: 395.1. $^1$H-NMR ($CDCl_3$, 400 MHz) δ: 8.50(d, 2H), 8.15(s, 1H), 7.38–7.00(m, 9H), 6.90(, 1H), 6.80(d, 1H), 6.40(s, 1H), 5.38(bs, 1H), 3.62–3.20(m, 3H), 2.92(dd, 1H), 2.62(dd, 1H).

EXAMPLE 9

The following compounds were prepared according to the procedure outlined in Example 8, step C, using 2-((S)-2-amino-3-phenylpropylamino)-5-bromo-4-(4-pyridyl)pyridine and the appropriate boronic acid.

EXAMPLE 9A 2-((S)-2-amino-3-phenylpropylamino)-5-(3-isopropylphenyl)-4-(4-pyridinyl)pyridine MS (m/z): Calcd. $C_{28}H_{30}N_4$ ($M^+$): 422, found $(M+H)^+$: 423.2

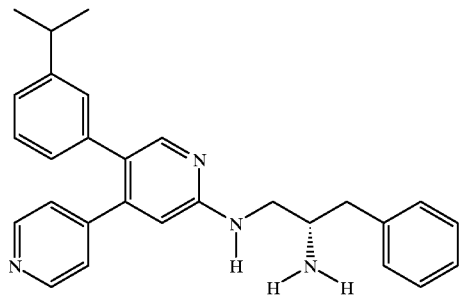

EXAMPLE 9B 2-((S)-2-amino-3-phenylpropylamino)-5-(3-trifluoromethylphenyl,-4-(4-pyridinyl)pyridine MS (m/z): Calcd. $C_{26}H_{23}N_4F_3$(M+): 448, found (M+H)+ : 449. 2

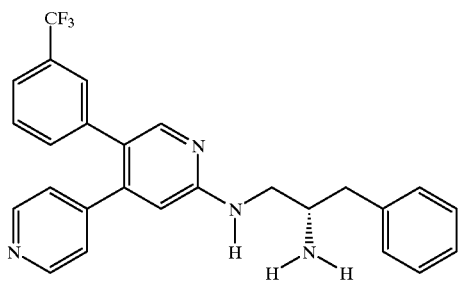

EXAMPLE 9C 2-((S)-2-amino-3-phenylpropylamino)-5-(3-fluorophenyl,-4-(4-pyridinyl)pyridine MS (m/z): Calcd. $C_{25}H_{23}N_4F$ (M+): 398, found (M+H)+: 399.1

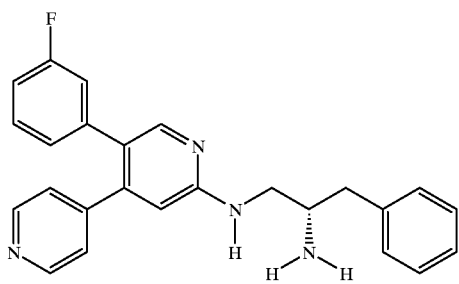

EXAMPLE 9D 2-((S)-2-amino-3-phenylpropylamino)-5-(4-chlorophenyl)-4-(4-pyridinyl)pyridine MS (m/z) Calcd. $C_{26}H_{23}N_4Cl$ (M+) 414, found (M+H)+: 415. 0.

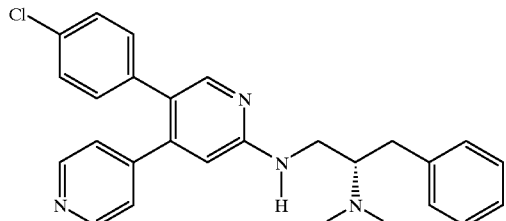

EXAMPLE 9E 2-((S)-2-amino-3-phenylpropylamino)-5-(4-fluorophenyl)-4-(4-pyridinyl)pyridine MS (m/z): Calcd. $C_{25}H_{23}N_4F$ (M+): 398, found (M+H)+: 399.1

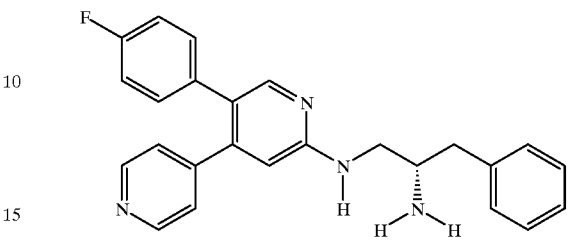

EXAMPLE 10

The following compounds were prepared according to Example 8 Step A (using 2-chloro-[4,4']-bipyridine and the corresponding amine described in Example 1), followed by Step B (bromination), and Step C (Suzuki coupling using the appropriate boronic acid):

EXAMPLE 10A

Preparation of 2-(3-amino-3-phenylpropylamino)-5-(3-methylphenyl)-4-(4-pyridinyl)pyridine MS (m/z): Calcd. $C_{26}H_{26}N_4$ (M+): 394, found (M+H)+: 395.1

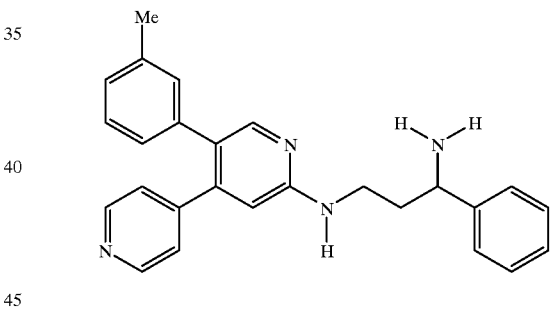

EXAMPLE 10B

Preparation of 2-(3-amino-3-phenylpropylamino)-5-(3-isopropylphenyl)-4-(4-pyridinyl)pyridine MS (m/z): Calcd. $C_{28}H_{30}N_4$ (M+): 422, found (M+H)+: 422.9

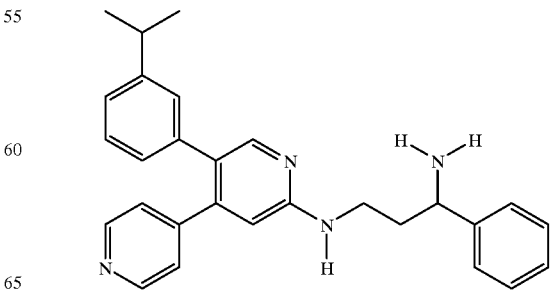

EXAMPLE 10C

Preparation of 2-(3-amino-3-phenylpropylamino)-5-(3-trifluoromethylphenyl)-4-(4-pyridinyl)pyridine MS (m/z): Calcd. $C_{26}H_{23}N_4F_3$ (M$^+$): 448, found (M+H)$^+$: 449.4

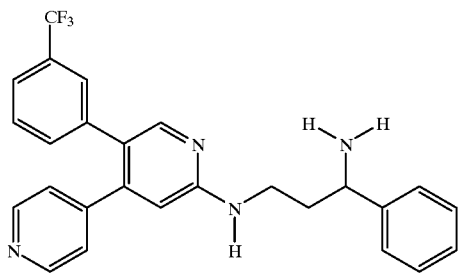

EXAMPLE 10D

Preparation of 2-(3-amino-3-phenylpropylamino)-5-(3-fluorophenyl)-4-(4-pyridinyl)pyridine MS (m/z): Calcd. $C_{25}H_{23}N_4F$ (M$^+$): 398, found (M+H)$^+$: 399.2

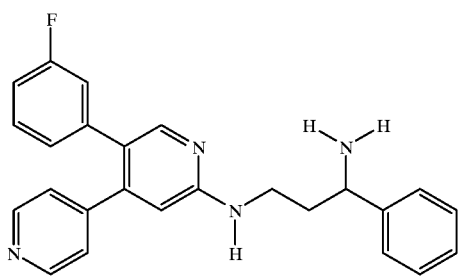

EXAMPLE 10E

Preparation of 2-(3-amino-3-phenylpropylamino)-5-(4-chlorophenyl)-4-(4-pyridinyl)pyridine MS (m/z): Calcd. $C_{26}H_{23}N_4Cl$ (M$^+$): 414, found (M+H)$^+$: 415.5.

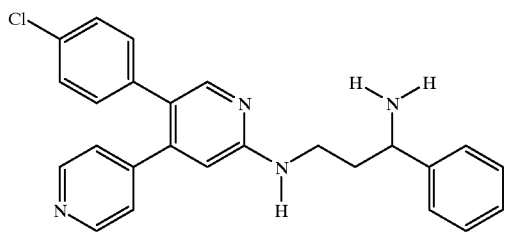

EXAMPLE 10F

Preparation of 2-(3-amino-3-phenylpropylamino)-5-(4-fluorophenyl)-4-(4-pyridinyl)pyridine MS (m/z): Calcd. $C_{25}H_{23}N_4F$ (M$^+$): 398, found (M+H)$^+$: 399.1

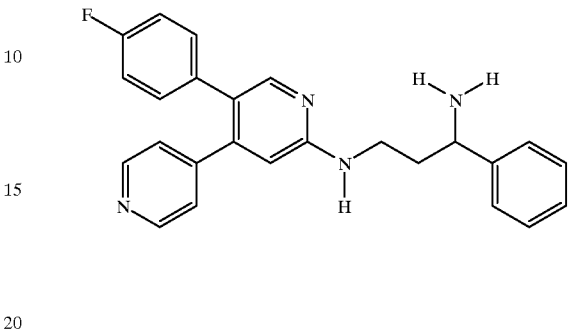

EXAMPLE 11

Procedure for Preparation of Preparation of 2-(3-phenylpropylamino)-5-(3-methylphenyl)-4-(4-pyridinyl)pyridine

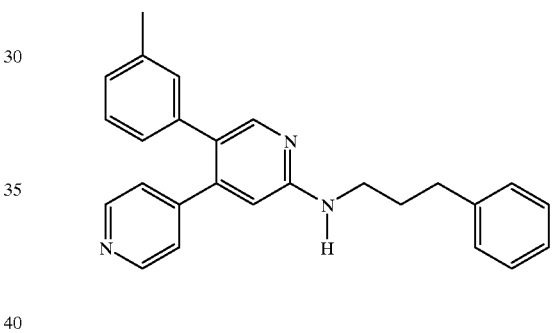

The title compound was prepared according to the procedure in Step L of Example 7 using 3-phenyl-propyl amine: MS (m/z): Calcd. $C_{26}H_{25}N_3$ (M$^+$): 379, found (M+H)$^+$: 380.3

EXAMPLE 12

Procedure for Preparation of 2-amino-[4,4']-bipyridine

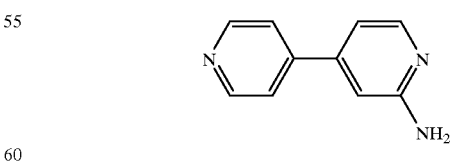

The title compound was prepared by heating 2-chloro-[4,4']bipyridinyl and NH$_4$OH (30% in H$_2$O) in a bomb at 210° C. for 48 hours: MS (m/z): Calcd. $C_{10}H_9N_3$ (M$^+$): 171, found (M+H)$^+$: 172.1

EXAMPLE 13

Procedure for Preparation of 2-(3-phenylpropylamino)-4-(3-methylphenyl)-5-(4-pyridyl)pyridine

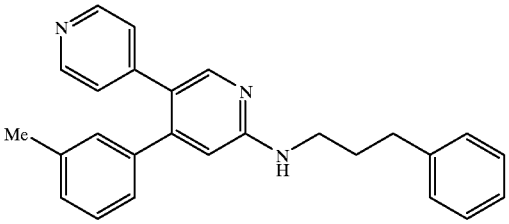

Step A: Preparation of 4-acetoxy-3-pyridine-4-yl-4-m-tolyl-cyclopent-2-en-1-one: To a solution of 4-hydroxy-4-pyridine-4-yl-3-m-tolyl-cyclopent-2-en-1-one, and it's regioisomer 4-hydroxy-3-pyridine-4-y1-4-m-toly1-cyclopent-2-en-1-one prepared as described in Example 8, Step E (265 mg, 1.0 mmole) in methylene chloride (5 mL) was added dimethylamino pyridine (183 mg, 1.5 mmole) and acetic anhydride (0.12 mL, 1.2 mmole) at r.t. The reaction mixture was stirred at that temperature for 1 hr before quenching the reaction with 1 mL of methanol. Concentration and purification (silica, hexane/ethyl acetate) gave the title compound as the slower eluting isomer. MS (m/z): Calcd. $C_{19}H_{17}NO_3(M^+)$: 307, found (M+H)$^+$: 308.1.

Step B: Preparation of 6-acetoxy-4-m-tolyl-5,6-dihydro-1H-[5,4']bipyridinyl-2-one: To a solution of 4-acetoxy-3-pyridine-4-yl-4-m-tolyl-cyclopent-2-en-1-one (160 mg, 0.52 mmole) in chloroform (3 mL) at r.t. was added NaN$_5$ (85 mg, 1.3 mmole), and MsOH (0.3 mL). The reaction mixture was stirred at that reflux for 1.5 hour before quenching the reaction with sodium bicarbonate solution. Standard basic work up, followed by purification gave the title compound. MS (m/z): Calcd. $C_{19}H_{18}N_2O_3(M^+)$: 322, found (M+H)$^+$: 323.

Step C: Preparation of 6-hydroxy-4-m-tolyl-5,6-dihydro-1H-[5,4']bipyridinyl-2-one: To a solution of 6-acetoxy-4-m-tolyl-5,6-dihydro-1H-[5,4']bipyridinyl-2-one (200 mg, 0.6 mmole) in THF (2 mL) and water (2 mL) at r.t. was added LiOH (51 mg, 1.2 mmole) in one portion. The reaction mixture was stirred at that temperature for 10 min before quenching the mixture with aqueous NH$_4$Cl. The reaction was quenched with 1.45 mL of 1N HCl the resulting white precipitate was filtered, rinsed with water and dried to give the title compound as a white solid.

Step D: Preparation of 4-(3-methylphenyl)-5-(4-pyridyl)-1H-pyrid-one To a solution of 6-hydroxy-4-m-tolyl-5,6-dihydro-1H-[5,4']bipyridinyl-2-one (83 mg, 0.29 mmole) in CHCl$_3$ (3 mL) at r.t. was added 2 ml of conc. H$_2$SO$_4$. The resulting mixture was heated to 55° C. for 2 hr. The mixture was cooled down to r.t. and was carefully quenched with aqueous sodium carbonate. Standard work up (extraction of compound with methylene chloride), followed by purification (silica gel, methanol/methylene chloride) gave the title compound.

Step E: Preparation of 2-chloro-4-(3-methylphenyl)-5-(4-pyridyl)pyridine: 4-(3-methylphenyl)-5-(4-pyridyl)-1H-pyrid-2-one (33 mg, 0.13 mmole) in POCl$_3$ (2 mL) was heated to 105° C. for 12 hr. POCl$_3$ was removed under reduced pressure. The residue was diluted with methylene chloride and was carefully quenched with aqueous sodium carbonate. Standard work up, followed by purification (silica gel, hexane/ethyl acetate) gave the title compound. MS (m/z): Calcd. $C_{17}H_{13}N_2Cl$ (M$^+$): 280.5, found (M+H)$^+$: 281 and 283.

Step F: Preparation of 2-(3-phenylpropylamino)-4-(3-methylphenyl)-5-(4-pyridyl)pyridine: A mixture of 2-chloro-4-(3-methylphenyl)-5-(4-pyridyl)pyridine (13 mg) and 3-phenylpropylamine (5 drops) was heated to 160° C. for 2 hr. The cooled reaction mixture was subjected to chromatographic purification (silica gel, methanol/methylene chloride) to give the title compound.

EXAMPLE 14

Procedure for Preparation of 2-((S)-2-amino-3-phenylpropoxy)-4-(3-methylphenyl)-5-(4-pyridyl)pyridine

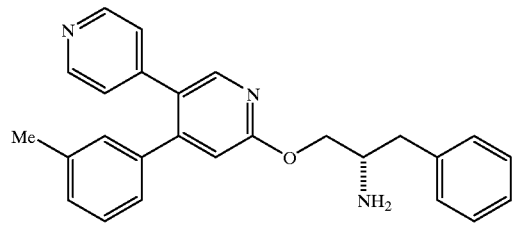

To a stirred mixture of 4-(3-methylphenyl)-5-(4-pyridyl)-1H-pyrid-2-one (12 mg, 0.05 mmole), (S)-2-tert-butoxycarbonylamino-3-phenylpropanol (15 mg, 0.06 mmole), triphenylphosphine (18 mg, 0.07 mmole), in methylene chloride (1 mL) at room temperature was added diethyl azodicarboxylate (12 mg, 0.07 mmol). When the reaction was complete (monitored by TLC), methanol was added (1 mL) and the reaction was concentrated and treated with 1 mL of 1:1 TFA/methanol for 30 minutes. The mixture was concentrated, neutralized with 1 drop conc NH$_4$OH, and purified (SiO$_2$, 10% methanol/methylene chloride) to give the title compound: MS (m/z): Calcd. $C_{26}H_{25}N_3O$ (M$^+$): 395, found (M+H)$^+$: 396.

EXAMPLE 15

Procedure for Preparation of 1-((S)-2-amino-3-phenylpropyl)-4-(3-methylphenyl)-5-(4-pyridyl)-1H-pyrid-2-one

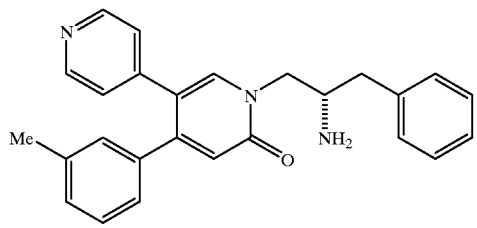

The title compound was obtained as a slower eluting by-product from Example 14: MS (m/z): Calcd. $C_{26}H_{25}N_3O$ (M$^+$): 395, found (M+H)$^+$: 396.

EXAMPLE 16

Procedure for Preparation of 2-(benzyloxy)-4-(3-methylphenyl)-5-(4-pyridyl)pyridine

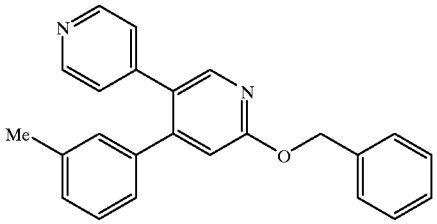

The title compound was obtained according to the procedure outlined in Example 14 using benzyl alcohol and was obtained as the faster eluting regio-isomer: MS (m/z): Calcd. $C_{24}H_{20}N_2O$ (M$^+$): 352, found (M+H)$^+$: 353.

EXAMPLE 17

Procedure for Preparation of 1-benzyl-4-(3-methylphenyl)-5-(4-pyridyl)-1H-pyrid-2-one

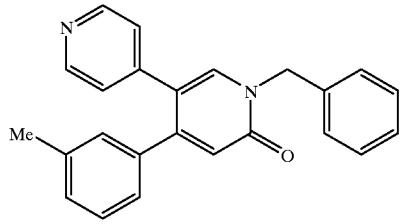

The title compound was obtained from the reaction outlined in Example 16 and was obtained as the faster eluting regio-isomer: MS (m/z): Calcd. $C_{24}H_{20}N_2O$ (M$^+$): 352, found (M+H)$^+$: 353.

EXAMPLE 18

Procedure for Preparation of 2-(3-phenylpropoxy)-4-(3-methylphenyl)-5-(4-pyridyl)pyridine

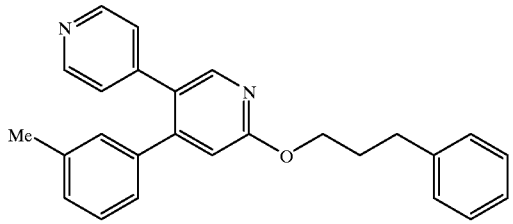

The title compound was obtained according to the procedure outlined in Example 14 using 3-phenylpropanol and was obtained as the faster eluting regio-isomer: MS (m/z): Calcd. $C_{26}H_{24}N_2O$ (M$^+$): 380, found (M+H)$^+$: 381.

EXAMPLE 19

Procedure for Preparation of 1-(3-phenylpropyl)-4-(3-methylphenyl)-5-(4-pyridyl)-1H-pyrid-2-one

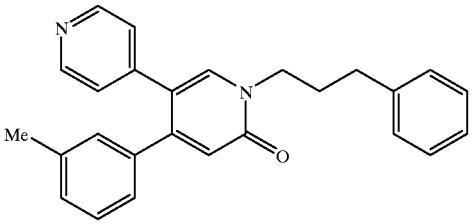

The title compound was obtained from the reaction outlined in Example 18, and was obtained as the slower eluting regio-isomer: MS (m/z): Calcd. $C_{26}H_{24}N_2O$ (M$^+$): 380, found (M+H)$^+$: 381.

EXAMPLE 20

Procedure for Preparation of 2-(4-pyridylmethoxy)-4-(4-fluorophenyl)-5-(4-pyridyl)pyridine

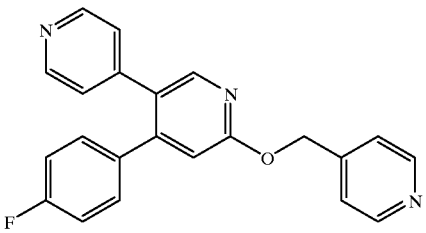

The title compound was obtained from the reaction outlined in Example 14 using 4-(4-fluorophenyl)-5-(4-pyridyl)-1H-pyrid-2-one and 4-pyridylcarbinol, and was obtained as the faster eluting isomer: MS (m/z): Calcd. $C_{23}H_{17}N_3FO$ (M$^+$): 356, found (M+H)$^+$: 357.

EXAMPLE 21

Procedure for Preparation of 1-(4-pyridylmethoxy)-4-(4-fluorophenyl)-5-(4-pyridyl)-1H-pyrid-2-one

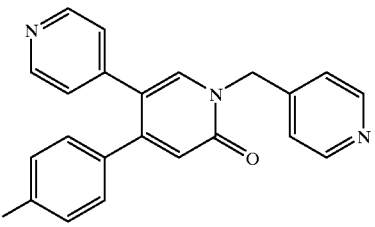

The title compound was obtained from the reaction outlined in Example 20, and was obtained as the slower eluting regio-isomer: MS (m/z): Calcd. $C_{23}H_{17}N_2FO$ (M$^+$): 356, found (M+H)$^+$: 357.

EXAMPLE 22

Biological Assays

The following assays were used to characterize the ability of compounds of the invention to inhibit the production of TNF-α and IL-1-β. The second assay measured the inhibition of TNF-α and/or IL-1-β in mice after oral administration of the test compounds. The third assay, a glucagon binding inhibition in vitro assay, can be used to characterize the ability of compounds of the invention to inhibit glucagon binding. The fourth assay, a Cyclooxygenase enzyme (COX-1 and COX-2) inhibition activity in vitro assay, can be used to characterize the ability of compounds of the invention to inhibit COX-1 and/or COX-2. The fifth assay, a Raf-kinase inhibition assay, can be used to characterize the compounds of the invention to inhibit phosphorylation of MEK by activated Raf-kinase.

Lipopolysaccharide-Activated Monocyte TNF Production Assay

Isolation of Monocytes

Test compounds were evaluated in vitro for the ability to inhibit the production of TNF by monocytes activated with bacterial lipopolysaccharide (LPS). Fresh residual source leukocytes (a byproduct of plateletpheresis) were obtained from a local blood bank, and peripheral blood mononuclear cells (PBMCs) were isolated by density gradient centrifugation on Ficol-Paque Plus (Pharmacia). PBMCs were suspended at $2 \times 10^6$/ml in DMEM supplemented to contain 2% FCS, 10 mM, 0.3 mg/ml glutamate, 100 U/ml penicillin G and 100 mg/ml streptomycin sulfate (complete media). Cells were plated into Falcon flat bottom, 96 well culture plates (200 μl/well) and cultured overnight at 37° C. and 6% $CO_2$. Non-adherent cells were removed by washing with 200 μl/well of fresh medium. Wells containing adherent cells (~70% monocytes) were replenished with 100 μl of fresh medium.

Preparation of Test Compound Stock Solutions

Test compounds were dissolved in DMZ. Compound stock solutions were prepared to an initial concentration of 10–50 μM. Stocks were diluted initially to 20–200 μM in complete media. Nine two-fold serial dilutions of each compound were then prepared in complete medium.

Treatment of Cells With Test Compounds and Activation of TNF Production With Lipopolysaccharide One hundred microliters of each test compound dilution were added to microtiter wells containing adherent monocytes and 100 μl complete medium. Monocytes were cultured with test compounds for 60 min at which time 25 μl of complete medium containing 30 ng/ml lipopolysaccharide from E. coli K532 were added to each well. Cells were cultured an additional 4 hrs. Culture supernatants were then removed and TNF presence in the supernatants was quantified using an ELISA.

TNF ELISA

Flat bottom, 96 well Corning High Binding ELISA plates were coated overnight (4° C.) with 150 μL/well of 3 μg/ml murine anti-human TNF-α MAb (R&D Systems #MAB210). Wells were then blocked for 1 hr at room temperature with 200 μL/well of $CaCl_3$-free ELISA buffer supplemented to contain 20 mg/ml BSA (standard ELISA buffer: 20 mM, 150 mM NaCl, 2 mM $CaCl_2$, 0.15 mM thimerosal, pH 7.4). Plates were washed and replenished with 100 μl of test supernatants (diluted 1:3) or standards. Standards consisted of eleven 1.5-fold serial dilutions from a stock of 1 ng/ml recombinant human TNF (R&D Systems). Plates were incubated at room temperature for 1 hr on orbital shaker (300 rpm), washed and replenished with 100 μl/well of 0.5 μg/ml goat anti-human TNF-α (R&D systems #AB-210-NA) biotinylated at a 4:1 ratio. Plates were incubated for 40 min, washed and replenished with 100 μl/well of alkaline phosphatase-conjugated streptavidin (Jackson ImmunoResearch #016-050-084) at 0.02 μg/ml. Plates were incubated 30 min, washed and replenished with 200 μl/well of 1 mg/ml of p-nitrophenyl phosphate. After 30 min, plates were read at 405 nm on a $V_{max}$ plate reader.

Data Analysis

Standard curve data were fit to a second order polynomial and unknown TNF-α concentrations determined from their OD by solving this equation for concentration. TNF concentrations were then plotted vs. test compound concentration using a second order polynomial. This equation was then used to calculate the concentration of test compounds causing a 50% reduction in TNF production.

Compounds of the invention can also be shown to inhibit LPS-induced release of IL-1β, IL-6 and/or IL-8 from monocytes by measuring concentrations of IL-1β, IL-6 and/or IL-8 by methods well known to those skilled in the art. In a similar manner to the above described assay involving the LPS induced release of TNF-α from monocytes, compounds of this invention can also be shown to inhibit LPS induced release of IL-1β, IL-6 and/or IL-8 from monocytes by measuring concentrations of IL-1β, IL-6 and/or IL-8 by methods well known to those skilled in the art. Thus, the compounds of the invention may lower elevated levels of TNF-α, IL-1, IL-6, and IL-8 levels. Reducing elevated levels of these inflammatory cytokines to basal levels or below is favorable in controlling, slowing progression, and alleviating many disease states. All of the compounds are useful in the methods of treating disease states in which TNF-α, IL-1β, IL-6, and IL-8 play a role to the full extent of the definition of TNF-α-mediated diseases described herein.

Inhibition of LPS-Induced TNF-α Production in Mice

Male DBA/1LACJ mice were dosed with vehicle or test compounds in a vehicle (the vehicle consisting of 0.5% tragacanth in 0.03 N HCl) 30 minutes prior to lipopolysaccharide (2 mg/kg, I.V.) injection. Ninety minutes after LPS injection, blood was collected and the serum was analyzed by ELISA for TNF levels.

The following compounds exhibit activities in the monocyte assay (LPS induced TNF release) with $IC_{50}$ values of 20 μM or less:

1-(3-phenylpropyl)-4-(3-methylphenyl)-5-(4-pyridyl)-1H-pyrid-2-one
2-(3-phenylpropoxy)-4-(3-methylphenyl)-5-(4-pyridyl)pyridine
1-((S)-2-amino-3-phenylpropyl)-4-(3-methylphenyl)-5-(4-pyridyl)-1H-pyrid-2-one
2-((S)-2-amino-3-phenylpropoxy)-4-(3-methylphenyl)-5-(4-pyridyl)pyridine
2-(3-amino-3-phenylpropylamino)-5-(4-fluorophenyl)-4-(4-pyridinyl)pyridine
2-(3-amino-3-phenylpropylamino)-5-(4-chlorolphenyl)-4-(4-pyridinyl)pyridine
2-(3-amino-3-phenylpropylamino)-5-(3-fluorophenyl)-4-(4-pyridinyl)pyridine
2-(3-amino-3-phenylpropylamino)-5-(3-trifluoromethylphenyl)-4-(4-pyridinyl)pyridine
2-(3-amino-3-phenylpropylamino)-5-(3-isopropylphenyl)-4-(4-pyridinyl)pyridine
2-(3-amino-3-phenylpropylamino)-5-(3-methylphenyl)-4-(4-pyridinyl)pyridine
2-((S)-2-amino-3-phenylpropylamino)-5-(4-fluorophenyl)-4-(4-pyridinyl)pyridine
2-((S)-2-amino-3-phenylpropylamino)-5-(4-chlorophenyl)-4-(4-pyridinyl)pyridine
2-((S)-2-amino-3-phenylpropylamino)-5-(3-fluorophenyl-4-(4-pyridinyl)pyridine
2-((S)-2-amino-3-phenylpropylamino)-5-(3-trifluoromethylphenyl-4-(4-pyridinyl)pyridine 2-((S)-2-amino-3-phenylpropylamino)-5-(3-isopropylphenyl)-4-(4-pyridinyl)pyridine
6-[((S)-2-amino-3-phenylpropyl)-amino]-3-(4-fluorophenyl)-4-(4-pyridyl)-pyridazine
6-((S)-2-Amino-3-phenylpropylamino)-3-(2-benzothiophenyl)-2-(4-pyridyl)pyridine
6-((S)-2-Amino-3-phenylpropylamino)-3-(4-chloro-3-fluorophenyl)-2-(4-pyridyl)pyridine
6-((S)-2-Amino-3-phenylpropylamino)-3-(4-methoxyphenyl)-2-(4-pyridyl)pyridine
6-((S)-2-Amino-3-phenylpropylamino)-3-(3-isopropylphenyl)-2-(4-pyridyl)pyridine
6-((S)-2-Amino-3-phenylpropylamino)-3-(4-chlorophenyl)-2-(4-pyridyl)pyridine
6-((S)-2-Amino-3-phenylpropylamino)-3-(2-napthyl)-2-(4-pyridyl)pyridine
6-((S)-2-Amino-3-phenylpropylamino)-3-(3-trifluoromethylphenyl)-2-(4-pyridyl)pyridine
6-((S)-2-Amino-3-phenylpropylamino)-3-(3-methylphenyl)-2-(4-pyridyl)pyridine The following compounds exhibit activities in the monocyte assay (LPS induced TNF release) with $IC_{50}$ values of 5 μM or less:

1-((S)-2-amino-3-phenylpropyl)-4-(3-methylphenyl)-5-(4-pyridyl)-1H-pyrid-2-one
2-(3-amino-3-phenylpropylamino)-5-(4-fluorophenyl)-4-(4-pyridinyl)pyridine
2-(3-amino-3-phenylpropylamino)-5-(4-chlorolphenyl)-4-(4-pyridinyl)pyridine
2-(3-amino-3-phenylpropylamino)-5-(3-fluorophenyl)-4-(4-pyridinyl)pyridine
2-(3-amino-3-phenylpropylamino)-5-(3-trifluoromethylphenyl)-4-(4-pyridinyl)pyridine
2-(3-amino-3-phenylpropylamino)-5-(3-isopropylphenyl)-4-(4-pyridinyl)pyridine
2-(3-amino-3-phenylpropylamino)-5-(3-methylphenyl)-4-(4-pyridinyl)pyridine
2-((S)-2-amino-3-phenylpropylamino)-5-(4-fluorophenyl)-4-(4-pyridinyl)pyridine
2-((S)-2-amino-3-phenylpropylamino)-5-(4-chlorophenyl)-4-(4-pyridinyl)pyridine
2-((S)-2-amino-3-phenylpropylamino)-5-(3-fluorophenyl-4-(4-pyridinyl)pyridine
2-((S)-2-amino-3-phenylpropylamino)-5-(3-trifluoromethylphenyl-4-(4-pyridinyl)pyridine
2-((S)-2-amino-3-phenylpropylamino)-5-(3-isopropylphenyl)-4-(4-pyridinyl)pyridine
6-[((S)-2-amino-3-phenylpropyl)-amino]-3-(4-fluorophenyl)-4-(4-pyridyl)-pyridazine
6-((S)-2-Amino-3-phenylpropylamino)-3-(2-benzothiophenyl)-2-(4-pyridyl)pyridine
6-((S)-2-Amino-3-phenylpropylamino)-3-(4-chloro-3-fluorophenyl)-2-(4-pyridyl)pyridine
6-((S)-2-Amino-3-phenylpropylamino)-3-(4-methoxyphenyl)-2-(4-pyridyl)pyridine
6-((S)-2-Amino-3-phenylpropylamino)-3-(3-isopropylphenyl)-2-(4-pyridyl)pyridine
6-((S)-2-Amino-3-phenylpropylamino)-3-(4-chlorophenyl)-2-(4-pyridyl)pyridine
6-((S)-2-Amino-3-phenylpropylamino)-3-(2-napthyl)-2-(4-pyridyl)pyridine
6-((S)-2-Amino-3-phenylpropylamino)-3-(3-trifluoromethylphenyl)-2-(4-pyridyl)pyridine
6-((S)-2-Amino-3-phenylpropylamino)-3-(3-methylphenyl)-2-(4-pyridyl)pyridine.

Compounds of the invention may be shown to have anti-inflammatory properties in animal models of inflammation, including carageenan paw edema, collagen induced arthritis and adjuvant arthritis, such as the carageenan paw edema model (C. A. Winter et al Proc. Soc. Exp. Biol. Med. (1962) vol 111, p 544; K. F. Swingle, in R. A. Scherrer and M. W. Whitehouse, Eds., Antiinflammatory Agents, Chemistry and Pharmacology, Vol. 13-II, Academic, New York, 1974, p. 33) and collagen induced arthritis (D. E. Trentham et al J. Exp. Med. (1977) vol. 146, p 857; J. S. Courtenay, Nature (New Biol.) (1980), Vol 283, p 666).

$^{125}$I-Glucagon Binding Screen with CHO/hGLUR Cells

The assay is described in WO 97/16442, which is incorporated herein by reference in its entirety.

Reagents

The reagents can be prepared as follows: (a) prepare fresh 1M o-Phenanthroline (Aldrich) (198.2 mg/ml ethanol); (b) prepare fresh 0.5M DTT (Sigma); (c) Protease Inhibitor Mix (1000×): 5 mg leupeptin, 10 mg benzamidine, 40 mg bacitracin and 5 mg soybean trypsin inhibitor per ml DMSO and store aliquots at −20μ C.; (d) 250 μM human glucagon (Peninsula): solubilize 0.5 mg vial in 575 μl 0.1N acetic acid (1 μl yields 1 μM final concentration in assay for non-specific binding) and store in aliquots at −20° C.; (e) Assay Buffer: 20 mM Tris (pH 7.8), 1 mM DTT and 3 mM o-phenanthroline; (f) Assay Buffer with 0.1% BSA (for dilution of label only; 0.01% final in assay): 10 μl 10% BSA (heat-inactivated) and 990 μl Assay Buffer; (g) $^{125}$I-Glucagon (NEN, receptor-grade, 2200 Ci/mmol): dilute to 50,000 cpm/25 μl in assay buffer with BSA (about 50 pM final concentration in assay).

Harvesting of CHO/hGLUR Cells for Assay

1. Remove media from confluent flask then rinse once each with PBS (Ca, Mg-free) and Enzyme-free Dissociation Fluid (Specialty Media, Inc.).
2. Add 10 ml Enzyme-free Dissoc. Fluid and hold for about 4 min. at 37° C.
3. Gently tap cells free, triturate, take aliquot for counting and centrifuge remainder for 5 min. at 1000 rpm.
4. Resuspend pellet in Assay Buffer at 75000 cells per 100 μl.

Membrane preparations of CHO/hGLUR cells can be used in place of whole cells at the same assay volume. Final protein concentration of a membrane preparation is determined on a per batch basis.

Assay

The determination of inhibition of glucagon binding can be carried out by measuring the reduction of $I^{125}$-glucagon binding in the presence of compounds of Formula I. The reagents are combined as follows:

| | Compound/Vehicle | 250 μM Glucagon | $^{125}$I-Glucagon | CHO/hGLUR Cells |
|---|---|---|---|---|
| Total Binding | —/5 μl | — | 25 μl | 100 μl |
| + Compound | 5 μl/— | — | 25 μl | 100 μl |
| Nonspecific Binding | —/5 μl | 1 μl | 25 μl | 100 μl |

The mixture is incubated for 60 min. at 22° C. on a shaker at 275 rpm. The mixture is filtered over pre-soaked (0.5% polyethylimine (PEI)) GF/C filtermat using an Innotech Harvester or Tomtec Harvester with four washes of ice-cold 20 mM Tris buffer (pH 7.8). The radioactivity in the filters is determined by a gamma-scintillation counter.

Thus, compounds of the invention may also be shown to inhibit the binding of glucagon to glucagon receptors.

Cyclooxygenase Enzyme Activity Assay

The human monocytic leukemia cell line, THP-1, differentiated by exposure to phorbol esters expresses only COX-1; the human osteosarcoma cell line 143B expresses predominantly COX-2. THP-1 cells are routinely cultured in RPMI complete media supplemented with 10% FBS and human osteosarcoma cells (HOSC) are cultured in minimal essential media supplemented with 10% fetal bovine serum (MEM-10%FBS); all cell incubations are at 37° C. in a humidified environment containing 5% $CO_2$.

COX-1 Assay

In preparation for the COX-1 assay, THP-1 cells are grown to confluency, split 1:3 into RPMI containing 2% FBS and 10 mM phorbol 12-myristate 13-acetate (TPA), and incubated for 48 hours on a shaker to prevent attachment. Cells are pelleted and resuspended in Hank's Buffered Saline (HBS) at a concentration of $2.5 \times 10^6$ cells/mL and plated in 96-well culture plates at a density of $5 \times 10^5$ cells/mL. Test compounds are diluted in HBS and added to the desired final concentration and the cells are incubated for an additional 4 hours. Arachidonic acid is added to a final concentration of 30 mM, the cells incubated for 20 minutes at 37° C., and enzyme activity determined as described below.

COX-2 Assay

For the COX-2 assay, subconfluent HOSC are trypsinized and resuspended at $3 \times 10^6$ cells/mL in MEM-FBS containing 1 ng human IL-1b/mL, plated in 96-well tissue culture plates at a density of $3 \times 10^4$ cells per well, incubated on a shaker for 1 hour to evenly distribute cells, followed by an additional 2 hour static incubation to allow attachment. The media is then replaced with MEM containing 2% FBS (MEM-2%FBS) and 1 ng human IL-1b/mL, and the cells incubated for 18–22 hours. Following replacement of media with 190 mL MEM, 10 mL of test compound diluted in HBS is added to achieve the desired concentration and the cells incubated for 4 hours. The supernatants are removed and replaced with MEM containing 30 mM arachidonic acid, the cells incubated for 20 minutes at 37° C., and enzyme activity determined as described below.

COX Activity Determined

After incubation with arachidonic acid, the reactions are stopped by the addition of 1 N HCl, followed by neutralization with 1 N NaOH and centrifugation to pellet cell debris. Cyclooxygenase enzyme activity in both HOSC and THP-1 cell supernatants is determined by measuring the concentration of $PGE_2$ using a commercially available ELISA (Neogen #404110). A standard curve of $PGE_2$ is used for calibration, and commercially available COX-1 and COX-2 inhibitors are included as standard controls.

Raf Kinase Assay

In vitro Raf kinase activity is measured by the extent of phosphorylation of the substrate MEK (Map kinase/ERK kinase) by activated Raf kinase, as described in GB 1,238,959 (incorporated herein by reference in its entirety). Phosphorylated MEK is trapped on a filter and incorporation of radiolabeled phosphate is quantified by scintillation counting.

Materials

Activated Raf is produced by triple transfection of Sf9 cells with baculoviruses expressing "Glu-Glu"-epitope tagged Raf,val$^{12}$-H-Ras, and Lck. The "Glu-Glu"-epitope, Glu-Try-Met-Pro-Met-Glu, was fused to the carboxy-terminus of full length c-Raf.

Catalytically inactive MEK (K97A mutation) is produced in Sf9 cells transfected with a baculovirus expressing c-terminus "Glu-Glu" epitope-tagged K97A MEK1.

Anti "Glu-Glu" antibody was purified from cells grown as described in: Grussenmeyer, et al., Proceedings of the National Academy of Science, U.S.A. pp 7952–7954, 1985.

Column buffer: 20 mM Tris pH=8, 100 mM NaCl, 1 mM EDTA, 2.5 mM EGTA, 10 mM $MgCl_2$, 2 mM DTT, 0.4 mM AEBSF, 0.1% n-octylglucopyranoside, 1 nM okadeic acid, and 10 μg/mL each of benzamidine, leupeptin, pepstatin, and aprotinin.

5× Reaction buffer: 125 mM HEPES pH=8, 25 mM $MgCl_2$, 5 mM EDTA, 5 mM $Na_3VO_4$, 100 μg/mL BSA.

Enzyme dilution buffer: 25 mM HEPES pH=8, 1 mM EDTA, 1 mM $Na_3VO_4$, 400 μg/mL BSA.

Stop solution: 100 mM EDTA, 80 mM sodium pyrophosphate.

Filter plates: Milipore multiscreen #SE3MO78E3, Immobilon-P (PVDF).

Methods

Protein purification: Sf9 cells were infected with baculovirus and grown as described in Williams, et al., Proceedings of the National Academy of Science, U.S.A. pp 2922–2926, 1992. All subsequent steps were preformed on ice or at 4° C. Cells were pelleted and lysed by sonication in column buffer. Lysates were spun at 17,000× g for 20 min, followed by 0.22 μm filtration. Epitope tagged proteins were purified by chromatography over GammaBind Plus affinity column to which the "Glu-Glu" antibody was coupled. Proteins were loaded on the column followed by sequential washes with two column volumes of column buffer, and eluted with 50 μg/mL Glu-Tyr-Met-Pro-Met-Glu in column buffer.

Raf kinase assay: Test compounds were evaluated using ten 3-fold serial dilutions starting at 10–100 μM. 10 μL of the test inhibitor or control, dissolved in 10% DMSO, was added to the assay plate followed by the addition of 30 μL of the a mixture containing 10 μL 5× reaction buffer, 1 mM $^{33}$P-γ-ATP (20 μCi/mL), 0.5 μL MEK (2.5 mg/mL), 1 μL 50 mM β-mercaptoethanol. The reaction was started by the addition of 10 μL of enzyme dilution buffer containing 1 mM DTT and an amount of activated Raf that produces linear kinetics over the reaction time course. The reaction was mixed and incubated at room temperature for 90 min. and stopped by the addition of 50 μL stop solution. 90 μL aliquots of this stopped solution were transferred onto GFP-30 cellulose microtiter filter plates (Polyfiltronics), the filter plates washed in four well volumes of 5% phosphoric acid, allowed to dry, and then replenished with 25 μl scintillation cocktail. The plates were counted for $^{33}$P gamma emission using a TopCount Scintillation Reader.

Accordingly, the compounds of the invention or a pharmaceutical composition thereof are useful for prophylaxis and treatment of rheumatoid arthritis; Pagets disease; osteophorosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; Reiter's syndrome; type I and type II diabetes; bone resorption diseases; graft vs. host reaction; ischemia reperfusion injury; atherosclerosis; brain trauma; Alzheimer's disease; stroke; myocardial infarction; multiple sclerosis; cerebral malaria; sepsis; septic shock; toxic shock syndrome; fever, and myalgias due to infection. HIV-1, HIV-2, HIV-3, cytomegalovirus (CMV), influenza, adenovirus, the herpes viruses (including HSV-1, HSV-2), and herpes zoster, all of which are sensitive to TNF-α and/or IL-1 inhibition or glucagon antagonism, will also be positively effected by the compounds and methods of the invention.

The compounds of the present invention may also possess oncolytic characteristics and may be useful for the treatment of cancer. The compounds of the present invention may also block signal transduction by extracellular mitogenic stimuli and oncoproteins through inhibition of Raf kinase. Thus the compounds of the present invention, a pharmaceutical salt thereof, or a pharmaceutical composition of either, may also be useful in the prophylaxis and/or treatment of cancers which are mediated by Raf and Raf-inducable proteins, such as cancers where Raf kinase is implicated by overexpression and cancers involving overexpression of upstream activators of Raf or Raf-activating oncogenes. Examples of cancers where Raf kinase is implicated by overexpression include cancers of the brain, larynx, lung, lymphatic system, urinary tract and stomach, including hystocytic lymphoma, lung adenocarcinoma, small cell lung cancers and the like. Examples of cancers involving overexpression of upstream activators of Raf or Raf-activating oncogenes, include pancreatic carcinoma, breast carcinoma and the like.

The compounds of the present invention also may possess analgesic properties and may be useful for the treatment of pain disorders, such as hyperalgesia due to excessive IL-1. The compounds of the present invention may also prevent the production of prostaglandins by inhibition of enzymes in the human arachidonic acid/prostaglandin pathway, including cyclooxygenase (WO 96/03387, incorporated herein by reference in its entirety).

Because of their ability to lower TNF-α and IL-1 concentrations or inhibit glucagon binding to its receptor, the compounds of the invention are also useful research tools for studying the physiology associated with blocking these effects.

The methods of the invention comprise administering an effective dose of a compound of the invention, a pharmaceutical salt thereof, or a pharmaceutical composition of either, to a subject (i.e., an animal, preferably a mammal, most preferably a human) in need of a reduction in the level of TNF-α, IL-1, IL-6, and/or IL-8 levels and/or reduction in plasma glucose levels and/or which subject may be suffering from rheumatoid arthritis; Pagets disease; osteophorosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; Reiter's syndrome; type I and type II diabetes; cancer; bone resorption diseases; graft vs. host reaction; Alzheimer's disease; stroke; myocardial infarction; ischemia reperfusion injury; atherosclerosis; brain trauma; multiple sclerosis; cerebral malaria; sepsis; septic shock; toxic shock syndrome; fever, and myalgias due to infection, or which subject is infected by HIV-1, HIV-2, HIV-3, cytomegalovirus (CMV), influenza, adenovirus, the herpes viruses (including HSV-1, HSV-2), or herpes zoster.

In another aspect, this invention comprises the use of a compound of the invention, or pharmaceutically acceptable salts thereof, in the manufacture of a medicament for the treatment either acutely or chronically of a TNF-α, IL-1-β, IL-6, and/or IL-8 mediated disease state, including those described previously. The compounds of the present are also useful in the manufacture of an anti-cancer medicant. The compounds of the present invention are also useful in the manufacture of a medicant to attenuate or prevent signal transduction by extracellular mitogenic stimuli and oncoproteins through inhibition of Raf kinase. Also, the compounds of this invention are useful in the manufacture of a analgesic medicament and a medicament for treating pain disorders, such as hyperalgesia. The compounds of the present invention also are useful in the manufacture of a medicament to prevent the production of prostaglandins by inhibition of enzymes in the human arachidonic acid/prostaglandin pathway.

A further method of the invention comprises administering an effective dose of a compound of the invention, a pharmaceutical salt thereof, or a pharmaceutical composition of either, to a subject (i.e., an animal, preferably a mammal, most preferably a human) in need of prophylaxis and/or treatment of a cancer(s) which is mediated by Raf, Raf-inducable proteins and/or activators of Raf or Raf-activating oncogenes, and/or which subject may be suffering from cancers of the brain, larynx, lung, lymphatic system, urinary tract and stomach, including hystocytic lymphoma, lung adenocarcinoma, small cell lung cancers, pancreatic carcinoma, breast carcinoma and the like. Further, the compounds of this invention may be useful in the manufacture of a medicament for treating cancers, such as cancers of the brain, larynx, lung, lymphatic system, urinary tract and stomach, including hystocytic lymphoma, lung adenocarcinoma, small cell lung cancers, pancreatic carcinoma, breast carcinoma and the like.

In still another aspect, this invention provides a pharmaceutical composition comprising an effective TNF-α, IL-1β, IL-6, and/or IL-8 lowering amount and/or effective plasma glucose level lowering amount and/or effective tumor supressing amount of a compound of the invention and a pharmaceutically acceptable carrier or diluent, and if desired other active ingredients. The compounds of the invention are administered by any suitable route, preferably in the form of a pharmaceutical composition adapted to such a route, and in a dose effective for the treatment intended. Therapeutically effective doses of the compounds of the present invention required to arrest the progress or prevent tissue damage associated with the disease are readily ascertained by one of ordinary skill in the art using standard methods.

For the treatment of TNF-α, IL-1β, IL-6, and IL-8 mediated diseases, cancer, and/or hyperglycemia, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

The dosage regimen for treating a TNF-α, IL-1, IL-6, and IL-8 mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non- irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hyroxy-ethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A compound of formula

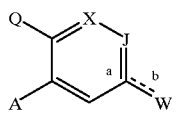

(I)

or a pharmaceutically acceptable salt thereof, wherein
W is $R_1$, $R_2$, or N—$R_3$;
A is $R_{11}$ and Q is $R_{12}$, or A is $R_{12}$ and Q is $R_{11}$;
X is N and J is C—$R_1$ or C—$R_2$, or X is C—H and J is N—$R_3$ or N; and
when W is $R_1$, then $\underline{a}$ is a double bond, $\underline{b}$ is a single bond and J is other than N—$R_3$ or C—$R_1$; when W is $R_2$, then $\underline{a}$ is a double bond, $\underline{b}$ is a single bond and J is other than N—$R_3$ or C—$R_2$; and when W is O or N—$R_3$, then $\underline{a}$ is a single bond, $\underline{b}$ is a double bond and J is N—$R_3$;
$R_1$ is —Z—Y or —Y; and each $R_3$ is independently a hydrogen radical or —Z—Y; provided that the total number of aryl, heteroaryl, cycloalkyl and heterocyclyl radicals in $R_1$, $R_2$ and $R_3$ is 0–3;
$R_2$ is (1) a hydrogen, halo, trifluoromethyl, cyano, —C(O)—$OR_{21}$ or —C(O)—$NR_5R_{23}$ radical;
(2) alkyl radical optionally substituted by (a) 1–2 radicals of amino, alkylamino, dialkylamino, alkanoylamino, alkoxycarbonylamino, alkylsulfonylamino, hydroxy, alkoxy or alkylthio, and (b) a radical of heterocyclyl, aryl or heteroaryl optionally substituted by 1–3 radicals of amino, alkylamino, dialkylamino, alkanoylamino, alkoxycarbonylamino, alkylsulfonylamino, hydroxy, alkoxy, alkylthio, halo, alkyl, carboxy, carboxamide, trifluoromethoxy or trifluoromethyl radicals; or
(3) aryl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl, carboxy, carboxamide, trifluoromethoxy or trifluoromethyl radicals;
Z is independently a
(1) alkyl, alkenyl or alkynyl radical optionally substituted by (a) 1–3 radicals of amino, alkylamino, dialkylamino, alkanoylamino, alkoxycarbonylamino, alkylsulfonylamino, hydroxy, alkoxy, alkylthio or halo, and (b) 1–2 radicals of heterocyclyl, aryl or heteroaryl; or
(2) heterocyclyl, aryl or heteroaryl radical;
wherein the heterocyclyl radicals are optionally substituted by 1–3 radicals of amino, alkylamino, dialkylamino, alkanoylamino, alkoxycarbonylamino, alkylsulfonylamino, hydroxy, alkoxy, alkylthio, alkyl, arylalkyl, heteroarylalkyl or haloalkyl; and the aryl and heteroaryl radicals are optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl or haloalkyl;
each Y is independently a
(1) hydrogen radical;
(2) halo or nitro radical;
(3) —C(O)—$R_{20}$, —C(O)—$OR_{21}$, —C(O)—$NR_5R_{21}$ or —C($NR_5$)—$NR_5R_{21}$ radical;
(4) —$OR_{21}$, —O—C(O)—$R_{21}$, —O—C(O)—$NR_5R_{21}$ or —O—C(O)—$NR_{22}$—S(O)$_2$—$R_{20}$ radical;
(5) —$SR_{21}$, —S(O)—$R_{20}$, —S(O)$_2$—$R_{20}$, —S(O)$_2$—$NR_5R_{21}$, —S(O)$_2$—$NR_{22}$—C(O)—$R_{21}$, —S(O)$_2$—$NR_{22}$—C(O)—$OR_{20}$ or —S(O)$_2$—$NR_{22}$—C(O)—$NR_5R_{21}$ radical; or
(6) —$NR_5R_{21}$, —$NR_{22}$—C(O)—$R_{21}$, —$NR_{22}$—C(O)—$OR_{20}$, —$NR_{22}$—C(O)—$NR_5R_{21}$, —$NR_{22}$—C($NR_5$)—$NR_5R_{21}$, —$NR_{22}$—S(O)$_2$—$R_{20}$ or —$NR_{22}$—S(O)$_2$—$NR_5R_{21}$ radical;
each $R_5$ is independently
(1) hydrogen radicals;
(2) alkyl, alkenyl or alkynyl radicals optionally substituted by 1–3 radicals of amino, alkylamino, dialkylamino, hydroxy, alkoxy, alkylthio, —$SO_3H$ or halo; or
(3) aryl, heteroaryl, aralkyl, heteroaralkyl, heterocyclyl, heterocyclylalkyl, cycloalkyl or cycloalkylalkyl radicals optionally substituted by 1–3 radicals of amino, alkylamino, dialkylamino, hydroxy, alkoxy, alkylthio, alkyl or haloalkyl;
each $R_{20}$ is independently
(1) alkyl, alkenyl or alkynyl radicals optionally substituted by 1–3 radicals of amino, alkylamino, dialkylamino, alkanoylamino, alkoxycarbonylamino, N-(alkoxycarbonyl)-N-(alkyl)amino, aminocarbonylamino, alkylsulfonylamino, hydroxy, alkoxy, alkylthio, alkylsulfinyl, alkylsulfonyl, halo or aralkoxy, aralkylthio, aralkylsulfonyl, cycloalkyl, heterocyclyl, aryl or heteroaryl radicals optionally substituted by 1–3 radicals of amino, alkylamino, dialkylamino, alkanoylamino, alkoxycarbonylamino, alkylsulfonylamino, alkanoyl, hydroxy, alkoxy, alkylthio, alkylsulfinyl, alkylsulfonyl, halo, alkyl or haloalkyl;
(2) heterocyclyl radical optionally substituted by 1–3 radicals of amino, alkylamino, dialkylamino, alkanoylamino, alkoxycarbonylamino, alkylsulfonylamino, hydroxy, alkoxy, alkylthio, alkyl or haloalkyl; or
(3) aryl or heteroaryl radicals optionally substituted by 1–3 radicals of amino, alkylamino, dialkylamino, alkanoylamino, alkoxycarbonylamino, alkylsulfonylamino, alkoxycarbonyl, hydroxy, alkoxy, alkylthio, cyano, halo, azido, alkyl or haloalkyl;

each $R_{21}$ is independently hydrogen radical or $R_{20}$;
each $R_{22}$ is independently
(1) hydrogen radical;
(2) alkyl radical optionally substituted by a radical of heterocyclyl, aryl or heteroaryl optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl; or
(3) heterocyclyl, aryl or heteroaryl radicals optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl;
$R_{12}$ is an "N"-heteroaryl radical, and $R_{11}$ is an aryl radical or heteroaryl radical other than an "N"-heteroaryl radical, wherein the "N"-heteroaryl radical, aryl radical and heteroaryl radical other than an "N"-heteroaryl radical are each optionally substituted by 1–3 radicals of
(1) $R_{30}$;
(2) halo or cyano radicals;
(3) —C(O)—$R_{30}$, —C(O)—O$R_{29}$, —C(O)—N$R_{31}R_{32}$ or —C(N$R_{31}$)—N$R_{31}R_{32}$ radicals;
(4) —O$R_{29}$, —O—C(O)—$R_{29}$, —O—C(O)—N$R_{31}R_{32}$ or —O—C(O)—N$R_{33}$—S(O)$_2$—$R_{30}$ radicals;
(5) —S$R_{29}$, —S(O)—$R_{30}$, —S(O)$_2$—$R_{30}$, —S(O)$_2$—N$R_{31}R_{32}$, —S(O)$_2$—N$R_{33}$—C(O)—$R_{30}$, —S(O)$_2$—N$R_{33}$—C(O)—O$R_{30}$ or —S(O)$_2$—N$R_{33}$—C(O)—N$R_{31}R_{32}$ radicals; or
(6) —N$R_{31}R_{32}$, —N$R_{33}$—C(O)—$R_{29}$, —N$R_{33}$—C(O)—O$R_{30}$, —N$R_{33}$—C(O)—N$R_{31}R_{32}$, —N$R_{33}$—C(N$R_{31}$)—N$R_{31}R_{32}$, —N$R_{33}$—S(O)$_2$—$R_{30}$ or —N$R_{33}$—S(O)$_2$—N$R_{31}R_{32}$ radicals;
provided that the total number of aryl, heteroaryl, cycloalkyl and heterocyclyl radicals substituted on each of $R_{11}$ and $R_{12}$ is 0–1;
each $R_{30}$ is independently
(1) alkyl, alkenyl or alkynyl radicals optionally substituted by 1–3 radicals of —N$R_{31}R_{31}$, —CO$_2R_{23}$, hydroxy, alkoxy, alkylthio, alkylsulfinyl, alkylsulfonyl, cyano, halo or aralkoxy, aralkylthio, aralkylsulfonyl, heterocyclyl, aryl or heteroaryl radicals optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl;
(2) heterocyclyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or
(3) aryl or heteroaryl radicals optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl or haloalkyl;
$R_{29}$ is independently hydrogen radical or $R_{30}$;
each $R_{31}$ is independently
(1) hydrogen radicals;
(2) alkyl radical optionally substituted by an cycloalkyl, aryl, heterocyclyl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or (3) aryl, heteroaryl, heterocyclyl or cycloalkyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl;
each $R_{32}$ is independently
(1) hydrogen radicals;
(2) alkyl radical optionally substituted by an cycloalkyl, aryl, heterocyclyl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or
(3) aryl, heteroaryl, heterocyclyl or cycloalkyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; and
each $R_{33}$ is independently
(1) hydrogen radical; or
(2) alkyl radical optionally substituted by a radical of heterocyclyl, aryl or heteroaryl optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; and
provided that the compound is not 3-phenyl-2-(trifluoromethylpyrazolyl)pyridine; and when X is C—H, then Q is other than a phenyl radical; and when X is N and J is C—$R_1$ or C—$R_2$, $R_{11}$ is other than an (alkylsulfonyl)phenyl, (aminosulfonyl)phenyl, (haloalkylsulfonyl)phenyl, 4-(trifluoromethylcarbonylaminosulfonyl)phenyl, 4-(methylaminosulfonyl)phenyl or 4-(tertbutylaminosulfonyl)phenyl radical.

2. The compound of claim 1 or a pharmaceutically acceptable salt thereof, wherein
$R_2$ is (1) a hydrogen, halo, trifluoromethyl, cyano, —C(O)—O$R_{21}$ or —C(O)—N$R_5R_{21}$ radical;
(2) $C_1$–$C_8$ alkyl radical optionally substituted by (a) 1–2 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy or $C_1$–$C_4$ alkylthio, and (b) a radical of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, halo, $C_1$–$C_4$ alkyl, carboxy, carboxamide, trifluoromethoxy or trifluoromethyl radicals; or
(3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, carboxy, carboxamide, trifluoromethoxy or trifluoromethyl radicals;
each Z is independently a
(1) $C_1$–$C_8$ alkyl, $C_2$–$C_8$ alkenyl or $C_2$–$C_8$ alkynyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_{1-C4}$ alkoxy)carbonylamino, $C_1$–$C_4$ alkylsulfonylamino, hydroxy, $C_1$–$C_4$ alkoxy, $C_1$–$C_4$ alkylthio or halo, and (b) 1–2 radicals of heterocyclyl, aryl or heteroaryl; or
(2) heterocyclyl, aryl or heteroaryl radical;
wherein the heterocyclyl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkyl, aryl-$C_1$–$C_4$ alkyl, heteroaryl-$C_1$–$C_4$ alkyl or $C_1$–$C_4$ haloalkyl of 1–3 halo radicals; and the aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;

each $R_5$ is independently (1) hydrogen radicals;

(2) $C_1$–$C_8$ alkyl, $C_2$–$C_8$ alkenyl or $C_2$–$C_8$ alkynyl radicals optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, —$SO_3H$ or halo; or (3) aryl, heteroaryl, aryl-$C_1$–$C_4$-alkyl, heteroaryl-$C_1$–$C_4$-alkyl, heterocyclyl, heterocyclyl-$C_1$–$C_4$-alkyl, $C_3$–$C_8$ cycloalkyl or $C_3$–$C_8$-cycloalkyl-$C_1$–$C_4$-alkyl radicals optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, $C_1$–$C_4$ alkyl or $C_1$–$C_4$ haloalkyl of 1–3 halo radicals;

each $R_{20}$ is independently (1) $C_1$–$C_8$ alkyl, $C_2$–$C_8$ alkenyl or $C_2$–$C_8$ alkynyl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo or aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, hydroxy, $C_1$–$C_4$ alkoxy, $C_1$–$C_4$ alkylthio, $C_1$–$C_4$ alkylsulfinyl, $C_1$–$C_4$ alkylsulfonyl, halo, $C_1$–$C_4$ alkyl or $C_1$–$C_4$ haloalkyl of 1–3 halo radicals;

(2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkyl or $C_1$–$C_4$ haloalkyl of 1–3 halo radicals; or (3) aryl or heteroaryl radicals optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or $C_1$–$C_4$ haloalkyl of 1–3 halo radicals;

each $R_{21}$ is independently hydrogen radical or $R_{20}$;

each $R_{22}$ is independently (1) hydrogen radical;

(2) $C_1$–$C_4$ alkyl radical optionally substituted by a radical of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals; or (3) heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals;

each $R_{30}$ is independently (1) $C_1$–$C_4$ alkyl radical optionally substituted by 1–3 radicals of (a) —$NR_{31}R_{31}$;

(b) $C_1$–$C_4$ alkoxy-carbonyl or phenoxycarbonyl or phenylmethoxycarbonyl optionally substituted by 1–3 radicals of amino, alkylamino, di-($C_1$–$C_4$-alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or trifluoromethyl; or (c) hydroxy, $C_1$–$C_4$ alkoxy, $C_1$–$C_4$ alkylthio, or phenyl-$C_1$–$C_4$-alkoxy, phenyl-$C_1$–$C_4$-alkylthio, heterocyclyl, phenyl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;

(2) $C_1$–$C_4$ haloalkyl of 1–3 halo radical; or (3) aryl or heteroaryl radicals optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, hydroxy, $C_1$–$C_4$ alkoxy, $C_1$–$C_4$ alkylthio, cyano, halo, $C_1$–$C_4$ alkyl or trifluoromethyl radicals;

$R_{29}$ is independently hydrogen radical or $R_{30}$;

each $R_{31}$ is independently (1) hydrogen radicals;

(2) $C_1$–$C_4$ alkyl radical optionally substituted by an $C_3$–$C_8$ cycloalkyl, aryl, heterocyclyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or (3) aryl, heteroaryl, heterocyclyl or $C_3$–$C_8$ cycloalkyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

each $R_{32}$ is independently (1) hydrogen radicals;

(2) $C_1$–$C_4$ alkyl radical optionally substituted by an $C_3$–$C_8$ cycloalkyl, aryl, heterocyclyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or (3) aryl, heteroaryl, heterocyclyl or $C_3$–$C_8$ cycloalkyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; and each $R_{33}$ is independently (1) hydrogen radical; or (2) $C_1$–$C_4$ alkyl radical optionally substituted by a radical of heterocyclyl, aryl or heteroaryl optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; and wherein heterocyclyl is a radical of a monocyclic or bicyclic saturated heterocyclic ring system having 5–8 ring members per ring, wherein 1–3 ring members are oxygen, sulfur or nitrogen heteroatoms, which is optionally partially unsaturated or benzo-fused and optionally substituted by 1–2 oxo or thioxo radicals; aryl is a phenyl or naphthyl radical; and heteroaryl is radical of a monocyclic or bicyclic aromatic heterocyclic ring system having 5–6 ring members per ring, wherein 1–3 ring members are oxygen, sulfur or nitrogen heteroatoms, which is optionally benzo-fused or saturated $C_3$–$C_4$-carbocyclic-fused.

3. The compound of claim 2 or a pharmaceutically acceptable salt thereof, wherein $R_2$ is (1) a hydrogen, halo, trifluoromethyl, cyano, carboxy or carboxamide radical;

(2) $C_1$–$C_8$ alkyl radical optionally substituted by (a) 1–2 radicals of amino, $C_1$–$C_4$ alkylamino, di-($C_1$–$C_4$ alkyl)amino, hydroxy, $C_1$–$C_4$ alkoxy or $C_1$–$C_4$ alkylthio; or (3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl, carboxy, carboxamide, trifluoromethoxy or trifluoromethyl radicals;

each Z is independently a (1) $C_1$–$C_8$ alkyl or $C_2$–$C_8$ alkenyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio or halo, and (b) 1–2 radicals of heterocyclyl, aryl or heteroaryl; or (2) heterocyclyl, aryl or heteroaryl radical;

wherein the heterocyclyl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, $C_1$–$C_4$ alkyl, aryl-$C_1$–$C_4$ alkyl, heteroaryl-$C_1$–$C_4$ alkyl or $C_1$–$C_2$ haloalkyl of 1–3 halo radicals; and the aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;

each Y is independently a (1) hydrogen or halo radical;

(2) —C(O)—$R_{20}$, —C(O)—$OR_{21}$, —C(O)—$NR_5R_{21}$ or —C($NR_5$)—$NR_5R_{21}$ radical;

(3) —$OR_{21}$, —O—C(O)—$R_{21}$ or —O—C(O)—$NR_5R_{21}$ radical;

(4) —$SR_{21}$, —S(O)—$R_{20}$, —S(O)$_2$—$R_{20}$ or —S(O)$_2$—$NR_5R_{21}$ radical; or (5) —$NR_5R_{21}$, —$NR_{22}$—C(O)—$R_{21}$, —$NR_{22}$—C(O)—$OR_{20}$ or —$NR_{22}$—C(O)—$NR_5R_{21}$ radical;

each $R_5$ is independently (1) hydrogen radicals;

(2) $C_1$–$C_4$ alkyl or $C_2$–$C_5$ alkenyl radicals optionally substituted by 1–3 radicals of amino, di-($C_1$–$C_4$-alkyl)amino, hydroxy, $C_1$–$C_4$ alkoxy, $C_1$–$C_4$ alkylthio, —$SO_3H$ or halo; or (3) phenyl-$C_1$–$C_2$-alkyl, heteroaryl-$C_1$–$C_2$-alkyl, heterocyclyl-$C_1$–$C_2$-alkyl or $C_3$–$C_6$-cycloalkyl-$C_1$–$C_2$- alkyl radicals optionally substituted by 1–3 radicals of amino, di-($C_1$–$C_4$-alkyl)amino, hydroxy, $C_1$–$C_4$ alkoxy, $C_1$–$C_4$ alkylthio, $C_1$–$C_4$ alkyl or $C_1$–$C_2$ haloalkyl of 1–3 halo radicals;

each $R_{20}$ is independently (1) $C_1$–$C_8$ alkyl or $C_2$–$C_5$ alkenyl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo or aryl-$C_1$–$C_4$-alkoxy, aryl-$C_1$–$C_4$-alkylthio, aryl-$C_1$–$C_4$-alkylsulfonyl, $C_3$–$C_6$ cycloalkyl, heterocyclyl, aryl or heteroaryl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, hydroxy, $C_1$–$C_4$ alkoxy, $C_1$–$C_4$ alkylthio, halo, $C_1$–$C_4$ alkyl or $C_1$–$C_2$ haloalkyl of 1–3 halo radicals;

(2) heterocyclyl radical optionally substituted by 1–2 radicals of amino, di-($C_1$–$C_4$ alkyl)amino, ($C_1$–$C_4$ alkoxy)carbonylamino, hydroxy, $C_1$–$C_4$ alkoxy, $C_1$–$C_4$ alkylthio or $C_1$–$C_4$ alkyl; or (3) aryl or heteroaryl radicals optionally substituted by 1–2 radicals of amino, $C_1$–$C_4$ alkylamino, di-($C_1$–$C_4$ alkyl)amino, acetamido, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or trifluoromethyl radicals;

each $R_{21}$ is independently hydrogen radical or $R_{20}$;

each $R_{22}$ is independently (1) hydrogen radical; or (2) $C_1$–$C_4$ alkyl radical optionally substituted by a radical of phenyl or heteroaryl optionally substituted by 1–3 radicals of amino, di-($C_1$–$C_2$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;

$R_{12}$ is an "N"-heteroaryl radical, and $R_{11}$ is an aryl radical or heteroaryl radical other than an "N"-heteroaryl radical, wherein the "N"-heteroaryl radical, aryl radical and heteroaryl radical other than an "N"-heteroaryl radical are each optionally substituted by 1–2 radicals of (1) $R_{30}$;

(2) halo or cyano radicals;

(3) —C(O)—$R_{30}$, —C(O)—$OR_{29}$, —C(O)—$NR_{31}R_{32}$ or —C($NR_{31}$)—$NR_{31}R_{32}$ radicals; or (4) —$OR_{29}$, —$SR_{29}$, —S(O)—$R_{30}$, —S(O)$_2$—$R_{30}$, —S(O)$_2$—$NR_{31}R_{32}$, —$NR_{31}R_{32}$ or —$NR_{33}$—C(O)—$R_{29}$ radicals;

each $R_{30}$ is independently (1) $C_1$–$C_4$ alkyl radical optionally substituted by a phenyl or heteroaryl radical optionally substituted by 1–3 radicals of amino, di-($C_1$–$C_2$ alkyl)amino, acetamido, hydroxy, $C_1$–$C_2$ alkoxy, halo, $C_1$–$C_4$ alkyl or trifluoromethyl radicals;

(2) trifluoromethyl radical; or (3) aryl or heteroaryl radicals optionally substituted by 1–3 radicals of amino, di-($C_1$–$C_2$ alkyl)amino, acetamido, hydroxy, $C_1$–$C_2$ alkoxy, halo, $C_1$–$C_4$ alkyl or trifluoromethyl radicals;

$R_{29}$ is independently hydrogen radical or $R_{30}$;

each $R_{31}$ is independently (1) hydrogen radicals; or (2) $C_1$–$C_4$ alkyl radical optionally substituted by an phenyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, $C_1$–$C_4$ alkyl or trifluoromethyl radicals;

each $R_{32}$ is independently
(1) hydrogen radicals;
(2) $C_1$–$C_4$ alkyl radical optionally substituted by phenyl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkyl or trifluoromethyl radicals; or
(3) phenyl or heteroaryl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, hydroxy, $C_1$–$C_4$ alkoxy, $C_1$–$C_4$ alkyl or trifluoromethyl radicals; and each $R_{33}$ is independently hydrogen or $C_1$–$C_4$ alkyl radical.

4. The compound of claim 3 or a pharmaceutically acceptable salt thereof, wherein W is $R_1$, $R_2$ or O;

$R_1$ is —Z—Y or —Y; and each $R_3$ is independently a hydrogen radical or —Z—Y; provided that the total number of aryl, heteroaryl, cycloalkyl and heterocyclyl radicals in $R_1$, $R_2$ and $R_3$ is 0–2;

$R_2$ is (1) a hydrogen, halo, trifluoromethyl or cyano radical; or
(2) $C_1$–$C_4$ alkyl radical optionally substituted by (a) 1–2 radicals of amino, $C_1$–$C_4$ alkylamino or di-($C_1$–$C_4$ alkyl) amino;

each Z is independently a
(1) $C_1$–$C_4$ alkyl or $C_2$–$C_5$ alkenyl radical optionally substituted by (a) 1–3 radicals of amino, di-($C_1$–$C_2$ alkyl) amino, $C_1$–$C_5$ alkanoylamino, ($C_1$–$C_4$ alkoxy) carbonylamino, hydroxy, $C_1$–$C_2$ alkoxy, $C_1$–$C_2$ alkylthio or halo, and (b) 1–2 radicals of heterocyclyl, aryl or heteroaryl; or
(2) heterocyclyl, aryl or heteroaryl radical;
wherein the heterocyclyl radicals are optionally substituted by 1–3 radicals of amino, di-($C_1$–$C_2$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, $C_1$–$C_4$ alkyl, aryl-$C_1$–$C_4$ alkyl, heteroaryl-$C_1$–$C_4$ alkyl or trifluoromethyl radicals; and the aryl and heteroaryl radicals are optionally substituted by 1–3 radicals of amino, di-($C_1$–$C_2$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or trifluoromethyl radicals;

each Y is independently a
(1) hydrogen radical;
(2) —C(O)—$R_{20}$ or —C(O)—$NR_5R_{21}$ radical;
(3) —$OR_{21}$, —$SR_{21}$, —S(O)—$R_{20}$, —S(O)$_2$—$R_{20}$ or —S(O)$_2$—$NR_5R_{21}$ radical; or
(4) —$NR_5R_{21}$ or —$NR_{22}$—C(O)—$R_{21}$ radical;

each $R_5$ is independently
(1) hydrogen radical;
(2) $C_1$–$C_4$ alkyl radical optionally substituted by 1–3 radicals of amino, di-($C_1$–$C_2$-alkyl)amino, hydroxy, $C_1$–$C_2$ alkoxy, $C_1$–$C_2$ alkylthio or halo; or
(3) phenyl-$C_1$–$C_2$-alkyl, heteroaryl-$C_1$–$C_2$-alkyl, heterocyclyl-$C_1$–$C_2$-alkyl or $C_3$–$C_6$-cycloalkyl-$C_1$–$C_2$-alkyl radicals optionally substituted by 1–3 radicals of amino, di-($C_1$–$C_2$-alkyl)amino, hydroxy, $C_1$–$C_2$ alkoxy, $C_1$–$C_2$ alkylthio, methoxy, methylthio, $C_1$–$C_4$ alkyl or trifluoromethyl radicals;

each $R_{20}$ is independently
(1) $C_1$–$C_8$ alkyl radicals optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N-(($C_1$–$C_4$ alkoxy)carbonyl)-N-($C_1$–$C_4$ alkyl)amino, aminocarbonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, halo or $C_3$–$C_6$ cycloalkyl, heterocyclyl, aryl or heteroaryl radicals optionally substituted by 1–2 radicals of amino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, halo, $C_1$–$C_4$ alkyl or trifluoromethyl radicals;
(2) heterocyclyl radical optionally substituted by 1–2 radicals of hydroxy, $C_1$–$C_4$ alkoxy, $C_1$–$C_4$ alkylthio or $C_1$–$C_4$ alkyl; or
(3) aryl or heteroaryl radicals optionally substituted by 1–2 radicals of ($C_1$–$C_4$ alkoxy)carbonyl, amino, $C_1$–$C_4$ alky amino, di-($C_1$–$C_4$ alkyl)amino, hydroxy, $C_1$–$C_4$ alkoxy, $C_1$–$C_4$ alkylthio, cyano, halo, azido, $C_1$–$C_4$ alkyl or trifluoromethyl radicals;

each $R_{21}$ is independently hydrogen radical or $R_{20}$;

each $R_{22}$ is independently hydrogen or $C_1$–$C_4$ alkyl radical;

$R_{12}$ is an "N"-heteroaryl radical, and $R_{11}$ is an aryl radical or heteroaryl radical other than an "N"-heteroaryl radical, wherein the "N"-heteroaryl radical, aryl radical and heteroaryl radical other than an "N"-heteroaryl radical are each optionally substituted by 1–2 radicals of
(1) $R_{30}$;
(2) halo or cyano radicals; or
(3) —C(O)—$NR_{31}R_{32}$, —$OR_{29}$, —$SR_{29}$, —S(O)—$R_{30}$, —S(O)$_2$—$R_{30}$, —S(O)$_2$—$NR_{31}R_{32}$, —$NR_{31}R_{32}$ or —$NR_{33}$—C(O)—$R_{29}$, radicals;

each $R_{30}$ is independently
(1) $C_1$–$C_4$ alkyl radical optionally substituted by a phenyl or heteroaryl radical optionally substituted by 1–3 radicals of amino, dimethylamino, acetamido, hydroxy, halo, methoxy, methyl or trifluoromethyl radicals;
(2) trifluoromethyl radical; or
(3) aryl or heteroaryl radicals optionally substituted by 1–3 radicals of amino, dimethylamino, acetamido, hydroxy, halo, methoxy, methyl or trifluoromethyl radicals;

each $R_{29}$ is independently hydrogen radical or $R_{30}$; and each $R_{32}$ is independently
(1) hydrogen radicals;
(2) $C_1$–$C_4$ alkyl radical or $C_1$–$C_2$ alkyl radical substituted by phenyl or heteroaryl radical optionally substituted by 1–3 radicals of amino, dimethylamino, acetamido, hydroxy, methoxy, methyl or trifluoromethyl radicals; or
(3) phenyl or heteroaryl radical optionally substituted by 1–3 radicals of amino, dimethylamino, acetamido, hydroxy, methoxy, methyl or trifluoromethyl radicals; and wherein heterocyclyl is a radical of a monocyclic saturated heterocyclic ring system having 5–6 ring members, wherein 1–3 ring members are oxygen, sulfur or nitrogen heteroatoms, which is optionally benzo-fused and optionally substituted by 1–2 oxo or thioxo radicals; aryl is a phenyl or naphthyl radical; and heteroaryl is radical of a monocyclic aromatic heterocyclic ring system having 5–6 ring members, wherein 1–3 ring members are oxygen, sulfur or nitrogen heteroatoms, which is optionally benzo-fused or saturated $C_3$–$C_4$-carbocyclic-fused.

5. The compound of claim 4 or a pharmaceutically acceptable salt thereof, wherein W is $R_1$ or $R_2$;

X is N and J is C—$R_1$ or C—$R_2$, or X is C—H and J is N;

<u>a</u> is a double bond and <u>b</u> is a single bond; and when W is $R_1$, then J is other than C—$R_1$; when W is $R_2$, then J is other than C—$R_2$;

each Z is independently a
(1) $C_1$–$C_4$ alkyl or $C_2$–$C_5$ alkenyl radical optionally substituted by (a) 1–3 radicals of amino, di-($C_1$–$C_2$ alkyl)amino, ($C_1$–$C_4$ alkoxy)carbonylamino, hydroxy, $C_1$–$C_2$ alkoxy, $C_1$–$C_2$ alkylthio or halo, and (b) 1–2 radicals of aryl or heteroaryl; or
(2) heterocyclyl, aryl or heteroaryl radical;
wherein the heterocyclyl radicals are optionally substituted by 1–2 radicals of $C_1$–$C_4$ alkyl or aryl-$C_1$–$C_2$ alkyl radicals; and the aryl and heteroaryl radicals are optionally substituted by 1–3 radicals of amino, di-($C_1$–$C_2$ alkyl)amino, acetamido, ($C_1$–$C_4$ alkoxy)carbonylamino, hydroxy, $C_1$–$C_2$ alkoxy, $C_1$–$C_2$ alkylthio, cyano, halo, $C_1$–$C_4$ alkyl or trifluoromethyl radicals;
each Y is independently a hydrogen, —$OR_{21}$, —$SR_{21}$, —S(O)—$R_{20}$, —S(O)$_2$—$R_{20}$ or —$NR_5R_{21}$ radical;
each $R_5$ is independently
(1) hydrogen radical;
(2) $C_1$–$C_4$ alkyl radical optionally substituted by 1–3 halo radicals; or
(3) phenyl-$C_1$–$C_2$-alkyl or heteroaryl-$C_1$–$C_2$-alkyl, radicals optionally substituted by 1–3 radicals of amino, dimethylamino, hydroxy, methoxy, methylthio, methyl or trifluoromethyl radicals;
each $R_{20}$ is independently
(1) $C_1$–$C_6$ alkyl radicals optionally substituted by 1–3 radicals of amino, methylamino, dimethylamino, t-butoxycarbonylamino, N-((t-butoxy)carbonyl)-N-(methyl)amino, aminocarbonylamino, hydroxy, butoxy, methoxy, butylthio, methylthio, methylsulfinyl, methylsulfonyl, halo or $C_5$–$C_6$ cycloalkyl, heterocyclyl, phenyl or heteroaryl radicals optionally substituted by 1–2 radicals of amino, dimethylamino, acetamino, hydroxy, methoxy, methylthio, halo, methyl or trifluoromethyl radicals;
(2) heterocyclyl radical optionally substituted by 1–2 radicals of hydroxy or $C_1$–$C_4$ alkyl; or
(3) aryl or heteroaryl radicals optionally substituted by 1–2 radicals of amino, dimethylamino, hydroxy, methoxy, methylthio, halo, methyl or trifluoromethyl radicals;
each $R_{21}$ is independently hydrogen radical or $R_{20}$;
$R_{11}$ is an aryl radical or heteroaryl radical other than an "N"-heteroaryl radical, optionally substituted by 1–2 radicals of (1) $R_{30}$; (2) halo or cyano radicals; or (3) —C(O)—$NR_{31}R_{32}$, —$OR_{29}$, —$SR_{29}$, —S(O)—$R_{30}$, —S(O)$_2$—$R_{30}$, —S(O)$_2$—$NR_{31}R_{32}$, —$NR_{31}R_{32}$ or —$NR_{33}$—C(O)—$R_{29}$ radicals;
$R_{12}$ is an "N"-heteroaryl radical optionally substituted by 1–2 radicals of (1) $R_{30}$; (2) halo or cyano radicals; or (3) —C(O)—$NR_{31}R_{32}$, —$OR_{29}$, —$SR_{29}$, —$NR_{31}R_{32}$ or —$NR_{33}$—C(O)—$R_{29}$ radicals;
$R_{30}$ is independently
(1) $C_1$–$C_4$ alkyl radical optionally substituted by a phenyl or heteroaryl radical optionally substituted by 1–2 radicals of amino, dimethylamino, acetamido, hydroxy, halo, methoxy, methyl or trifluoromethyl radicals;
(2) trifluoromethyl radical; or
(3) aryl or heteroaryl radicals optionally substituted by 1–3 radicals of amino, dimethylamino, acetamido, hydroxy, halo, methoxy, methyl or trifluoromethyl radicals;
each $R_{29}$ is independently hydrogen radical or $R_{30}$;
each $R_{31}$ is independently hydrogen or $C_1$–$C_4$ alkyl radicals;
$R_{32}$ is independently
(1) hydrogen or $C_1$–$C_4$ alkyl radical; or
(2) phenyl or heteroaryl radical optionally substituted by 1–2 radicals of amino, dimethylamino, acetamido, hydroxy, methoxy, methyl or trifluoromethyl radicals; and each $R_{33}$ is independently hydrogen or $C_1$–$C_4$ alkyl radical; and
wherein heterocyclyl is a radical of a monocyclic saturated heterocyclic ring system having 5–6 ring members, wherein 1–2 ring members are oxygen, sulfur or nitrogen heteroatoms, which is optionally benzo-fused and optionally substituted by 1–2 oxo or thioxo radicals; aryl is a phenyl or naphthyl radical; and heteroaryl is radical of a monocyclic aromatic heterocyclic ring system having 5–6 ring members, wherein 1–2 ring members are oxygen, sulfur or nitrogen heteroatoms, which is optionally benzo-fused.

6. The compound of claim 5 or a pharmaceutically acceptable salt thereof, wherein
each Z is independently a
(1) $C_1$–$C_4$ alkyl radical optionally substituted by (a) 1–2 radicals of amino, di-($C_1$–$C_2$ alkyl)amino, hydroxy, $C_1$–$C_2$ alkoxy or $C_1$–$C_2$ alkylthio, and (b) an aryl radical; or
(2) a heterocyclyl radical optionally substituted by 1–2 radicals of $C_1$–$C_2$ alkyl or aryl-$C_1$–$C_2$ alkyl radicals;
wherein the aryl radicals are optionally substituted by 1–2 radicals of amino, di-($C_1$–$C_2$ alkyl)amino, hydroxy, $C_1$–$C_2$ alkoxy, $C_1$–$C_2$ alkylthio, cyano, halo, $C_1$–$C_2$ alkyl or trifluoromethyl radicals;
each Y is independently a —$OR_{21}$, —$SR_{21}$ or —$NR_5R_{21}$ radical;
each $R_5$ is independently hydrogen or $C_1$–$C_4$ alkyl radical;
each $R_{20}$ is independently
(1) $C_1$–$C_6$ alkyl radicals optionally substituted by 1–3 radicals of amino, methylamino, dimethylamino, t-butoxycarbonylamino, N-((t-butoxy)carbonyl)-N-(methyl)amino, aminocarbonylamino, hydroxy, butoxy, methoxy, butylthio, methylthio, methylsulfinyl, methylsulfonyl, halo or $C_5$–$C_6$ cycloalkyl, heterocyclyl, phenyl or heteroaryl radicals optionally substituted by 1–2 radicals of amino, dimethylamino, acetamino, hydroxy, methoxy, methylthio, halo, methyl or trifluoromethyl radicals;
(2) heterocyclyl radical; or
(3) aryl or heteroaryl radicals optionally substituted by 1–2 radicals of amino, dimethylamino, hydroxy, methoxy, methylthio, halo, methyl or trifluoromethyl radicals;
each $R_{21}$ is independently hydrogen radical or $R_{20}$;
$R_{11}$ is an unsubstituted phenyl or naphthyl radical or a phenyl radical substituted by 1–2 radicals of methyl, amino, dimethylamino, acetamido, hydroxy, halo, cyano, methoxy, methylthio, methylsulfinyl, methylsulfonyl, aminocarbonyl, methyl or trifluoromethyl radicals; and
$R_{12}$ is a 4-pyridyl, 4-pyrimidyl, 4-quinolinyl, 7-imidazo[4,5-b]pyridinyl, 8-quinazolinyl, 6-(1H)-purinyl, or a 4-imidazolyl radical optionally substituted by a radical of amino, dimethylamino, acetamido, hydroxy, halo, cyano, methoxy, methyl or trifluoromethyl radicals.

7. The compound of claim 6 or a pharmaceutically acceptable salt thereof, wherein
W is $R_1$;
A is $R_{12}$ and Q is $R_{11}$;
X is N and J is C—$R_2$, or X is C—H and J is N; and
<u>a</u> is a double bond and <u>b</u> is a single bond;
$R_2$ is a hydrogen, halo, trifluoromethyl, cyano or $C_1$–$C_4$ alkyl radical;
each Z is independently a
(1) $C_1$–$C_4$ alkyl radical optionally substituted by 1–2 radicals of amino, dimethylamino or phenyl radical; or
(2) a heterocyclyl radical optionally substituted by 1–2 radicals of methyl or phenylmethyl;
wherein the phenyl radicals are optionally substituted by 1–2 radicals of amino, di-($C_1$–$C_2$ alkyl)amino, hydroxy, $C_1$–$C_2$ alkoxy, $C_1$–$C_2$ alkylthio, cyano, halo, $C_1$–$C_2$ alkyl or trifluoromethyl radicals;
each $R_5$ is a hydrogen or methyl radical;
each $R_{20}$ is independently
(1) $C_1$–$C_6$ alkyl radicals optionally substituted by 1–3 radicals of amino, methylamino, dimethylamino, hydroxy or phenyl or heteroaryl radicals optionally substituted by 1–2 radicals of amino, dimethylamino, hydroxy, methoxy, methylthio, halo, methyl or trifluoromethyl radicals;
(2) heterocyclyl radical; or
(3) aryl or heteroaryl radicals optionally substituted by 1–2 radicals of amino, dimethylamino, hydroxy, methoxy, methylthio, halo, methyl or trifluoromethyl radicals;
each $R_{21}$ is independently hydrogen radical or $R_{20}$;
$R_{11}$ is an unsubstituted phenyl radical or a phenyl radical substituted by 1–2 radicals of methyl, amino, dimethylamino, acetamido, hydroxy, halo, cyano, methoxy, methylthio, methylsulfonyl, methyl or trifluoromethyl radicals; and
$R_{12}$ is a 4-pyridyl or 4-pyrimidyl radical optionally substituted by a radical of amino, dimethylamino, acetamido, hydroxy, halo, cyano, methoxy, methyl or trifluoromethyl radicals.

8. The compound of claim 5 or a pharmaceutically acceptable salt thereof, wherein
W is $R_2$;
A is $R_{11}$ and Q is $R_{12}$;
X is N and J is C—$R_1$; and
a is a double bond and b is a single bond;
$R_2$ is a hydrogen, halo, trifluoromethyl, cyano or $C_1$–$C_4$ alkyl radical;
each Z is independently a
(1) $C_1$–$C_4$ alkyl radical optionally substituted by 1–2 radicals of amino, dimethylamino or phenyl radical; or
(2) a heterocyclyl radical optionally substituted by 1–2 radicals of methyl or phenylmethyl;
wherein the phenyl radicals are optionally substituted by 1–2 radicals of amino, di-($C_1$–$C_2$ alkyl)amino, hydroxy, $C_1$–$C_2$ alkoxy, $C_1$–$C_2$ alkylthio, cyano, halo, $C_1$–$C_2$ alkyl or trifluoromethyl radicals;
each $R_5$ is a hydrogen or methyl radical;
each $R_{20}$ is independently
(1) $C_1$–$C_6$ alkyl radicals optionally substituted by 1–3 radicals of amino, methylamino, dimethylamino, hydroxy or phenyl or heteroaryl radicals optionally substituted by 1–2 radicals of amino, dimethylamino, hydroxy, methoxy, methylthio, halo, methyl or trifluoromethyl radicals;
(2) heterocyclyl radical; or
(3) aryl or heteroaryl radicals optionally substituted by 1–2 radicals of amino, dimethylamino, hydroxy, methoxy, methylthio, halo, methyl or trifluoromethyl radicals;
each $R_{21}$ is independently hydrogen radical or $R_{20}$;
$R_{11}$ is an unsubstituted phenyl radical or a phenyl radical substituted by 1–2 radicals of methyl, amino, dimethylamino, acetamido, hydroxy, halo, cyano, methoxy, methylthio, methylsulfonyl, methyl or trifluoromethyl radicals; and
$R_{12}$ is a 4-pyridyl or 4-pyrimidyl radical optionally substituted by a radical of amino, dimethylamino, acetamido, hydroxy, halo, cyano, methoxy, methyl or trifluoromethyl radicals.

9. The compound of claim 4 or a pharmaceutically acceptable salt thereof, wherein
W is O;
A is $R_{11}$ and Q is $R_{12}$, or A is $R_{12}$ and Q is $R_{11}$;
X is C—H;
J is N—$R_3$; and
a is a single bond and b is a double bond;
each Z is independently a
(1) $C_1$–$C_4$ alkyl or $C_2$–$C_5$ alkenyl radical optionally substituted by (a) 1–3 radicals of amino, di-($C_1$–$C_2$ alkyl)amino, ($C_1$–$C_4$ alkoxy)carbonylamino, hydroxy, $C_1$–$C_2$ alkoxy, $C_1$–$C_2$ alkylthio or halo, and (b) 1–2 radicals of aryl or heteroaryl; or
(2) heterocyclyl, aryl or heteroaryl radical;
wherein the heterocyclyl radicals are optionally substituted by 1–2 radicals of $C_1$–$C_4$ alkyl or aryl-$C_1$–$C_2$ alkyl radicals; and the aryl and heteroaryl radicals are optionally substituted by 1–3 radicals of amino, di-($C_1$–$C_2$ alkyl)amino, acetamido, ($C_1$–$C_4$ alkoxy)carbonylamino, hydroxy, $C_1$–$C_2$ alkoxy, $C_1$–$C_2$ alkylthio, cyano, halo, $C_1$–$C_4$ alkyl or trifluoromethyl radicals;
each Y is independently a hydrogen, —$OR_{21}$, —$SR_{21}$, —S(O)—$R_{20}$, —S(O)$_2$—$R_{20}$ or —$NR_5R_{21}$ radical;
each $R_5$ is independently
(1) hydrogen radical;
(2) $C_1$–$C_4$ alkyl radical optionally substituted by 1–3 halo radicals; or
(3) phenyl-$C_1$–$C_2$-alkyl or heteroaryl-$C_1$–$C_2$-alkyl, radicals optionally substituted by 1–3 radicals of amino, dimethylamino, hydroxy, methoxy, methylthio, methyl or trifluoromethyl radicals;
each $R_{20}$ is independently
(1) $C_1$–$C_6$ alkyl radicals optionally substituted by 1–3 radicals of amino, methylamino, dimethylamino, t-butoxycarbonylamino, N-((t-butoxy)carbonyl)-N-(methyl)amino, aminocarbonylamino, hydroxy, butoxy, methoxy, butylthio, methylthio, methylsulfinyl, methylsulfonyl, halo or $C_5$–$C_6$ cycloalkyl, heterocyclyl, phenyl or heteroaryl radicals optionally substituted by 1–2 radicals of amino, dimethylamino, acetamino, hydroxy, methoxy, methylthio, halo, methyl or trifluoromethyl radicals;
(2) heterocyclyl radical optionally substituted by 1–2 radicals of hydroxy or $C_1$–$C_4$ alkyl; or
(3) aryl or heteroaryl radicals optionally substituted by 1–2 radicals of amino, dimethylamino, hydroxy, methoxy, methylthio, halo, methyl or trifluoromethyl radicals;
each $R_{21}$ is independently hydrogen radical or $R_{20}$;
$R_{11}$ is an aryl radical or heteroaryl radical other than an "N"-heteroaryl radical, optionally substituted by 1–2 radicals of (1) $R_{30}$; (2) halo or cyano radicals; or (3) —C(O)—$NR_{31}R_{32}$, —$OR_{29}$, —$SR_{29}$, —S(O)—$R_{30}$, —S(O)$_2$—$R_{30}$, —S(O)$_2$—$NR_{31}R_{32}$, —$NR_{31}R_{32}$ or —$NR_{33}$—C(O)—$R_{29}$ radicals;
$R_{12}$ is an "N"-heteroaryl radical optionally substituted by 1–2 radicals of (1) $R_{30}$; (2) halo or cyano radicals; or (3) —C(O)—$NR_{31}R_{32}$, —$OR_{29}$, —$SR_{29}$, —$NR_{31}R_{32}$ or —$NR_{33}$—C(O)—$R_{29}$ radicals;
$R_{30}$ is independently
(1) $C_1$–$C_4$ alkyl radical optionally substituted by a phenyl or heteroaryl radical optionally substituted by 1–2 radicals of amino, dimethylamino, acetamido, hydroxy, halo, methoxy, methyl or trifluoromethyl radicals;
(2) trifluoromethyl radical; or
(3) aryl or heteroaryl radicals optionally substituted by 1–3 radicals of amino, dimethylamino, acetamido, hydroxy, halo, methoxy, methyl or trifluoromethyl radicals;
each $R_{29}$ is independently hydrogen radical or $R_{30}$;
each $R_{31}$ is independently hydrogen or $C_1$–$C_4$ alkyl radicals;
$R_{32}$ is independently
(1) hydrogen or $C_1$–$C_4$ alkyl radical; or
(2) phenyl or heteroaryl radical optionally substituted by 1–2 radicals of amino, dimethylamino, acetamido, hydroxy, methoxy, methyl or trifluoromethyl radicals; and each $R_{33}$ is independently hydrogen or $C_1$–$C_4$ alkyl radical; and
wherein heterocyclyl is a radical of a monocyclic saturated heterocyclic ring system having 5–6 ring members, wherein 1–2 ring members are oxygen, sulfur or nitrogen heteroatoms, which is optionally benzo-fused and optionally substituted by 1–2 oxo or thioxo radicals; aryl is a phenyl or naphthyl radical; and heteroaryl is radical of a monocyclic aromatic heterocyclic ring system having 5–6 ring members, wherein 1–2 ring members are oxygen, sulfur or nitrogen heteroatoms, which is optionally benzo-fused.

10. The compound of claim 9 or a pharmaceutically acceptable salt thereof, wherein
A is $R_{11}$ and Q is $R_{12}$;
each Z is independently a
(1) $C_1$–$C_4$ alkyl radical optionally substituted by (a) 1–2 radicals of amino, di-($C_1$–$C_2$ alkyl)amino, hydroxy, $C_1$–$C_2$ alkoxy or $C_1$–$C_2$ alkylthio, and (b) an aryl radical; or
(2) a heterocyclyl radical optionally substituted by 1–2 radicals of $C_1$–$C_2$ alkyl or aryl-$C_1$–$C_2$ alkyl radicals;
wherein the aryl radicals are optionally substituted by 1–2 radicals of amino, di-($C_1$–$C_2$ alkyl)amino, hydroxy, $C_1$–$C_2$ alkoxy, $C_1$–$C_2$ alkylthio, cyano, halo, $C_1$–$C_2$ alkyl or trifluoromethyl radicals;
each Y is independently a —$OR_{21}$, —$SR_{21}$ or —$NR_5R_{21}$ radical;
each $R_5$ is independently hydrogen or $C_1$–$C_4$ alkyl radical;
each $R_{20}$ is independently
(1) $C_1$–$C_6$ alkyl radicals optionally substituted by 1–3 radicals of amino, methylamino, dimethylamino, t-butoxycarbonylamino, N-((t-butoxy)carbonyl)-N-(methyl)amino, aminocarbonylamino, hydroxy, butoxy, methoxy, butylthio, methylthio, methylsulfinyl, methylsulfonyl, halo or $C_5$–$C_6$ cycloalkyl, heterocyclyl, phenyl or heteroaryl radicals optionally substituted by 1–2 radicals of amino, dimethylamino, acetamino, hydroxy, methoxy, methylthio, halo, methyl or trifluoromethyl radicals;
(2) heterocyclyl radical; or
(3) aryl or heteroaryl radicals optionally substituted by 1–2 radicals of amino, dimethylamino, hydroxy, methoxy, methylthio, halo, methyl or trifluoromethyl radicals;
each $R_{21}$ is independently hydrogen radical or $R_{20}$;
$R_{11}$ is an unsubstituted phenyl or naphthyl radical or a phenyl radical substituted by 1–2 radicals of methyl, amino, dimethylamino, acetamido, hydroxy, halo, cyano, methoxy, methylthio, methylsulfinyl, methylsulfonyl, aminocarbonyl, methyl or trifluoromethyl radicals; and
$R_{12}$ is a 4-pyridyl, 4-pyrimidyl, 4-quinolinyl, 7-imidazo[4,5-b]pyridinyl, 8-quinazolinyl, 6-(1H)-purinyl, or a 4-imidazolyl radical optionally substituted by a radical of amino, dimethylamino, acetamido, hydroxy, halo, cyano, methoxy, methyl or trifluoromethyl radicals.

11. The compound of claim 10 or a pharmaceutically acceptable salt thereof, wherein
each Z is independently a
(1) $C_1$–$C_4$ alkyl radical optionally substituted by 1–2 radicals of amino, dimethylamino or phenyl radical; or
(2) a heterocyclyl radical optionally substituted by 1–2 radicals of methyl or phenylmethyl;
wherein the phenyl radicals are optionally substituted by 1–2 radicals of amino, di-($C_1$–$C_2$ alkyl)amino, hydroxy, $C_1$–$C_2$ alkoxy, $C_1$–$C_2$ alkylthio, cyano, halo, $C_1$–$C_2$ alkyl or trifluoromethyl radicals;
each $R_5$ is a hydrogen or methyl radical;
each $R_{20}$ is independently
(1) $C_1$–$C_6$ alkyl radicals optionally substituted by 1–3 radicals of amino, methylamino, dimethylamino, hydroxy or phenyl or heteroaryl radicals optionally substituted by 1–2 radicals of amino, dimethylamino, hydroxy, methoxy, methylthio, halo, methyl or trifluoromethyl radicals;
(2) heterocyclyl radical; or
(3) aryl or heteroaryl radicals optionally substituted by 1–2 radicals of amino, dimethylamino, hydroxy, methoxy, methylthio, halo, methyl or trifluoromethyl radicals;
each $R_{21}$ is independently hydrogen radical or $R_{20}$;
$R_{11}$ is an unsubstituted phenyl radical or a phenyl radical substituted by 1–2 radicals of methyl, amino, dimethylamino, acetamido, hydroxy, halo, cyano, methoxy, methylthio, methylsulfonyl, methyl or trifluoromethyl radicals; and
$R_{12}$ is a 4-pyridyl or 4-pyrimidyl radical optionally substituted by a radical of amino, dimethylamino, acetamido, hydroxy, halo, cyano, methoxy, methyl or trifluoromethyl radicals.

12. The compound of claim 1 which is:
1-(3-phenylpropyl)-4-(3-methylphenyl)-5-(4-pyridyl)-1H-pyrid-2-one;
2-(3-phenylpropoxy)-4-(3-methylphenyl)-5-(4-pyridyl) pyridine;
1-((S)-2-amino-3-phenylpropyl)-4-(3-methylphenyl)-5-(4-pyridyl)-1H-pyrid-2-one;
2-((S)-2-amino-3-phenylpropoxy)-4-(3-methylphenyl)-5-(4-pyridyl)pyridine;
2-(3-amino-3-phenylpropylamino)-5-(4-fluorophenyl)-4-(4-pyridinyl)pyridine;
2-(3-amino-3-phenylpropylamino)-5-(4-chlorophenyl)-4-(4-pyridinyl)pyridine;
2-(3-amino-3-phenylpropylamino)-5-(3-fluorophenyl)-4-(4-pyridinyl)pyridine;
2-(3-amino-3-phenylpropylamino)-5-(3-trifluoromethylphenyl)-4-(4-pyridinyl)pyridine;
2-(3-amino-3-phenylpropylamino)-5-(3-isopropylphenyl)-4-(4-pyridinyl)pyridine;
2-(3-amino-3-phenylpropylamino)-5-(3-methylphenyl)-4-(4-pyridinyl)pyridine;
2-((S)-2-amino-3-phenylpropylamino)-5-(4-fluorophenyl)-4-(4-pyridinyl)pyridine;
2-((S)-2-amino-3-phenylpropylamino)-5-(4-chlorophenyl)-4-(4-pyridinyl)pyridine;
2-((S)-2-amino-3-phenylpropylamino)-5-(3-fluorophenyl)-4-(4-pyridinyl)pyridine;
2-((S)-2-amino-3-phenylpropylamino)-5-(3-trifluoromethylphenyl)-4-(4-pyridinyl)pyridine;
2-((S)-2-amino-3-phenylpropylamino)-5-(3-isopropylphenyl)-4-(4-pyridinyl)pyridine;
6-((S)-2-Amino-3-phenylpropylamino)-3-(2-benzothiophenyl)-2-(4-pyridyl)pyridine;
6-((S)-2-Amino-3-phenylpropylamino)-3-(4-chloro-3-fluorophenyl)-2-(4-pyridyl)pyridine;
6-((S)-2-Amino-3-phenylpropylamino)-3-(4-methoxyphenyl)-2-(4-pyridyl)pyridine;
6-((S)-2-Amino-3-phenylpropylamino)-3-(3-isopropylphenyl)-2-(4-pyridyl)pyridine;
6-((S)-2-Amino-3-phenylpropylamino)-3-(4-chlorophenyl)-2-(4-pyridyl) pyridine;
6-((S)-2-Amino-3-phenylpropylamino)-3-(2-napthyl)-2-(4-pyridyl)pyridine;
6-((S)-2-Amino-3-phenylpropylamino)-3-(3-trifluoromethylphenyl)-2-(4-pyridyl)pyridine;
6-((S)-2-Amino-3-phenylpropylamino)-3-(3-methylphenyl)-2-(4-pyridyl)pyridine;
2-((S)-2-amino-3-phenylpropylamino)-5-(3-methylphenyl)-4-(4-pyridinyl)pyridine;

2-(3-phenylpropylamino)-5-(3-methylphenyl)-4-(4-pyridinyl)pyridine;
2-(3-phenylpropylamino)-4-(3-methylphenyl)-5-(4-pyridyl)pyridine;
2-(benzyloxy)-4-(3-methylphenyl)-5-(4-pyridyl)pyridine;
1-benzy1-4-(3-methylphenyl)-5-(4-pyridyl)-1H-pyrid-2-one;
2-(4-pyridylmethoxy)-4-(4-fluorophenyl)-5-(4-pyridyl)pyridine;
1-(4-pyridylmethoxy)-4-(4-fluorophenyl)-5-(4-pyridyl)-1H-pyrid-2-one; or
a pharmaceutically acceptable salt thereof.

13. A pharmaceutical composition comprising a compound according to any one of claims 1–12 and a pharmaceutically acceptable carrier.

14. A method of treatment of inflammation comprising administering an effective amount of a compound according to any one of claims 1–12.

15. A method of treatment of inflammation comprising administering an effective amount of a composition according to claim 13.

16. A method of treatment of rheumatoid arthritis, Pagets disease, osteophorosis, multiple myeloma, uveititis, acute or chronic myelogenous leukemia, pancreatic β cell destruction, osteoarthritis, rheumatoid spondylitis, gouty arthritis, inflammatory bowel disease, adult respiratory distress syndrome (ARDS), psoriasis, Crohn's disease, allergic rhinitis, ulcerative colitis, anaphylaxis, contact dermatitis, asthma, muscle degeneration, cachexia, Reiter's syndrome, type I diabetes, type II diabetes, bone resorption diseases, graft vs. host reaction, Alzheimer's disease, stroke, myocardial infarction, ischemia reperfusion injury, atherosclerosis, brain trauma, multiple sclerosis, cerebral malaria, sepsis, septic shock, toxic shock syndrome, fever, myalgias due to HIV-1, HIV-2, HIV-3, cytomegalovirus (CMV), influenza, adenovirus, the herpes viruses or herpes zoster infection in a mammal comprising administering an effective amount of a compound according to any one of claims 1–12.

17. A method of treatment of rheumatoid arthritis, Pagets disease, osteophorosis, multiple myeloma, uveititis, acute or chronic myelogenous leukemia, pancreatic β cell destruction, osteoarthritis, rheumatoid spondylitis, gouty arthritis, inflammatory bowel disease, adult respiratory distress syndrome (ARDS), psoriasis, Crohn's disease, allergic rhinitis, ulcerative colitis, anaphylaxis, contact dermatitis, asthma, muscle degeneration, cachexia, Reiter's syndrome, type I diabetes, type II diabetes, bone resorption diseases, graft vs. host reaction, Alzheimer's disease, stroke, myocardial infarction, ischemia reperfusion injury, atherosclerosis, brain trauma, multiple sclerosis, cerebral malaria, sepsis, septic shock, toxic shock syndrome, fever, myalgias due to HIV-1, HIV-2, HIV-3, cytomegalovirus (CMV), influenza, adenovirus, the herpes viruses or herpes zoster infection in a mammal comprising administering an effective amount of a composition according to claim 13.

18. A method of lowering plasma concentrations of either or both TNF-α and IL-1 comprising administering an effective amount of a compound according to any one of claims 1–12.

19. A method of lowering plasma concentrations of either or both TNF-α and IL-1 comprising administering an effective amount of a composition according to claim 13.

20. A method of lowering plasma concentrations of either or both IL-6 and IL-8 comprising administering an effective amount of a compound according to any one of claims 1–12.

21. A method of lowering plasma concentrations of either or both IL-6 and IL-8 comprising administering an effective amount of a composition according to claim 13.

22. A method of treatment of diabetes disease in a mammal comprising administering an effective amount of a compound according to any one of claims 1–12 to produce a glucagon antagonist effect.

23. A method of treatment of diabetes disease in a mammal comprising administering an effective amount of a pharmaceutical composition according to claim 13 to produce a glucagon antagonist effect.

24. A method of treatment of a pain disorder in a mammal comprising administering an effective amount of a compound according to any one of claims 1–12.

25. A method of treatment of a pain disorder in a mammal comprising administering an effective amount of a pharmaceutical composition according to claim 13.

26. A method of decreasing prostaglandins production in a mammal comprising administering an effective amount of a compound according to any one of claims 1–12.

27. A method of decreasing prostaglandins production in a mammal comprising administering an effective amount of a pharmaceutical composition according to claim 13.

28. A method of decreasing cyclooxygenase enzyme activity in a mammal comprising administering an effective amount of a compound according to any one of claims 1–12.

29. The method of claim 28 wherein the cyclooxygenase enzyme is COX-2.

30. A method of decreasing cyclooxygenase enzyme activity in a mammal comprising administering an effective amount of a pharmaceutical composition according to claim 13.

31. The method of claim 30 wherein the cyclooxygenase enzyme is COX-2.

* * * * *

UNITED STATES PATENT AND TRADEMARK OFFICE
CERTIFICATE OF CORRECTION

PATENT NO.    : 6,174,901 B1
DATED         : January 16, 2001
INVENTOR(S)   : Nathan B. Mantlo et al.

It is certified that error appears in the above-identified patent and that said Letters Patent is hereby corrected as shown below:

Column 1,
Line 53, change "(IL-β, IL-6)" to -- (IL-1β, IL-6) --.

Column 4,
Lines 12-17, the formula should appear as follows:  -- 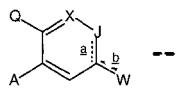 --
Line 49, change "Rhd 1" to -- $R_1$ --

Column 8,
Line 17, change "-S(O)$_2$13NR$_{22}$-C(O)R$_{21}$," to -- -S(O)$_2$-NR$_{22}$-C(O)-R$_{21}$, --.

Column 24,
Line 21, column $R^{12}$, change "4-pyrimdyl" to -- 4-pyridyl --.
Line 38, column $R^{12}$, change "4-pyrimidyl" to -- 4-pyridyl --.

Column 33,
Lines 1-5, Scheme 2, the formula should appear as follows:

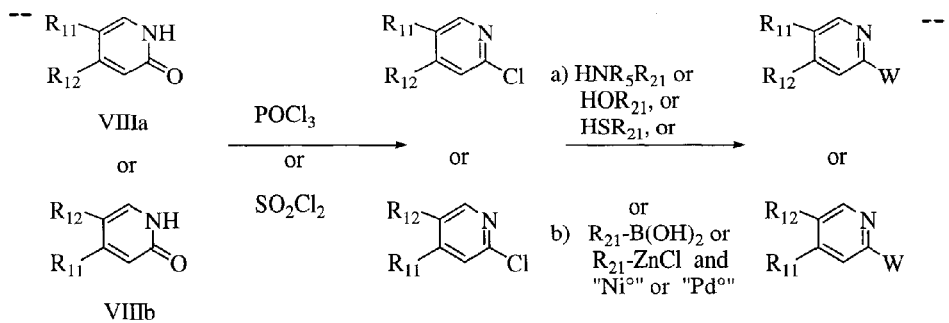

Column 39,
Lines 57-66, Scheme 14, the formula should appear as follows:

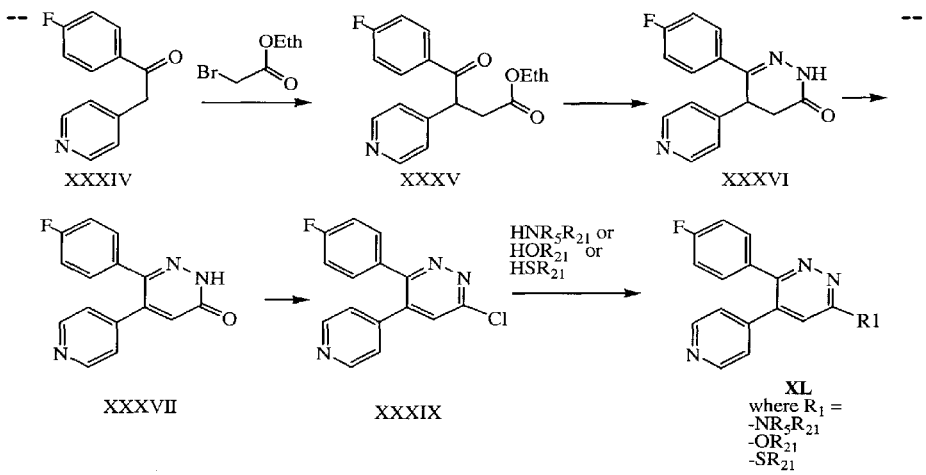

UNITED STATES PATENT AND TRADEMARK OFFICE
CERTIFICATE OF CORRECTION

PATENT NO. : 6,174,901 B1
DATED : January 16, 2001
INVENTOR(S) : Nathan B. Mantlo et al.

It is certified that error appears in the above-identified patent and that said Letters Patent is hereby corrected as shown below:

Column 45,
Line 2, change "$(M+H)^1$" to -- $(M+H)^+$ --.

Column 66,
Line 18, change "(3-methylohenyl)" to -- (3-methylphenyl) --.

Column 74,
Line 39, change "$C_{23}H_{17}N_3 FO$" to -- $C_{23}H_{17}N_2 FO$ --.

Column 78,
Line 18, change "$-20\mu$" to -- $-20°$ --.

Column 85,
Line 35, the formula should appear as follows: -- 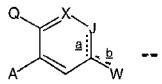 --
Line 42, insert "O" between "$R_2$" and "or".
Line 56, change "$-NR_5 R_{23}$" to -- $NR_5 R_{21}$ --.

Signed and Sealed this

Fourth Day of November, 2003

JAMES E. ROGAN
*Director of the United States Patent and Trademark Office*